(12) United States Patent
Smith et al.

(10) Patent No.: US 12,303,435 B2
(45) Date of Patent: May 20, 2025

(54) DISTRACTION FRAME FOR EFFECTING HIP DISTRACTION

(71) Applicant: Stryker Corp., Portage, MI (US)

(72) Inventors: Conrad Smith, Hollister, CA (US);
William Kaiser, Campbell, CA (US);
Chris Bowles, Hollister, CA (US);
Edson Lopes, San Jose, CA (US);
Ruben Cardenas, San Jose, CA (US);
Roger J. Malcolm, San Clemente, CA (US)

(73) Assignee: Stryker Corp., Portage, MI (US)

( * ) Notice: Subject to any disclaimer, the term of this patent is extended or adjusted under 35 U.S.C. 154(b) by 0 days.

(21) Appl. No.: 18/158,446

(22) Filed: Jan. 23, 2023

(65) Prior Publication Data
US 2023/0157916 A1 May 25, 2023

Related U.S. Application Data

(62) Division of application No. 15/890,124, filed on Feb. 6, 2018, now Pat. No. 11,559,455.
(Continued)

(51) Int. Cl.
*A61G 13/00* (2006.01)
*A61B 17/02* (2006.01)
(Continued)

(52) U.S. Cl.
CPC ........ *A61G 13/0081* (2016.11); *A61B 17/025* (2013.01); *A61F 5/04* (2013.01);
(Continued)

(58) Field of Classification Search
CPC . A61F 5/04; A61F 5/042; A61F 5/048; A61G 13/0036; A61G 13/0081;
(Continued)

(56) References Cited

U.S. PATENT DOCUMENTS

| 2,150,314 A | 3/1939 | Bell |
| D130,079 S | 10/1941 | Weller |

(Continued)

FOREIGN PATENT DOCUMENTS

| DE | 102005023477 A1 | 11/2006 |
| DE | 202009003314 U1 | 5/2009 |

(Continued)

OTHER PUBLICATIONS

"Hip Distraction System: Advanced solutions for supine hip arthroscopy procedures," technical brochure published by Arthrex, 2020; 6 pages.
(Continued)

*Primary Examiner* — Keri J Nelson
(74) *Attorney, Agent, or Firm* — Morrison & Foerster LLP

(57) ABSTRACT

A distraction frame includes a table mount for removably mounting the distraction frame to a surgical table; at least one horizontal strut mounted to the table mount; at least one vertical strut mounted to the at least one horizontal strut; and at least one distractor mounted to the at least one vertical strut, wherein the at least one distractor is configured for connection to a limb of a patient and for applying a distraction force to the limb of the patient; wherein the table mount comprises at least one wheel for selectively supporting the table mount above the floor and the at least one horizontal strut comprises at least one caster for selectively rollably supporting the at least one horizontal strut on the floor so that the distraction frame can be selectively moved to the surgical table supported by the at least one wheel and the at least one caster.

16 Claims, 46 Drawing Sheets

Related U.S. Application Data

(60) Provisional application No. 62/546,686, filed on Aug. 17, 2017, provisional application No. 62/455,238, filed on Feb. 6, 2017.

(51) Int. Cl.
  *A61F 5/04*     (2006.01)
  *A61F 5/042*    (2006.01)
  *A61G 13/04*    (2006.01)
  *A61G 13/10*    (2006.01)
  *A61G 13/12*    (2006.01)
  A61B 17/66    (2006.01)
  A61F 5/37     (2006.01)
  A61G 7/005    (2006.01)

(52) U.S. Cl.
  CPC ............. *A61F 5/042* (2013.01); *A61G 13/04* (2013.01); *A61G 13/104* (2013.01); *A61G 13/123* (2013.01); *A61G 13/1245* (2013.01); *A61G 13/125* (2013.01); *A61G 13/129* (2013.01); *A61B 2017/0268* (2013.01); *A61B 2017/0275* (2013.01); *A61B 17/66* (2013.01); *A61F 5/37* (2013.01); *A61G 7/005* (2013.01); *A61G 2210/50* (2013.01)

(58) Field of Classification Search
  CPC ................ A61G 13/104; A61G 13/123; A61G 13/1245; A61G 13/129; A61B 17/66
  See application file for complete search history.

(56) References Cited

U.S. PATENT DOCUMENTS

| | | | |
|---|---|---|---|
| 2,477,562 | A | 8/1949 | Roger |
| D171,677 | S | 3/1954 | Adler |
| 2,732,269 | A | 4/1954 | Astroff |
| 3,220,022 | A | 11/1965 | Ted |
| D221,035 | S | 6/1971 | Raines |
| 3,745,996 | A | 7/1973 | Rush |
| 3,808,644 | A | 5/1974 | Schoch |
| D264,531 | S | 5/1982 | Trode |
| 4,539,763 | A | 9/1985 | Walkhoff |
| 4,551,932 | A | 11/1985 | Schoch |
| 4,573,482 | A | 3/1986 | Williams, Jr. |
| 4,708,510 | A | 11/1987 | Mcconnell et al. |
| 4,835,886 | A | 6/1989 | Chemello et al. |
| 4,841,650 | A | 6/1989 | Dodge et al. |
| 4,865,303 | A | 9/1989 | Hall |
| 5,052,128 | A | 10/1991 | Lonardo |
| 5,162,039 | A | 11/1992 | Dahners |
| 5,177,882 | A | 1/1993 | Berger |
| 5,249,377 | A | 10/1993 | Walkhoff |
| 5,287,575 | A | 2/1994 | Allen et al. |
| 5,306,231 | A | 4/1994 | Cullum et al. |
| 5,560,577 | A | 10/1996 | Keselman |
| 5,582,379 | A | 12/1996 | Keselman et al. |
| 5,608,934 | A | 3/1997 | Torrie et al. |
| D385,040 | S | 10/1997 | Keselman |
| D387,581 | S | 12/1997 | Parker et al. |
| 5,702,389 | A | 12/1997 | Taylor et al. |
| D389,580 | S | 1/1998 | Keselman et al. |
| 5,728,095 | A | 3/1998 | Taylor et al. |
| 5,819,440 | A | 10/1998 | Okajima |
| 5,918,330 | A | 7/1999 | Navarro et al. |
| 5,971,984 | A | 10/1999 | Taylor et al. |
| 6,109,625 | A | 8/2000 | Hewitt |
| 6,162,223 | A | 12/2000 | Orsak et al. |
| 6,286,164 | B1 | 9/2001 | Lamb et al. |
| 6,295,671 | B1 | 10/2001 | Reesby |
| 6,678,908 | B2 | 1/2004 | Borders et al. |
| D546,599 | S | 7/2007 | Goldberg |
| 7,237,556 | B2 | 7/2007 | Smothers et al. |
| 7,337,483 | B2 | 3/2008 | Boucher et al. |
| 7,343,635 | B2 | 3/2008 | Jackson |
| 7,477,926 | B2 | 1/2009 | Mccombs |
| 7,520,007 | B2 | 4/2009 | Skripps |
| 7,520,008 | B2 | 4/2009 | Wong et al. |
| 7,565,708 | B2 | 7/2009 | Jackson |
| 7,572,292 | B2 | 8/2009 | Crabtree et al. |
| 7,591,050 | B2 | 9/2009 | Hammerslag |
| 7,600,281 | B2 | 10/2009 | Skripps |
| 7,669,262 | B2 | 3/2010 | Skripps et al. |
| 7,677,249 | B2 | 3/2010 | Kong et al. |
| 7,739,762 | B2 | 6/2010 | Lamb et al. |
| RE41,412 | E | 7/2010 | Van Steenburg |
| 7,762,975 | B2 | 7/2010 | Memminger |
| 7,832,401 | B2 | 11/2010 | Torrie et al. |
| 7,862,570 | B2 | 1/2011 | Russell et al. |
| 7,878,992 | B2 | 2/2011 | Mitsuishi et al. |
| 7,882,583 | B2 | 2/2011 | Skripps |
| 7,947,006 | B2 | 5/2011 | Torrie et al. |
| 7,949,006 | B2 | 5/2011 | Jagadesan et al. |
| 7,949,386 | B2 | 5/2011 | Buly et al. |
| 7,979,932 | B2 | 7/2011 | Liang |
| 8,011,045 | B2 | 9/2011 | Skripps |
| 8,037,884 | B2 | 10/2011 | Weinstein et al. |
| 8,055,487 | B2 | 11/2011 | James |
| 8,060,960 | B2 | 11/2011 | Jackson |
| 8,109,942 | B2 | 2/2012 | Carson |
| 8,152,816 | B2 | 4/2012 | Tuma et al. |
| D665,912 | S | 8/2012 | Skripps |
| 8,234,730 | B2 | 8/2012 | Skripps |
| 8,234,731 | B2 | 8/2012 | Skripps |
| 8,256,050 | B2 | 9/2012 | Wong et al. |
| 8,281,434 | B2 | 10/2012 | Skripps |
| 8,322,342 | B2 | 12/2012 | Soto et al. |
| 8,388,553 | B2 | 3/2013 | James et al. |
| 8,397,323 | B2 | 3/2013 | Skripps et al. |
| 8,413,660 | B2 | 4/2013 | Weinstein et al. |
| 8,464,720 | B1 | 6/2013 | Pigazzi et al. |
| 8,469,911 | B2 | 6/2013 | Hiebert |
| 8,486,070 | B2 | 7/2013 | Morgan et al. |
| 8,491,597 | B2 | 7/2013 | Russell et al. |
| 8,491,664 | B2 | 7/2013 | Mcmahon et al. |
| 8,511,314 | B2 | 8/2013 | Pigazzi et al. |
| 8,545,570 | B2 | 10/2013 | Crabtree et al. |
| 8,555,439 | B2 | 10/2013 | Skripps et al. |
| 8,570,187 | B2 | 10/2013 | Janna et al. |
| 8,611,697 | B2 | 12/2013 | Nathaniel et al. |
| 8,679,187 | B2 | 3/2014 | Allen et al. |
| 8,690,806 | B2 | 4/2014 | Hiebert |
| 8,690,807 | B2 | 4/2014 | Hiebert |
| 8,702,712 | B2 | 4/2014 | Jordan et al. |
| 8,707,484 | B2 | 4/2014 | Jackson et al. |
| 8,707,486 | B2 | 4/2014 | Chella et al. |
| 8,719,979 | B2 | 5/2014 | Jackson |
| 8,721,643 | B2 | 5/2014 | Morgan et al. |
| 8,795,312 | B2 | 8/2014 | Fan et al. |
| 8,806,679 | B2 | 8/2014 | Soto et al. |
| 8,826,474 | B2 | 9/2014 | Jackson |
| 8,826,475 | B2 | 9/2014 | Jackson |
| 8,828,009 | B2 | 9/2014 | Allen et al. |
| 8,833,707 | B2 | 9/2014 | Steinberg et al. |
| 8,839,471 | B2 | 9/2014 | Jackson |
| 8,844,077 | B2 | 9/2014 | Jackson et al. |
| 8,845,568 | B2 | 9/2014 | Clark et al. |
| 8,856,986 | B2 | 10/2014 | Jackson |
| 8,890,511 | B2 | 11/2014 | Belew |
| 8,893,333 | B2 | 11/2014 | Soto et al. |
| 8,894,716 | B2 | 11/2014 | Mcmahon et al. |
| 8,938,826 | B2 | 1/2015 | Jackson |
| 8,944,065 | B2 | 2/2015 | Slusarz, Jr. |
| 8,945,026 | B2 | 2/2015 | Moser et al. |
| 8,978,180 | B2 | 3/2015 | Jackson |
| 8,986,228 | B2 | 3/2015 | Auchinleck et al. |
| 8,997,284 | B2 | 4/2015 | Kreuzer et al. |
| 8,997,286 | B2 | 4/2015 | Wyslucha et al. |
| 8,997,749 | B2 | 4/2015 | Drake et al. |
| 9,056,012 | B2 | 6/2015 | Crabtree, Jr. et al. |
| 9,072,646 | B2 | 7/2015 | Skripps et al. |
| 9,085,915 | B1 | 7/2015 | Emmett |
| 9,101,393 | B2 | 8/2015 | Jordan et al. |

(56) References Cited

U.S. PATENT DOCUMENTS

| | | |
|---|---|---|
| 9,107,792 B2 | 8/2015 | Catacchio et al. |
| 9,119,610 B2 | 9/2015 | Matta et al. |
| 9,161,875 B2 | 10/2015 | Clark et al. |
| 9,161,876 B2 | 10/2015 | Pigazzi et al. |
| 9,173,649 B2 | 11/2015 | Clark et al. |
| 9,180,062 B2 | 11/2015 | Jackson |
| 9,186,291 B2 | 11/2015 | Jackson et al. |
| 9,198,817 B2 | 12/2015 | Jackson |
| 9,205,013 B2 | 12/2015 | Jackson |
| 9,211,223 B2 | 12/2015 | Jackson |
| 9,226,865 B2 | 1/2016 | Jackson et al. |
| 9,233,043 B2 | 1/2016 | Labedz et al. |
| 9,265,679 B2 | 2/2016 | Jackson |
| 9,289,342 B2 | 3/2016 | Jackson |
| 9,295,433 B2 | 3/2016 | Jackson et al. |
| 9,295,556 B2 | 3/2016 | Perez, III et al. |
| 9,301,897 B2 | 4/2016 | Jackson |
| 9,308,145 B2 | 4/2016 | Jackson |
| 9,331,262 B2 | 5/2016 | Maejima et al. |
| RE46,032 E | 6/2016 | Torrie et al. |
| 9,364,380 B2 | 6/2016 | Jackson |
| 9,456,945 B2 | 10/2016 | Jackson |
| 9,468,576 B2 | 10/2016 | Jackson |
| 9,510,987 B2 | 12/2016 | Jackson et al. |
| 9,549,865 B2 | 1/2017 | Hiebert |
| 9,610,206 B2 | 4/2017 | Jackson |
| 9,672,662 B2 | 6/2017 | Scanlan et al. |
| 9,750,656 B1 | 9/2017 | Pigazzi et al. |
| 9,782,287 B2 | 10/2017 | Pigazzi et al. |
| 9,931,262 B2 | 4/2018 | Pigazzi et al. |
| 9,936,941 B2 | 4/2018 | Weisel et al. |
| 9,949,883 B1 | 4/2018 | Pigazzi et al. |
| 10,034,806 B1 | 7/2018 | Greenhalgh, Sr. |
| D832,334 S | 10/2018 | Kushner et al. |
| 10,130,542 B1 | 11/2018 | Strawder |
| 10,159,520 B2 | 12/2018 | Krickeberg et al. |
| 10,765,580 B1 | 9/2020 | Augustine |
| 10,828,218 B2 | 11/2020 | Shandas et al. |
| 10,912,698 B1 | 2/2021 | Termanini |
| 2002/0023298 A1 | 2/2002 | Lamb et al. |
| 2004/0003468 A1 | 1/2004 | Mitsuishi et al. |
| 2004/0092854 A1 | 5/2004 | D'Amico |
| 2004/0133979 A1 | 7/2004 | Newkirk et al. |
| 2004/0133983 A1 | 7/2004 | Newkirk et al. |
| 2005/0160533 A1 | 7/2005 | Boucher et al. |
| 2006/0047228 A1 | 3/2006 | Petelenz et al. |
| 2006/0074366 A1 | 4/2006 | Ryan et al. |
| 2006/0100562 A1 | 5/2006 | Pamplin |
| 2006/0130713 A1 | 6/2006 | Jones et al. |
| 2006/0185090 A1 | 8/2006 | Jackson |
| 2006/0271056 A1 | 11/2006 | Terrill-Grisoni et al. |
| 2007/0161935 A1 | 7/2007 | Torrie et al. |
| 2007/0251011 A1 | 11/2007 | Matta et al. |
| 2007/0277350 A1 | 12/2007 | Hines |
| 2008/0214976 A1 | 9/2008 | Memminger |
| 2008/0216231 A1 | 9/2008 | Lambarth et al. |
| 2008/0309052 A1 | 12/2008 | Neiley et al. |
| 2009/0044339 A1 | 2/2009 | Morin et al. |
| 2011/0023893 A1 | 2/2011 | Striggow et al. |
| 2011/0119829 A1 | 5/2011 | Skripps et al. |
| 2011/0143898 A1 | 6/2011 | Trees |
| 2011/0190676 A1 | 8/2011 | Torrie et al. |
| 2012/0059376 A1 | 3/2012 | Rains et al. |
| 2012/0073476 A1 | 3/2012 | Lai |
| 2012/0204885 A1 | 8/2012 | Koch |
| 2012/0233782 A1 | 9/2012 | Kreuzer et al. |
| 2012/0240938 A1 | 9/2012 | Pamichev |
| 2012/0255122 A1 | 10/2012 | Diel et al. |
| 2012/0259261 A1 | 10/2012 | Clark et al. |
| 2012/0259343 A1 | 10/2012 | Clark et al. |
| 2012/0305005 A1 | 12/2012 | Keith-Lucas et al. |
| 2013/0081635 A1 | 4/2013 | Drake et al. |
| 2013/0111666 A1 | 5/2013 | Jackson |
| 2013/0133137 A1 | 5/2013 | Jackson et al. |
| 2013/0174853 A1 | 7/2013 | Pigazzi et al. |
| 2013/0174854 A1 | 7/2013 | Pigazzi et al. |
| 2013/0191994 A1 | 8/2013 | Bellows et al. |
| 2013/0199541 A1 | 8/2013 | Sluss et al. |
| 2013/0247301 A1 | 9/2013 | Daley et al. |
| 2013/0269710 A1 | 10/2013 | Moriarty et al. |
| 2013/0312187 A1 | 11/2013 | Jackson |
| 2013/0312188 A1 | 11/2013 | Jackson |
| 2013/0318721 A1 | 12/2013 | Gauta |
| 2013/0338792 A1 | 12/2013 | Schmieding et al. |
| 2013/0345605 A1 | 12/2013 | Steele |
| 2014/0020181 A1 | 1/2014 | Jackson |
| 2014/0033434 A1 | 2/2014 | Jackson |
| 2014/0068863 A1 | 3/2014 | Clark et al. |
| 2014/0068866 A1 | 3/2014 | Catacchio et al. |
| 2014/0082842 A1 | 3/2014 | Jackson |
| 2014/0173827 A1 | 6/2014 | Hiebert |
| 2014/0174451 A1 | 6/2014 | Hiebert |
| 2014/0196212 A1 | 7/2014 | Jackson |
| 2014/0201913 A1 | 7/2014 | Jackson |
| 2014/0201914 A1 | 7/2014 | Jackson |
| 2014/0208512 A1 | 7/2014 | Jackson |
| 2014/0208513 A1 | 7/2014 | Hiebert |
| 2014/0215718 A1 | 8/2014 | Wootton |
| 2014/0215855 A1 | 8/2014 | Frey |
| 2014/0222407 A1 | 8/2014 | Jordan et al. |
| 2014/0283845 A1 | 9/2014 | Slusarz, Jr. |
| 2014/0309646 A1 | 10/2014 | Fan et al. |
| 2014/0317847 A1 | 10/2014 | Jackson |
| 2014/0324056 A1 | 10/2014 | Nikolchev et al. |
| 2014/0352072 A1 | 12/2014 | Holladay |
| 2014/0359941 A1 | 12/2014 | Sharps et al. |
| 2014/0366271 A1 | 12/2014 | Marshall et al. |
| 2015/0008201 A1 | 1/2015 | Qiang et al. |
| 2015/0032041 A1 | 1/2015 | Ingimundarson et al. |
| 2015/0059094 A1 | 3/2015 | Jackson |
| 2015/0067985 A1 | 3/2015 | Gaenzle |
| 2015/0088044 A1 | 3/2015 | Walborn et al. |
| 2015/0122268 A1 | 5/2015 | Slusarz, Jr. |
| 2015/0135441 A1 | 5/2015 | Sommer |
| 2015/0150743 A1 | 6/2015 | Jackson |
| 2015/0164724 A1 | 6/2015 | Drake et al. |
| 2015/0196447 A1 | 7/2015 | Henderson et al. |
| 2015/0202106 A1 | 7/2015 | Hight et al. |
| 2015/0231013 A1 | 8/2015 | Bernardoni et al. |
| 2015/0238273 A1 | 8/2015 | Jordan et al. |
| 2015/0238380 A1 | 8/2015 | Kreuzer et al. |
| 2015/0245915 A1 | 9/2015 | Crabtree, Jr. et al. |
| 2015/0245969 A1 | 9/2015 | Hight et al. |
| 2015/0245971 A1 | 9/2015 | Bernardoni et al. |
| 2015/0272681 A1 | 10/2015 | Skripps et al. |
| 2015/0290064 A1 | 10/2015 | Kreuzer et al. |
| 2015/0297435 A1 | 10/2015 | Visco |
| 2015/0342813 A1 | 12/2015 | Catacchio et al. |
| 2015/0366622 A1 | 12/2015 | Wyslucha et al. |
| 2016/0008201 A1 | 1/2016 | Jackson et al. |
| 2016/0038364 A1 | 2/2016 | Jackson |
| 2016/0051432 A1 | 2/2016 | Clark et al. |
| 2016/0067135 A1 | 3/2016 | Pigazzi et al. |
| 2016/0095784 A1 | 4/2016 | Catacchio et al. |
| 2016/0095785 A1 | 4/2016 | Catacchio et al. |
| 2016/0106612 A1 | 4/2016 | Clark et al. |
| 2016/0120720 A1 | 5/2016 | Hirsch |
| 2016/0120726 A1 | 5/2016 | Moriarty et al. |
| 2016/0184154 A1 | 6/2016 | Lafleche et al. |
| 2016/0228281 A1 | 8/2016 | Marshall et al. |
| 2016/0279007 A1 | 9/2016 | Flatt |
| 2016/0287461 A1 | 10/2016 | Naughton |
| 2016/0317237 A1 | 11/2016 | Geiger |
| 2016/0338691 A1 | 11/2016 | Weber et al. |
| 2017/0239118 A1 | 8/2017 | Cole |
| 2018/0140309 A1 | 5/2018 | Fouts et al. |
| 2018/0140493 A1 | 5/2018 | Shandas et al. |
| 2018/0221190 A1 | 8/2018 | Kaiser et al. |
| 2018/0221229 A1 | 8/2018 | Kaiser et al. |
| 2018/0221230 A1 | 8/2018 | Smith et al. |
| 2019/0091089 A1 | 3/2019 | Shandas et al. |
| 2020/0129356 A1 | 4/2020 | Shandas et al. |
| 2021/0106480 A1 | 4/2021 | Gomez et al. |
| 2022/0096304 A1 | 3/2022 | Kaiser et al. |

(56) References Cited

U.S. PATENT DOCUMENTS

| | | |
|---|---|---|
| 2023/0061000 A1 | 3/2023 | Shandas et al. |
| 2023/0240927 A1 | 8/2023 | Kaiser |
| 2024/0099919 A1 | 3/2024 | Kaiser |

FOREIGN PATENT DOCUMENTS

| | | |
|---|---|---|
| DE | 202012101347 U1 | 6/2012 |
| DE | 102011016456 B4 | 10/2012 |
| EP | 2574325 A2 | 4/2013 |
| EP | 2623082 A2 | 8/2013 |
| EP | 2618313 B1 | 7/2014 |
| EP | 2873405 A1 | 5/2015 |
| EP | 2982880 A2 | 2/2016 |
| EP | 2802305 B1 | 10/2017 |
| WO | 03/061544 A1 | 7/2003 |
| WO | 2006/091239 A2 | 8/2006 |
| WO | 2007/021806 A2 | 2/2007 |
| WO | 2007/080454 A2 | 7/2007 |
| WO | 2008/150731 A1 | 12/2008 |
| WO | 2009/062324 A1 | 5/2009 |
| WO | 2013/034916 A1 | 3/2013 |
| WO | 2013/106426 A2 | 7/2013 |
| WO | 2014/043538 A1 | 3/2014 |
| WO | 2014/045194 A1 | 3/2014 |
| WO | 2014/045199 A1 | 3/2014 |
| WO | 2014/153329 A1 | 9/2014 |
| WO | 2014/205218 A1 | 12/2014 |
| WO | 2016/017479 A1 | 2/2016 |
| WO | 2016/197142 A1 | 12/2016 |

OTHER PUBLICATIONS

"Secure and easy patient positioning," technical brochure published by Smith & Nephew, May 2015; 8 pages.
Communication pursuant to Article 94(3) EPC dated Mar. 12, 2020, directed to EP Application No. 16804665.4; 9 pages.
Extended European Search Report dated Jan. 7, 2019, directed to EP Application No. 16804665.4; 8 pages.
Extended Search Report dated Feb. 10, 2021, directed to EP Application No. 18747256.8; 10 pages.
Extended Search Report dated Nov. 3, 2020, directed to EP Application No. 18747404.4; 6 pages.
Harris, The Pink Hip Kit SN: Postless Poitioning System—72205286, Xodus Medical, 2019, https://www.xodusmedical.com/Product/HIP40614SN.
Harris, The Pink Hip Kit SN: Postless Positioning System—HIP40614SN, Xodus Medical, 2019.
Hip Distraction System: Advanced solutions for supine hip arthroscopy procedures, Arthrex, 2013, pp. 1-6.
Intention to Grant dated Jan. 23, 2024, directed to EP Application No. 16 804 665.4; 8 pages.
Intention to Grant dated Sep. 12, 2023, directed to EP Application No. 16 804 665.4; 8 pages.
International Search Report and Written Opinion dated Apr. 13, 2018, directed to PCT/US2018/017099; 9 pages.
International Search Report and Written Opinion dated Aug. 31, 2016, directed to International Application No. PCT/US2016/036090; 8 pages.
International Search Report and Written Opinion dated May 30, 2018, directed to International Application No. PCT/US2018/017088; 13 pages.
Kaiser et al., U.S. Advisory Action dated Mar. 1, 2022, directed to U.S. Appl. No. 15/890,047; 4 pages.
Kaiser et al., U.S. Notice of Allowance and Fee(s) Due mailed Feb. 15, 2023, directed to U.S. Appl. No. 15/890,047; 11 pages.
Kaiser et al., U.S. Notice of Allowance and Fee(s) Due mailed Sep. 15, 2022, directed to U.S. Appl. No. 17/488,213; 9 pages.
Kaiser et al., U.S. Office Action dated Apr. 19, 2024, directed to U.S. Appl. No. 18/161,851; 12 pages.
Kaiser et al., U.S. Office Action dated Apr. 29, 2022, directed to U.S. Appl. No. 15/890,047; 21 pages.
Kaiser et al., U.S. Office Action dated Jan. 11, 2021, directed to U.S. Appl. No. 15/890,047; 20 pages.
Kaiser et al., U.S. Office Action dated Jun. 25, 2021, directed to U.S. Appl. No. 15/890,047; 19 pages.
Kaiser et al., U.S. Office Action dated Nov. 15, 2021, directed to U.S. Appl. No. 15/890,047; 20 pages.
Kaiser et al., U.S. Office Action dated Nov. 9, 2023, directed to U.S. Appl. No. 18/161,851; 10 pages.
Kaiser et al., U.S. Office Action dated Oct. 28, 2022, directed to U.S. Appl. No. 15/890,047; 24 pages.
Kaiser et al., U.S. Office Action dated Sep. 22, 2020, directed to U.S. Appl. No. 15/890,047; 14 pages.
Kaiser et al., U.S. Appl. No. 62/954,888, filed Dec. 30, 2019, for "Apparatus and Method for Patient Positioning"[A copy is not submitted herewith pursuant to the waiver of 37 C.F.R. § 1.98(a)(2)(iii) issued by the Office on Sep. 21, 2004.].
Kaiser et al., U.S. Restriction Requirement dated Jul. 2, 2020, directed to U.S. Appl. No. 15/890,047; 13 pages.
Klauschie et al. (Jul./Aug. 2010). "Use of Anti-Skid Material and Patient-Positioning to Prevent Patient Shifting during Robotic-Assisted Gynecologic Procedures," The Journal of Minimally Invasive Gynecology 17(4):504-507.
Kollmorgen, Robert C., The Pink Hip Kit®: Postless Hip Arthroscopy Positioning System, Xodus Medical.
Mei-Dan et al. (Mar. 2018). "Hip Distraction Without a Perineal Post: A Prospective Study of 1000 Hip Arthroscopy Cases, The American Journal of Sports Medicine" 46(3):632-641.
Mei-Dan, O. et al. Hip Arthroscopy Distraction Without the Use of Perineal Post: Prospective Study (Abstract), vol. 36, No. 1, Jan. 2013, pp. e1-e5.
Merriam-Webster, "outrigger," https://www.merriam-webster.com/dictionary/outrigger, retrieved on Sep. 9, 2020; 1 page.
Office Action dated Dec. 23, 2021, directed to EP Application No. 16 804 665.4; 5 pages.
Office Action dated Feb. 8, 2023, directed to EP Application No. 18 747 404.4; 5 pages.
Office Action dated Jan. 19, 2024, directed to EP Application No. 18 747 256.8; 6 pages.
Office Action dated Jul. 5, 2022, directed to EP Application No. 18 747 256.8; 4 pages.
Office Action dated May 4, 2023, directed to EP Application No. 18 747 256.8; 9 pages.
Opfell, A., Hip Arthroscopy & Fracture Kit: Maximize patient safety during arthroscopic hip procedures, Xodus Medical, Jul. 12, 2018.
Pink Pad—Advanced Trendelenburg Positioning System, Xodus Medical Inc., 2018, https://www.xodusmedical.com/pinkpad.
Shandas et al., U.S. Advisory Action dated May 19, 2021, directed to U.S. Appl. No. 15/579,409; 3 pages.
Shandas et al., U.S. Notice of Allowance and Fee(s) Due mailed Feb. 10, 2020, directed to U.S. Appl. No. 16/728,876; 10 pages.
Shandas et al., U.S. Notice of Allowance and Fee(s) Due mailed Feb. 16, 2022, directed to U.S. Appl. No. 15/579,409; 10 pages.
Shandas et al., U.S. Notice of Allowance and Fee(s) Due mailed Jul. 1, 2020, directed to U.S. Appl. No. 16/728,876; 8 pages.
Shandas et al., U.S. Notice of Allowance and Fee(s) Due mailed May 2, 2024, directed to U.S. Appl. No. 17/811,862; 7 pages.
Shandas et al., U.S. Office Action dated Dec. 26, 2023, directed to U.S. Appl. No. 17/811,862; 12 pages.
Shandas et al., U.S. Office Action dated Feb. 10, 2021, directed to U.S. Appl. No. 15/579,409; 13 pages.
Shandas et al., U.S. Office Action dated Jul. 8, 2021, directed to U.S. Appl. No. 15/579,409; 11 pages.
Shandas et al., U.S. Office Action dated Sep. 8, 2020, directed to U.S. Appl. No. 15/579,409; 8 pages.
Shandas et al., U.S. Office Action mailed Apr. 26, 2019, directed to U.S. Appl. No. 16/197,913; 17 pages.
Shandas et al., U.S. Office Action mailed Oct. 7, 2019, directed to U.S. Appl. No. 16/197,913; 17 pages.
Shandas et al., U.S. Restriction Requirement dated May 13, 2020, directed to U.S. Appl. No. 15/579,409; 8 pages.

(56) References Cited

OTHER PUBLICATIONS

Smith et al., U.S. Notice of Allowance and Fee(s) Due mailed Sep. 21, 2022, directed to U.S. Appl. No. 15/890,124; 8 pages.
Smith et al., U.S. Office Action dated Mar. 22, 2021 directed to U.S. Appl. No. 15/890,124; 39 pages.
Smith et al., U.S. Advisory Action dated Jun. 28, 2021, directed to U.S. Appl. No. 15/890,124; 4 pages.
Smith et al., U.S. Election Requirement dated Mar. 17, 2020, directed to U.S. Appl. No. 15/890,124; 7 pages.
Smith et al., U.S. Notice of Allowance and Fee(s) Due mailed Apr. 26, 2022, directed to U.S. Appl. No. 15/890,124; 10 pages.
Smith et al., U.S. Office Action mailed Sep. 16, 2020, directed to U.S. Appl. No. 15/890,124; 29 pages.
Soule Medical, 2019, https://www.soulemedical.com.
Steep Trendelenburg Positioners, Prime Medical LLC, 2019, http://primemedicalllc.com/steep-trendelenburg-positioners/.
Terry, M.A., Arthroscopic Hip Patient Positioning Using the Advanced Supine Hip Positioning System: Hip Technique Guide, Smith & Nephew, 2013, pp. 1-8.
The Pink Pad XL®: Advanced Trendelenburg Positioning System, Xodus Medical, 2018.
Trendelenburg Positioning Kits, Soule Medical, 2018, https://www.soulemedical.com/index.php/trendelenburg-positioning-kit.
U.S. Surgitech, Inc. (Mar. 2019). "SurgyPad—A Unique & Revolutionary Patient Positioning System" Brochure; 1 page.
Xodus Medical. (Aug. 2019) "Maximizing Trendelenburg Safety—Advanced Trendelenburg Patient Positioning System," located at https://xodusmedical.com/ProductCategory/Trendelenburg; (14 pages).
Young, D.A. et al., Technique allows for hip arthoscopy distraction without perineal post, Orthopedics Today, Jun. 2013, https://www.healio.com/orthopedics/arthroscopy/news/print/orthopedics-today/%7Bac540b4c-9b43-4736-ae8a-606b1457af8b%7D/technique-allows-for-hip-arthroscopy-distraction-without-perineal-post.

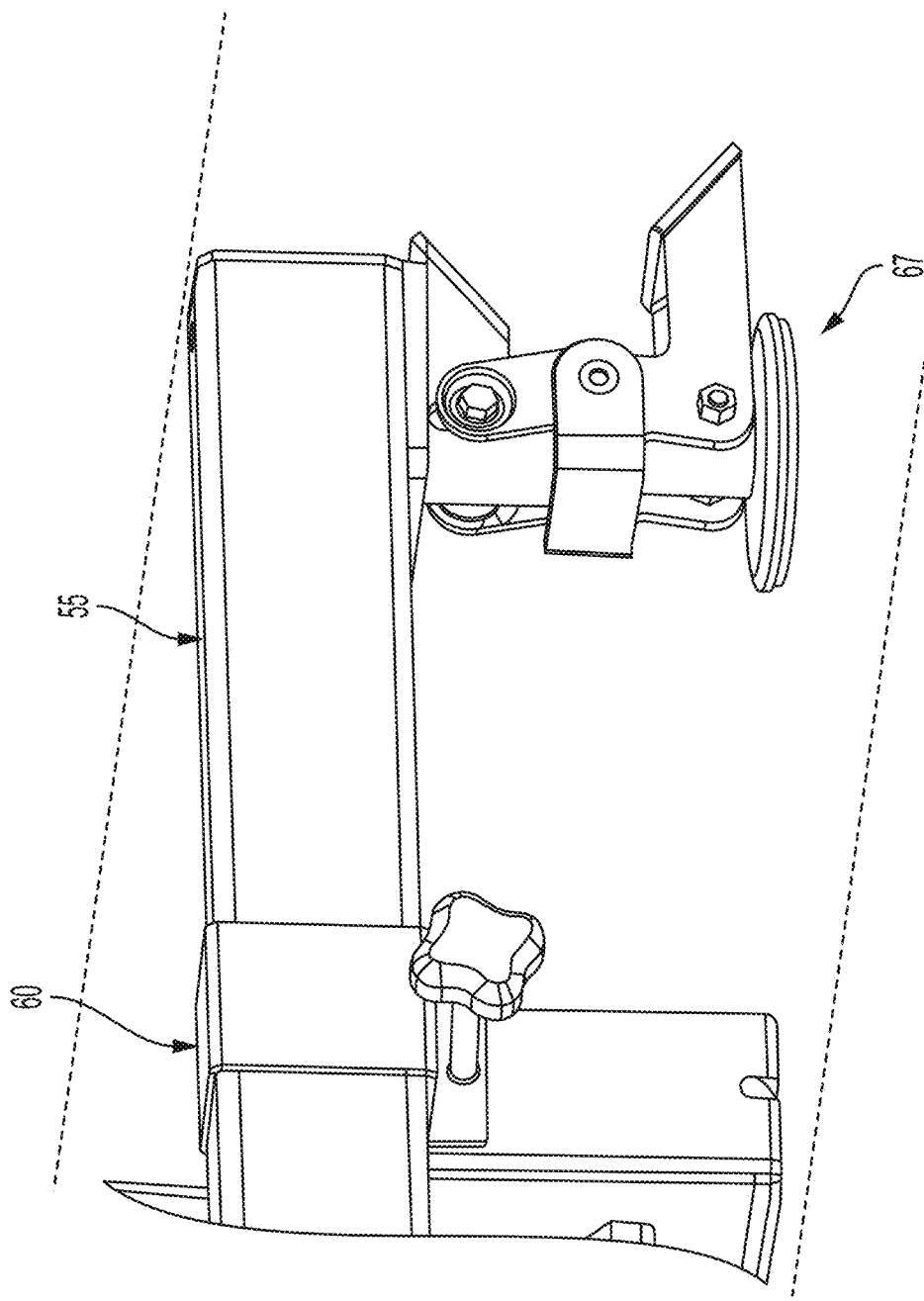

DISTRACTION FRAME FOR EFFECTING HIP DISTRACTION

CROSS-REFERENCE TO RELATED APPLICATIONS

This application is a divisional of U.S. patent application Ser. No. 15/890,124, filed Feb. 6, 2018, which claims the benefit of U.S. Provisional Application No. 62/455,238, filed Feb. 6, 2017, and U.S. Provisional Application No. 62/546,686, filed Aug. 17, 2017, the entire contents of each are hereby incorporated herein by reference.

FIELD OF THE INVENTION

This invention relates to medical apparatus in general, and more particularly to medical apparatus for effecting hip distraction.

BACKGROUND OF THE INVENTION

When performing surgical procedures on the hip joint, it is common to distract the hip joint prior to the surgery in order to provide additional room within the hip joint during the surgery and in order to better present selected anatomy to the surgeon. This hip distraction is commonly achieved by applying a distraction force to the distal end of the leg of the patient. Currently, a surgical boot is placed on the foot and lower leg of the patient, the surgical boot is connected to a distraction frame, and then the distraction frame is used to apply a distraction force to the surgical boot, whereby to apply a distraction force to the leg of the patient, whereby to distract and position the hip joint.

The present invention is intended to provide a new and improved distraction frame for applying a distraction force to the leg of the patient so as to effect hip distraction and to allow for leg positioning.

SUMMARY OF THE INVENTION

The present invention provides a new and improved distraction frame for applying a distraction force to the leg of the patient so as to effect hip distraction and to allow for leg positioning.

In one form of the invention, there is provided a distraction frame for use with a surgical table, wherein the surgical table comprises a base for positioning on a floor, the distraction frame comprising a table mount for fixation to the base of the surgical table; at least one horizontal strut mounted to the table mount; at least one vertical strut mounted to the at least one horizontal strut; and at least one distraction mechanism mounted to the at least one vertical strut, wherein the at least one distraction mechanism is configured for connection to a limb of a patient and for applying a distraction force to the limb of the patient; wherein the table mount is configured to transfer to the floor a force moment imposed on the table mount when the at least one distraction mechanism applies a distraction force to a limb of a patient.

In another form of the invention, there is provided a method for distracting a limb of a patient, the method comprising: providing a distraction frame for use with a surgical table, wherein the surgical table comprises a base for positioning on a floor, the distraction frame comprising: a table mount for fixation to the base of the surgical table; at least one horizontal strut mounted to the table mount; at least one vertical strut mounted to the at least one horizontal strut; and at least one distraction mechanism mounted to the at least one vertical strut, wherein the at least one distraction mechanism is configured for connection to a limb of a patient and for applying a distraction force to the limb of the patient; wherein the table mount is configured to transfer to the floor a force moment imposed on the table mount when the at least one distraction mechanism applies a distraction force to a limb of a patient; positioning the patient on the surgical table; connecting the limb of the patient to the at least one distraction mechanism; and applying a distraction force to the limb of the patient using the at least one distraction mechanism.

In another form of the invention, there is provided a distraction frame comprising: a table mount for fixation to a surgical table; at least one horizontal strut mounted to the table mount; at least one vertical strut mounted to the at least one horizontal strut; and at least one distraction mechanism mounted to the at least one vertical strut, wherein the at least one distraction mechanism is configured for connection to a limb of a patient and for applying a distraction force to the limb of the patient; wherein the table mount comprises a surface for selectively contacting the floor, and further wherein the table mount comprises at least one wheel for selectively supporting the surface of the table mount above the floor; and wherein the at least one horizontal strut comprises at least one caster for selectively rollably supporting the at least one horizontal strut on the floor, and further wherein the table mount comprises at least one foot peg for selectively supporting the at least one caster above the floor; such that (i) the distraction frame can be moved to the surgical table supported by the at least one wheel and the at least one caster, and (ii) the distraction frame can be fixed adjacent to the surgical table supported by the surface of the table mount and the at least one foot peg.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 14B is a schematic view showing a foot pedal mechanism which may be used in place of the adjustable supports of the table mount shown in FIGS. 3-14;

DETAILED DESCRIPTION OF THE PREFERRED EMBODIMENTS

The New and Improved Distraction Frame in General

The present invention provides a new and improved distraction frame for applying a distraction force to the leg of a patient so as to effect hip distraction.

Figure 1:
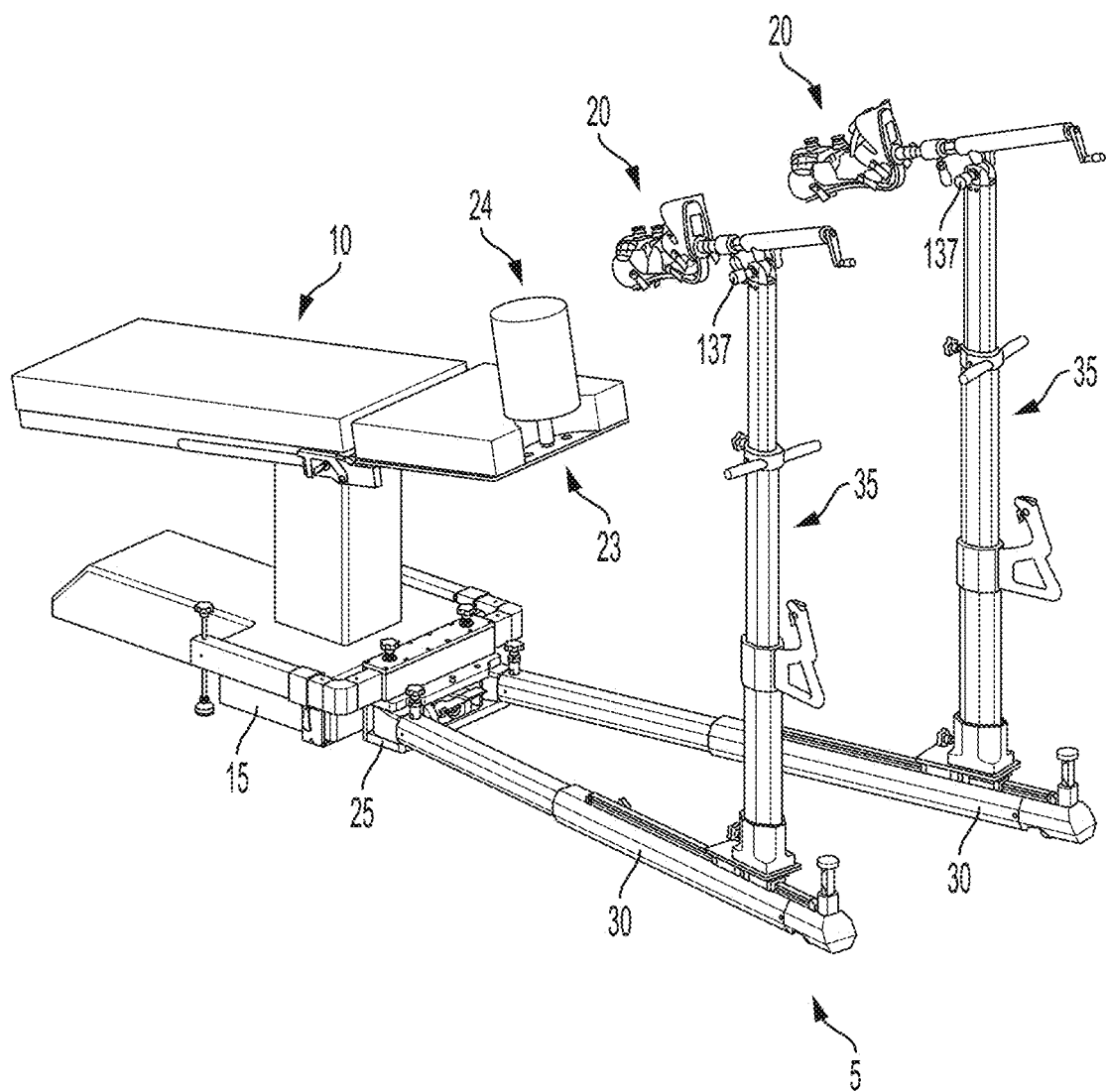
FIGS. 1 and 2 are schematic views showing a novel distraction frame formed in accordance with the present invention.
Figure 2:
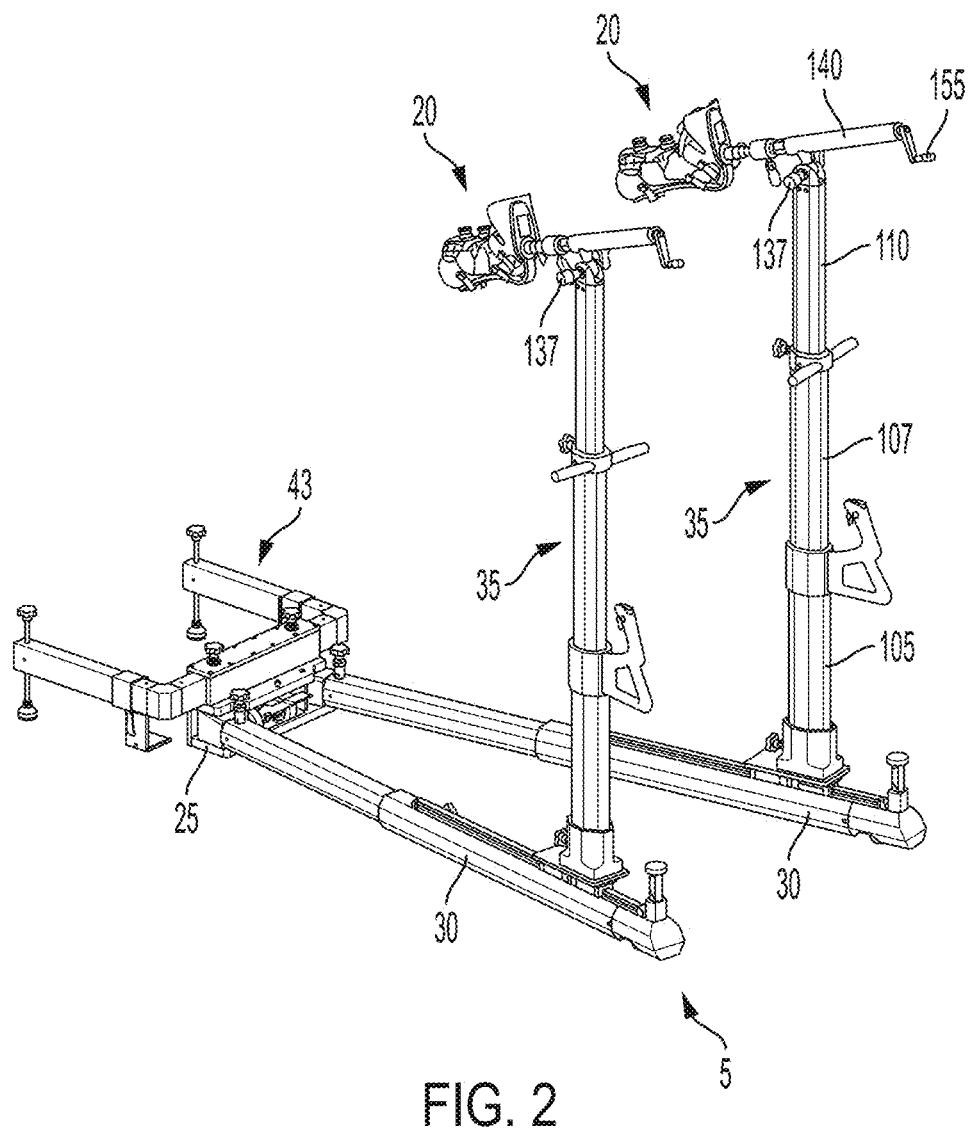
Figure 3:
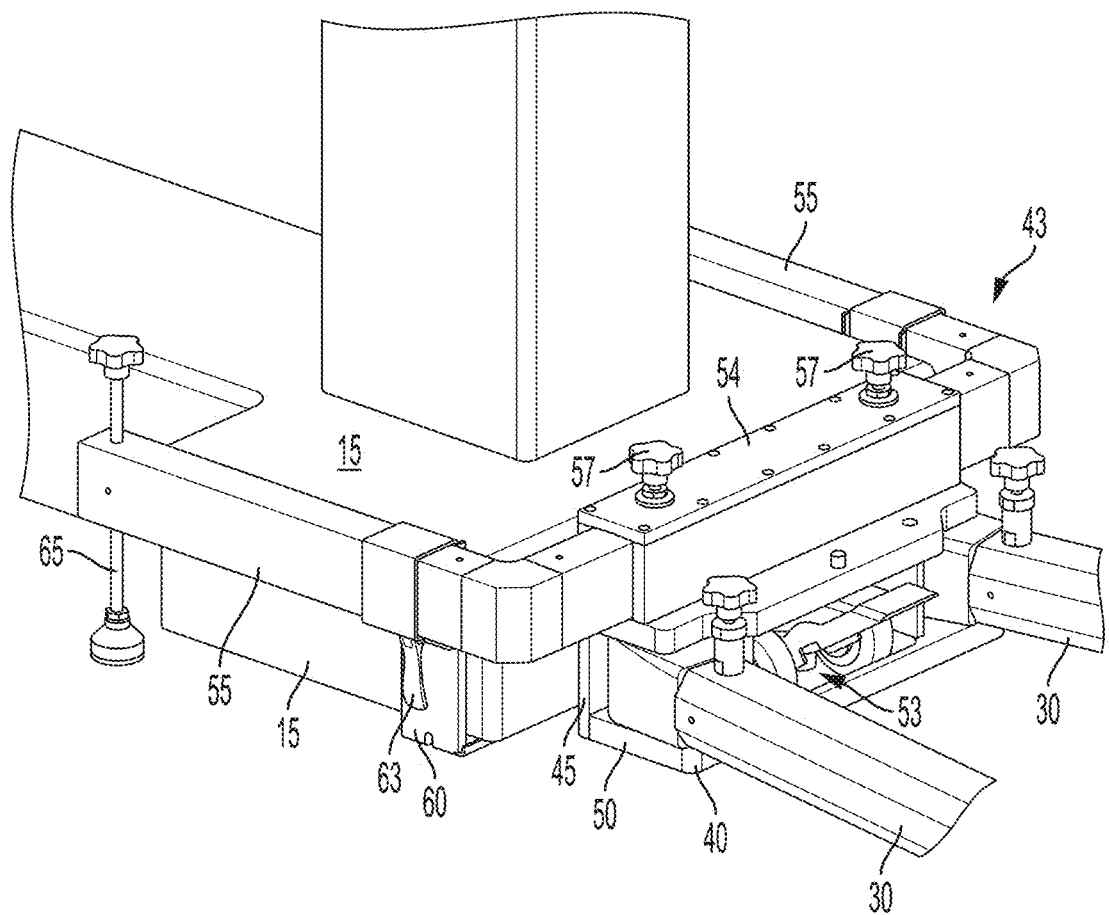
FIGS. 3-14 are schematic views showing details of the table mount of the novel distraction frame shown in FIGS. 1 and 2.
Figure 4:
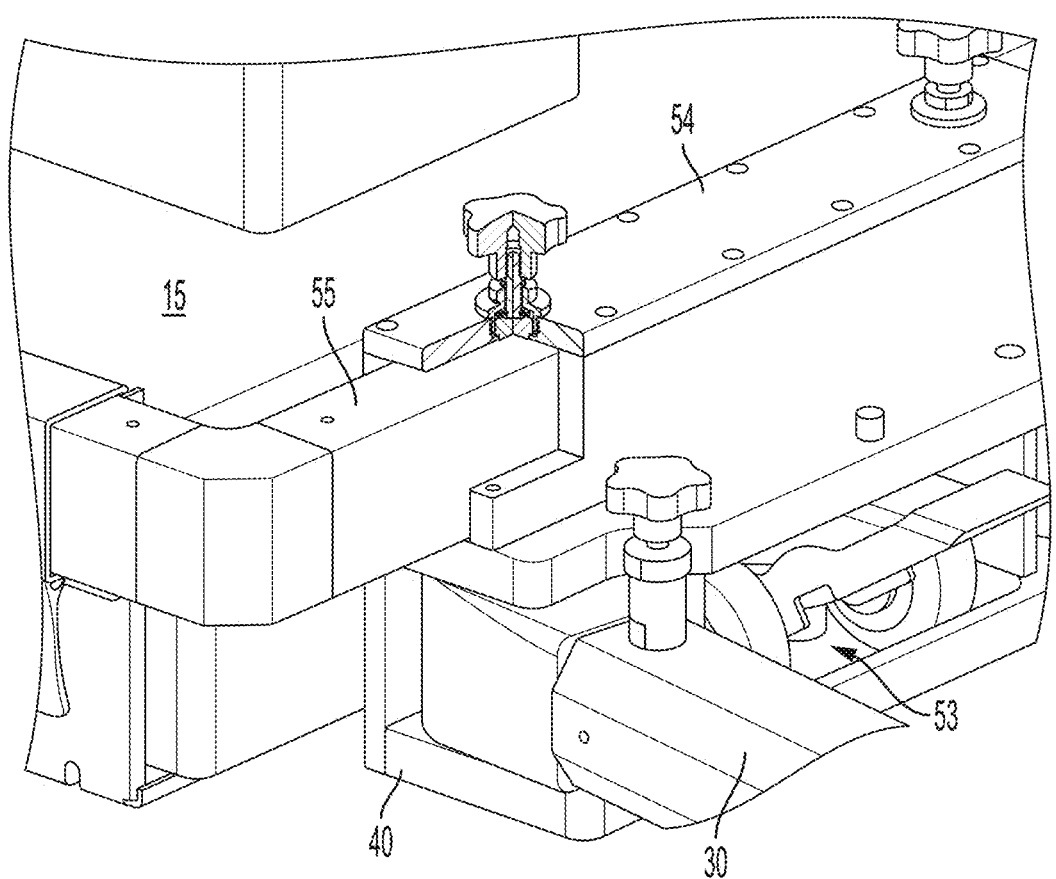

More particularly, and looking first at FIGS. 1 and 2, there is shown a novel distraction frame 5 formed in accordance with the present invention. Also shown in FIG. 1 is (i) a surgical table 10 for supporting a patient during surgery, wherein surgical table 10 comprises a base 15, and (ii) a pair of surgical boots 20 for disposition on the feet and lower legs of the patient. Surgical table 10 may be of the sort well known in the art. Surgical boots 20 may be the novel surgical boots shown in the aforementioned FIGS. 1 and 2 and described and illustrated in detail in U.S. Patent Application Ser. Nos. 62/455,154, 62/546,629, and Ser. No. 15/889,998, and/or surgical boots 20 may be conventional surgical boots of the sort well known in the art.

If desired, surgical table 10 may also comprise a novel table extender 23 which is configured to be mounted to the foot of surgical table 10, whereby to provide additional support for the patient during a surgical procedure. Novel table extender 23 is preferably substantially radiolucent, so that X-ray imaging can be conducted on anatomy supported by novel table extender 23. Novel table extender 23 is described and illustrated in detail in U.S. Patent Application Ser. Nos. 62/455,143, 62/546,600 and Ser. No. 15/890,047. If desired, table extender 23 may comprise a distraction post 24, which is the traditional means for facilitating hip distraction (e.g., by providing counter-traction to stabilize the patient on the surgical table and by levering the upper end of the leg of the patient against the distraction post so as to dislocate the femoral head from the acetabular cup). Such distraction posts are well known in the art of hip distraction.

Distraction frame 5 generally comprises a table mount 25, a pair of adjustable horizontal struts 30 and a pair of adjustable vertical struts 35.

Table Mount 25

Table mount 25 (FIGS. 1-14) generally comprises a body 40 and an extension assembly 43.

Body 40 generally comprises a vertical surface 45, a horizontal surface 50 and a recess 53.

Vertical surface 45 of body 40 is intended to sit adjacent to, but slightly spaced from, base 15 of surgical table 10. Alternatively, vertical surface 45 of body 40 may be in contact with base 15 of surgical table 10. Or, alternatively, vertical surface 45 of body 40 may be set a distance off base 15 of surgical table 10. Note that the ability to space vertical surface 45 of body 40 from base 15 of surgical table 10 can be advantageous, since it allows distraction frame 5 to work with a wide range of surgical tables.

Horizontal surface 50 of body 40 is intended to engage the operating room floor during hip distraction.

Recess 53 is intended to receive a retractable wheel assembly 205, wherein retractable wheel assembly 205 is configured for selectively (i) projecting out of recess 53 so as to engage the floor and movably support body 40 of table mount 25 above the floor, such that distraction frame 5 may be moved about a facility (for example, to move distraction frame 5 to another operating room or to a storage area), and (ii) retracting into recess 53 so as to disengage from the operating room floor and lower horizontal surface 50 of body 40 onto the operating room floor so as to prevent movement of distraction frame 5 (e.g., during a surgery).

In one preferred form of the invention, and looking now at FIGS. 1-12, retractable wheel assembly 205 generally comprises a mount 210 for mounting to body 40 of table mount 25 (FIGS. 6 and 8), and a base 215 movably mounted to mount 210. A spring 220 spring biases base 215 upward into the interior of mount 210. An axle 225, supporting wheels 230, passes through base 215. As a result of this construction, when base 215 moves upward and downward relative to mount 210, wheels 230 move upward and downward relative to body 40 of table mount 25.

An actuation lever 235, together with a linkage 240 and a bar 245, cooperate with a recess 250 (FIG. 11) on mount 210, such that stepping down on actuation lever 235 forces wheels 230 downward, whereby to engage the floor and raise up body 40 (and hence table mount 25) off of the floor, with bar 245 slipping into recess 250 so as to lock wheels 230 in their "down" position. Note that in this "down" position, table mount 25 is supported on wheels 230 such that distraction frame 5 may be moved about on a floor. A release lever 255, also connected to linkage 240 (FIG. 10), is provided for retracting wheels 230, i.e., by stepping down on release lever 255, linkage 240 moves bar 245 out of recess 250, thereby allowing wheels 230 to retract upwards off of the floor, and hence allowing body 40 to settle onto the floor (i.e., with horizontal surface 50 of body 40 engaging the floor).

Figure 7:
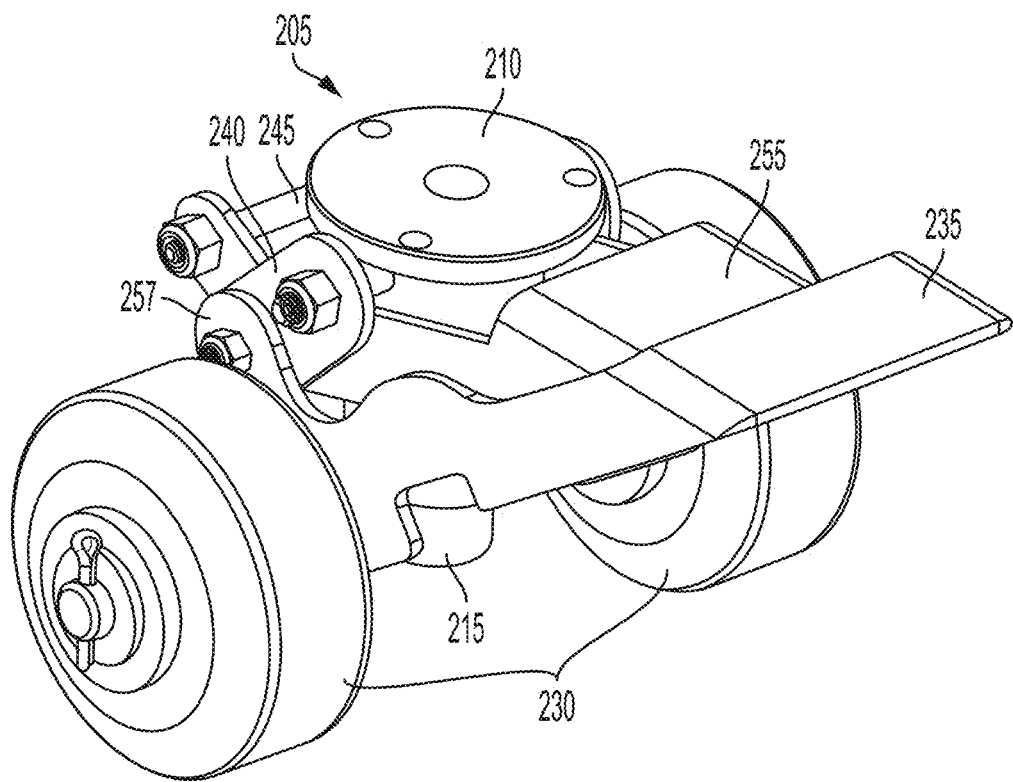
Figure 8:
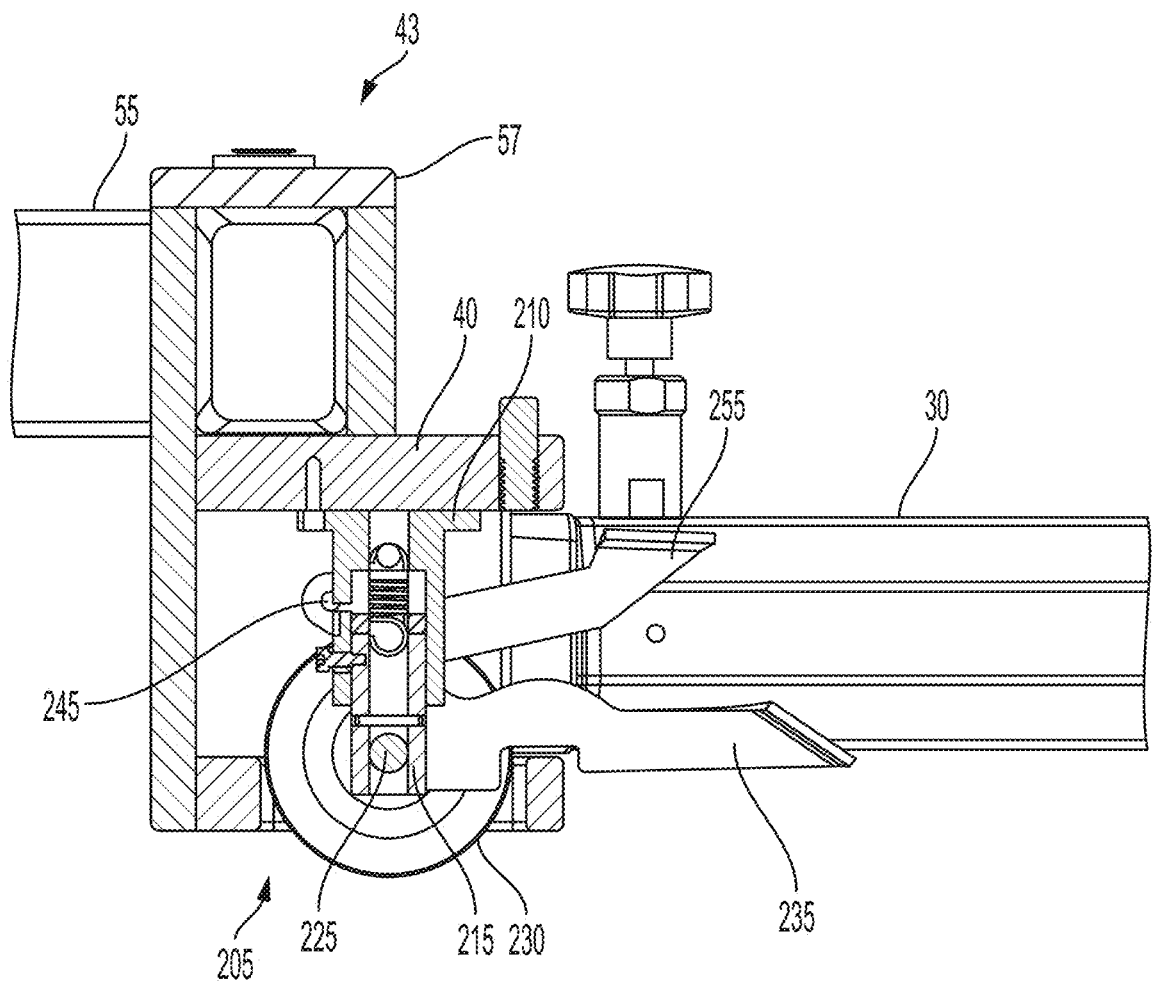
Figure 9:
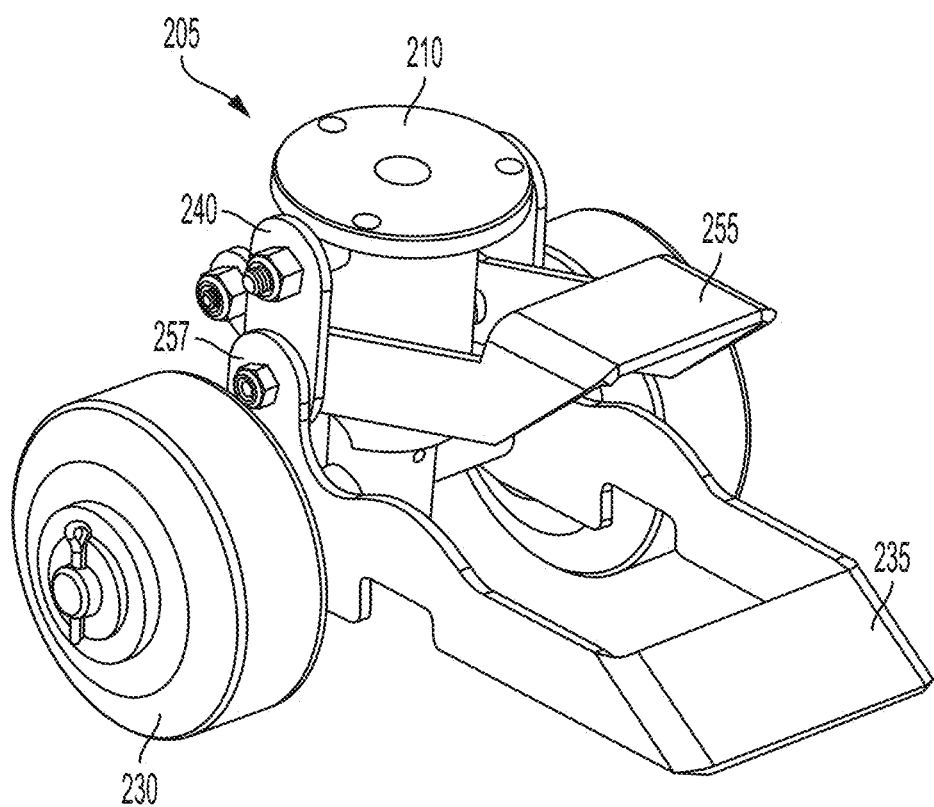
Figure 10:
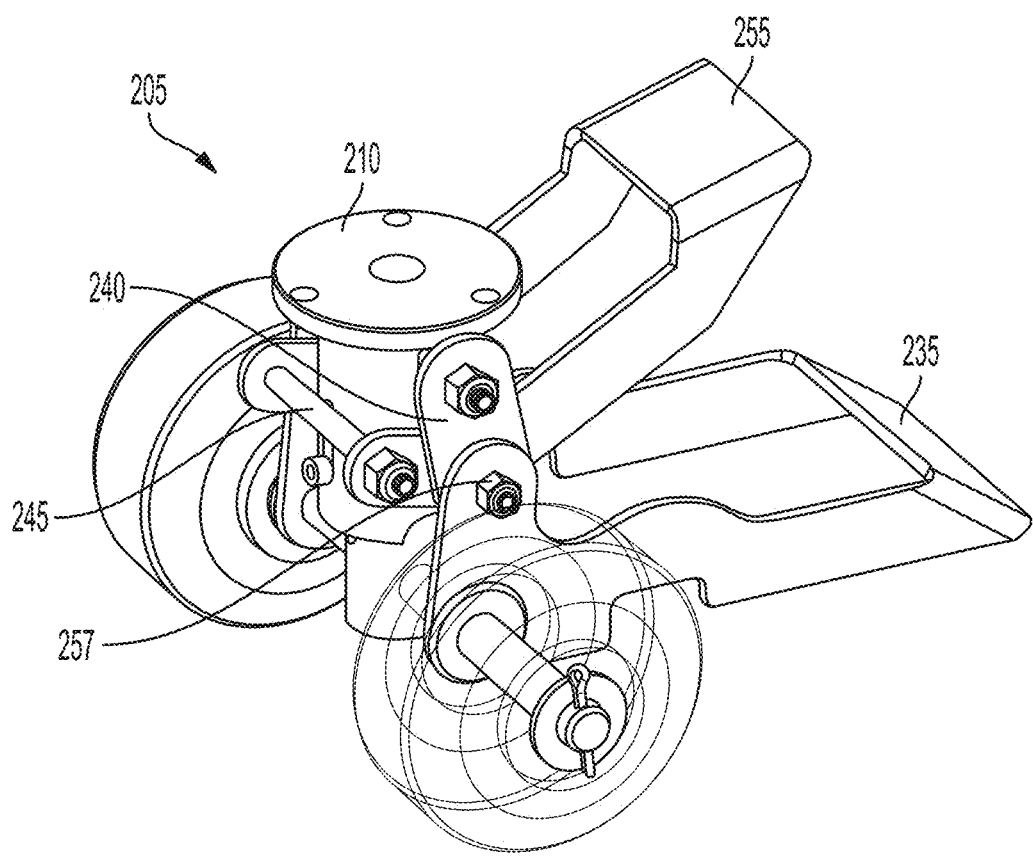
Figure 11:
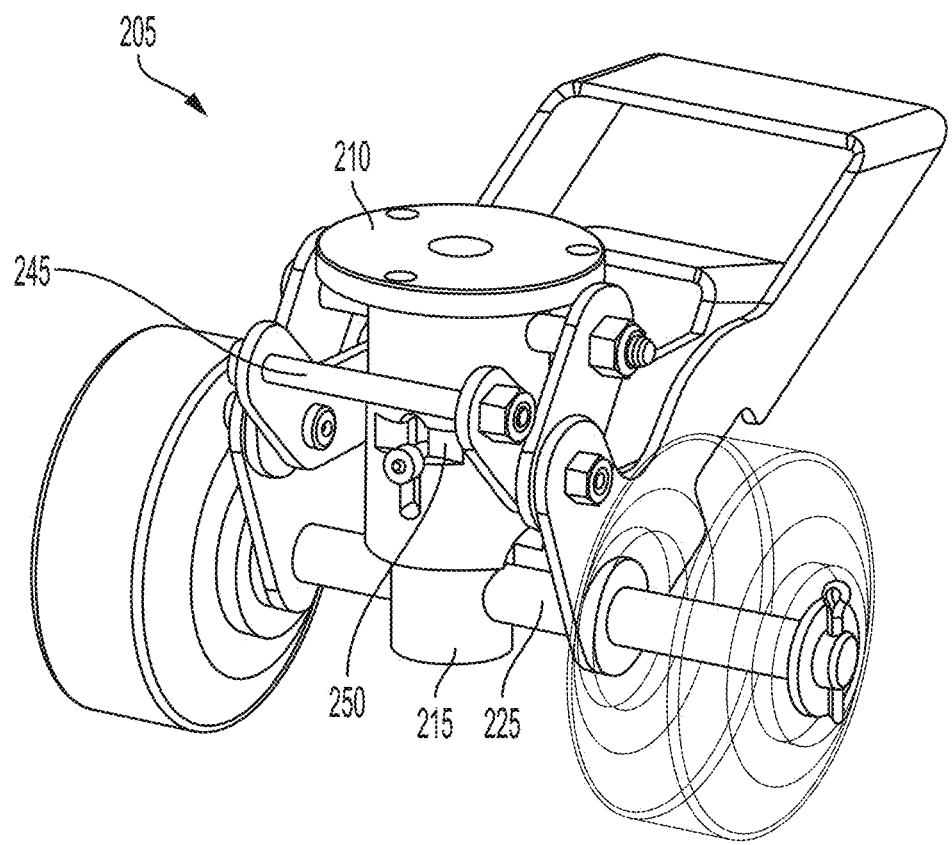
Figure 12:
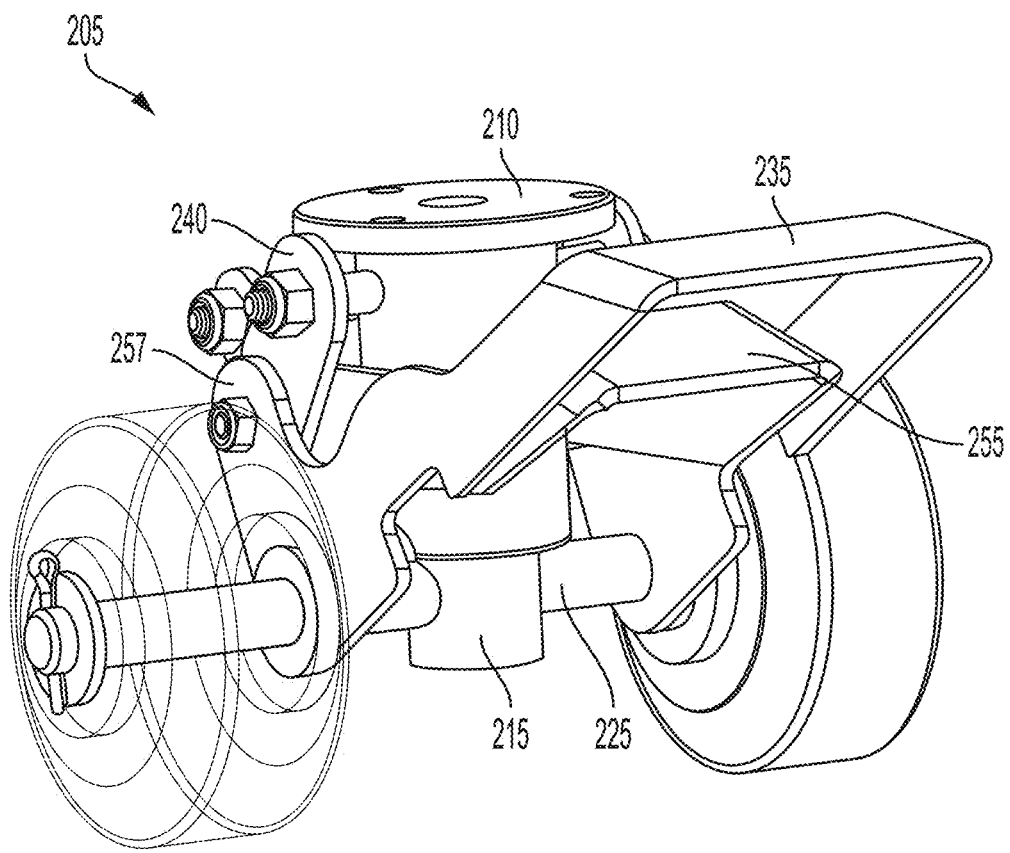
Figure 13:
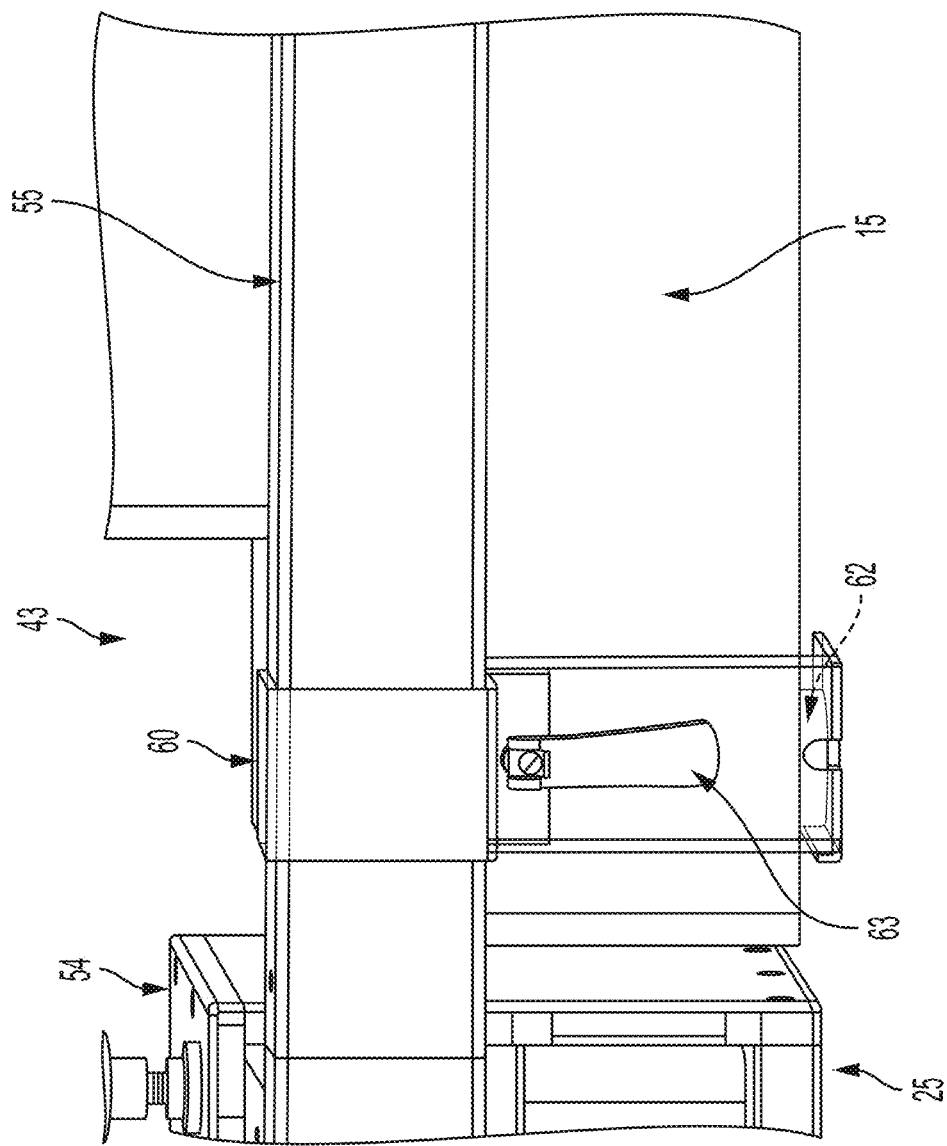

Note that when wheels 230 are in their "retracted" position (FIG. 6), the arm 257 (FIG. 12) of actuation lever 235 and linkage 240 project "off-center" towards bar 245 (FIG. 7), and when wheels 230 are in their "down" position, with bar 245 slipped into recess 250, arm 257 of actuation lever 235 and linkage 240 project "off-center" away from bar 245 (FIG. 10). Note also that when release lever 255 is to be used for retracting wheels 230, release lever 255 essentially moves linkage 240 "over center", from its "off-center" position away from bar 245 (FIG. 10) towards its "off-center" position towards bar 245 (FIG. 7). Once release lever 255 moves linkage 240 "over center", the weight of the structure(s) being supported by wheels 230 (e.g., the weight of distraction frame 5) provides the major force for retracting wheels 230 into recess 53.

It will be appreciated that, in view of the foregoing construction, (i) stepping down on actuation lever 235 locks wheels 230 in their "down" position, so that table mount 25 is movably supported on wheels 230, and (ii) stepping down on release lever 255 retracts wheels 230 into recess 53 of body 40, whereby to allow horizontal surface 50 of body 40 to seat on the operating room floor.

In an alternative embodiment, retractable wheel assembly 205 may comprise a single-pedal mechanism of the sort well known in the art of material transport, with the single-pedal mechanism alternately moving wheels 230 between their upward and downward positions.

Recess 53 also serves to receive the proximal ends of adjustable horizontal struts 30 as will hereinafter be discussed.

Extension assembly 43 (FIGS. 3, 6, 8, 13 and 14) comprises a mount 54 which is mounted to body 40, and a pair of L-shaped extensions 55 which extend away from mount 54 (and which extend away from body 40). L-shaped extensions 55 are intended to extend on either side of base 15 of surgical table 10. Thus, L-shaped extensions 55 essentially constitute "outriggers" which extend on either side of base 15 of surgical table 10. Mount 54 (and hence L-shaped extensions 55) is secured to body 40. L-shaped extensions 55 are adjustably secured to mount 54 with clamps 57 (FIG. 3), i.e., so that L-shaped extensions 55 are laterally adjustably securable relative to mount 54 (and hence body 40). Thus, the laterally-adjustable L-shaped extensions 55 essentially constitute laterally-adjustable outriggers which extend on either side of base 15 of surgical table 10. Note that laterally adjustably securing L-shaped extensions 55 to mount 54 is advantageous, since it allows distraction frame 5 to accommodate different widths of bases 15 of surgical tables 10, i.e., by allowing the outriggers (i.e., L-shaped extensions 55) to be laterally adjusted so as to straddle bases 15 of different widths. Although clamps 57 are shown in the figures as extending with a vertical orientation, clamps 57 could also be mounted to the side of mount 54 so that they extend with a horizontal orientation.

A pair of L-shaped brackets 60 are slidably mounted to L-shaped extensions 55 and extend under base 15 of surgical table 10 so that the lower ends of L-shaped brackets 60 may be captured beneath table feet 62 (FIGS. 13 and 14) of surgical table 10 (surgical tables 10 typically comprise rollers and retractable/extendable table feet, with the table feet being retracted so that the surgical tables are able to move on their rollers when the surgical tables are to be moved about a floor, and with the table feet being extended when the surgical tables are to be fixed in position on a floor). More particularly, L-shaped brackets 60 are slidable along extensions 55 so that L-shaped brackets 60 may be positioned beneath table feet 62 when the table feet are in their retracted position, and L-shaped brackets 60 each comprise a latch 63 for locking L-shaped brackets 60 in position along L-shaped extensions 55 (FIGS. 13 and 14) when L-shaped brackets 60 are to be captured under the table feet when the table feet are extended to the floor. Positioning L-shaped brackets 60 under table feet 62 of surgical table 10 effectively holds distraction frame 5 in a fixed position relative to surgical table 10 by using the weight of surgical table 10 on L-shaped brackets 60. Thus, with the present invention, distraction frame 5 does not need to be bolted to, or clamped to, surgical table 10 in order to effectively hold distraction frame 5 in a fixed position relative to surgical table 10. This is a substantial advantage over prior art distraction frames.

Alternative constructions can include L-shaped extensions 55 of different lengths or of different cross-sectional shapes and sizes. L-shaped brackets 60 may be similarly varied in construction, for instance, they may not necessarily be positioned under table feet 62 of base 15 of surgical table 10, but may engage elsewhere under base 15 of surgical table 10 so as to achieve the same engagement between the floor, L-shaped extensions 55 and base 15 of surgical table 10 (i.e., with L-shaped extensions 55 being captured to the floor by base 15 of surgical table 10). By way of example but not limitation, L-shaped brackets 60 may be captured beneath another portion of base 15 of surgical table 10. Note that L-shaped brackets 60 may also have a height adjustment feature so that the vertical distance between (i) the portion of the L-shaped bracket which is mounted to the L-shaped extensions 55, and (ii) the portion of the L-shaped bracket which mounts to the surgical table 10, can be varied. This feature can accommodate uneven floors where the distance between each of the L-shaped extensions 55 and the floor may vary.

A pair of adjustable supports 65 (FIG. 14) are mounted to L-shaped extensions 55 and also engage the floor upon which surgical table 10 sits. Adjustable supports 65 are preferably positioned at the ends of L-shaped extensions 55 which are opposite to body 40, however, adjustable supports 65 may alternatively be located anywhere along the length of L-shaped extensions 55, possibly with the overall length of L-shaped extensions 55 varying. Adjustable supports 65 preferably comprise a threaded engagement with L-shaped extensions 55, and preferably further comprise a locking nut 66 (FIG. 14) to lock adjustable supports 65 relative to L-shaped extensions 55 once adjustable supports 65 are in their desired positions.

Figure 14:
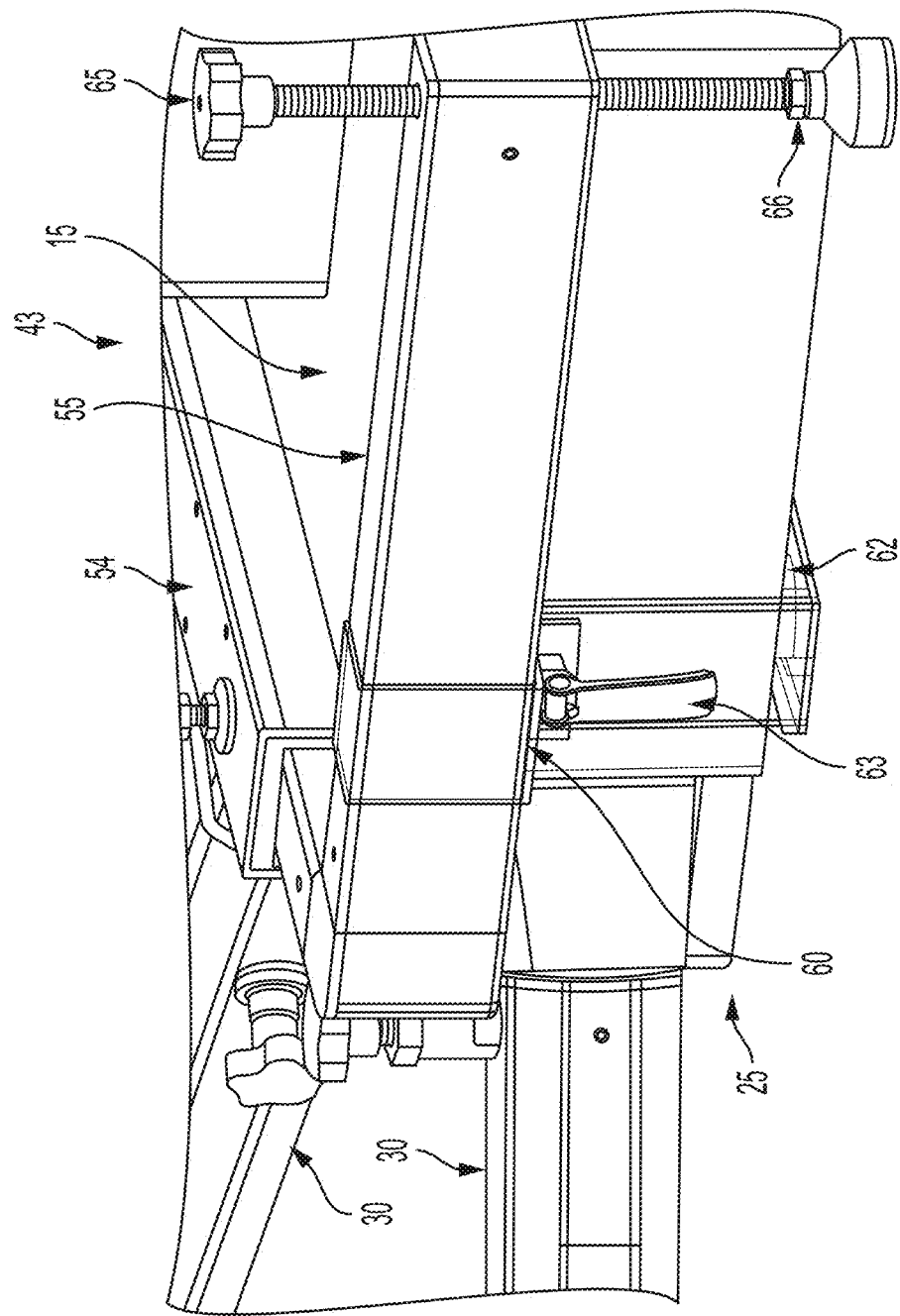
Figure 14A:
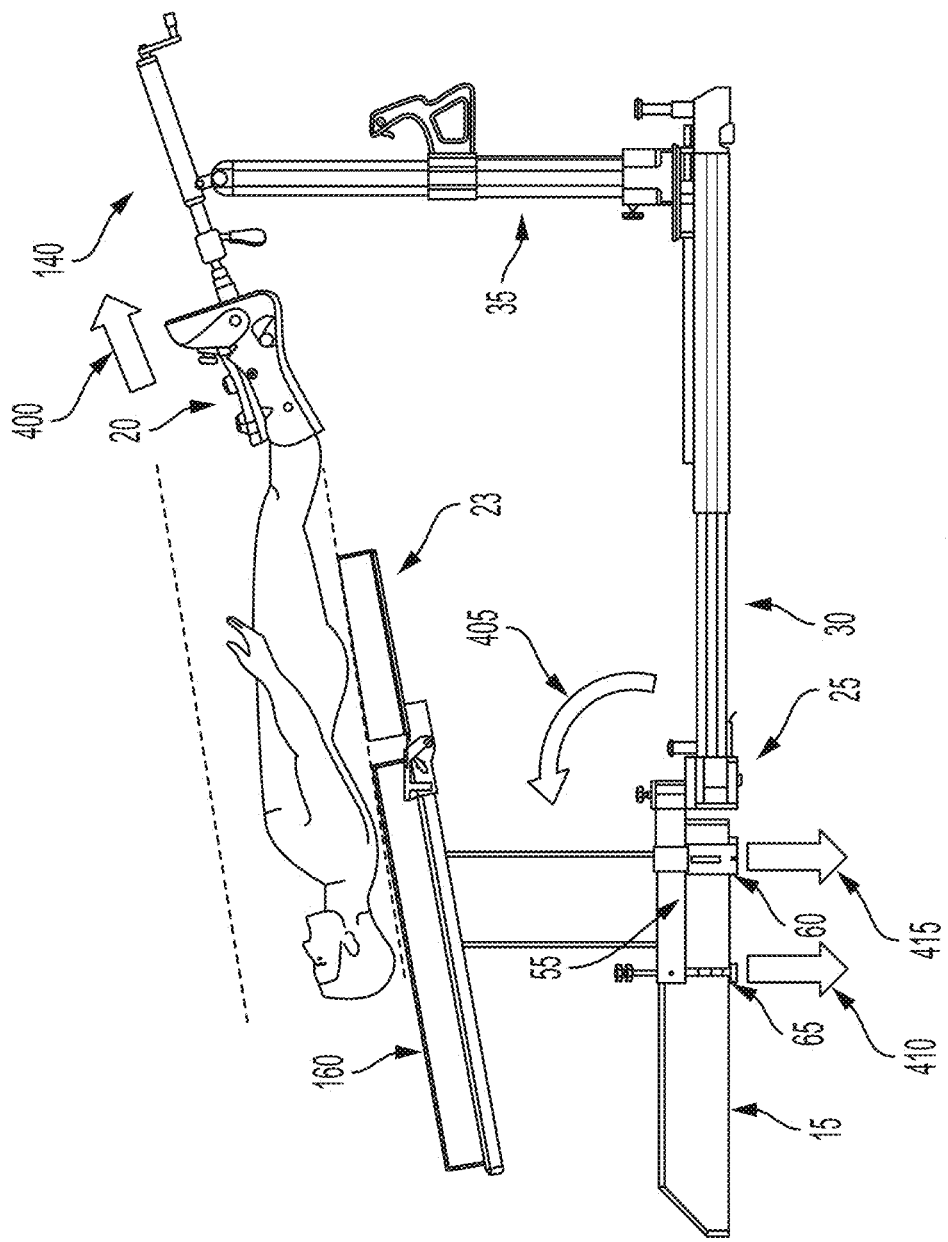
FIG. 14A is a schematic view showing how a distraction force applied to the leg of a patient creates a force moment at the table mount which is transferred to the operating room floor.

It will be appreciated that, on account of the foregoing construction, when table mount 25 of distraction frame 5 is mounted to base 15 of surgical table 10 (e.g., by way of L-shaped brackets 60 being captured under table feet 62 of base 15 of surgical table 10, and by adjustable supports 65 being positioned securely against the floor), and distraction frame 5 is thereafter used to apply a distraction force to the leg of a patient (e.g., via adjustable horizontal struts 30, adjustable vertical struts 35, etc.), any force moment produced at table mount 25 will be to transferred to the operating room floor via L-shaped extensions 55 and adjustable supports 65, and via L-shaped extensions 55 and L-shaped brackets 60. See, for example, FIG. 14A, which shows how a distraction force 400 applied to the leg of a patient creates a force moment 405 at table mount 25 which is transferred to the operating room floor as a force 410 via L-shaped extension 55 and adjustable supports 65, and as a force 415 via L-shaped extensions 55 and L-shaped brackets 60. This is highly advantageous since the force moments are transferred to the operating room floor and are not imposed on any mechanical connections between the distraction frame and the surgical table. Indeed, as noted above, the construction of the distraction frame of the present invention does not need to create a mechanical connection with the surgical table, the distraction frame of the present invention simply has its L-shaped brackets 60 clamped beneath table feet 62 of surgical table 10.

Note that modifications to the materials of construction, or to the configuration of the design elements (e.g., L-shaped brackets 60, adjustable supports 65, etc.) may be made to alter the stiffness and performance of distraction frame 5 while still maintaining the same overall design to transfer the patient distraction forces to the floor of the operating room. For example, although adjustable supports 65 are generally shown in the figures as having a threaded adjustment, adjustable supports 65 could also be actuated (e.g., raised and lowered, and locked in place) with a foot pedal mechanism (see, for example, the foot pedal mechanism 67 shown in FIG. 14B). In this alternative construction, foot pedal mechanism 67 may comprise a mechanism generally similar to the retractable foot pegs 97 discussed below.

Adjustable Horizontal Struts 30

Figure 15:
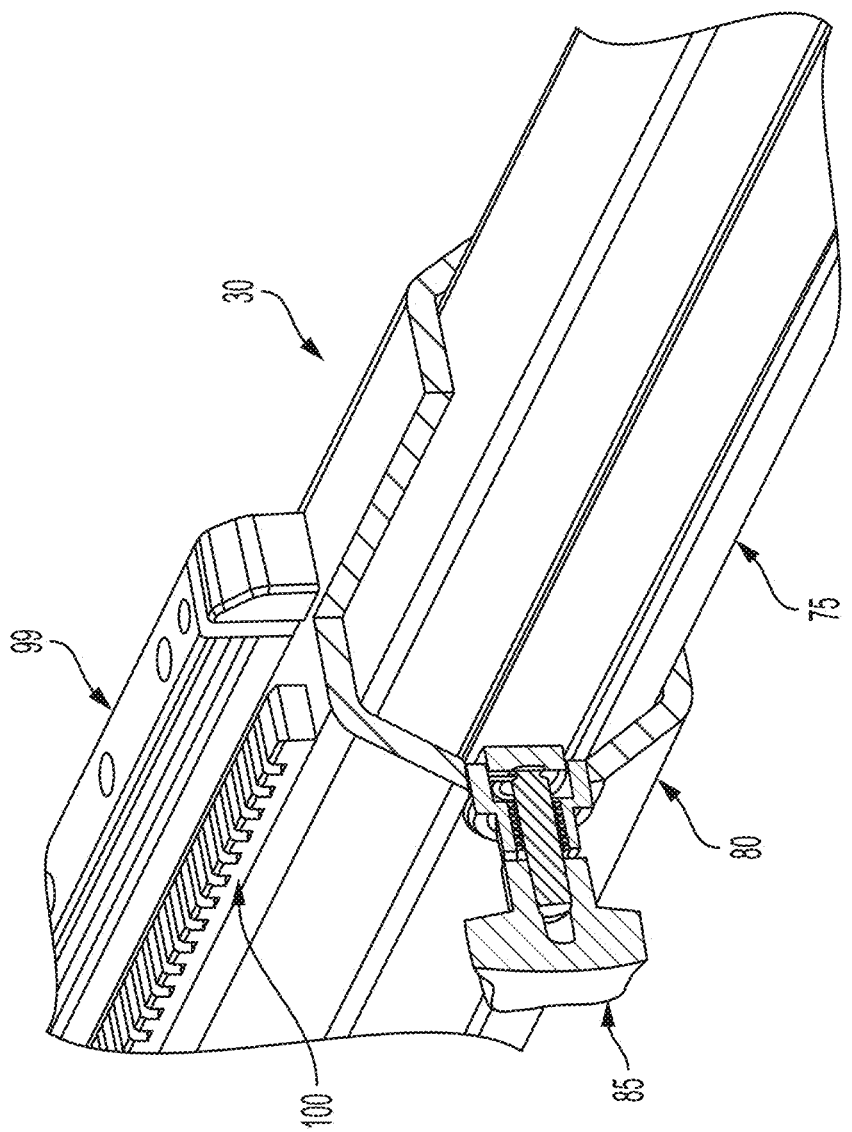
FIGS. 15, 15A-15C, 16-21, 21A-21C and 22-27 are schematic views showing details of the adjustable horizontal struts, the adjustable vertical struts, and elements attached to these struts, of the novel distraction frame shown in FIGS. 1 and 2.
Figure 15A:
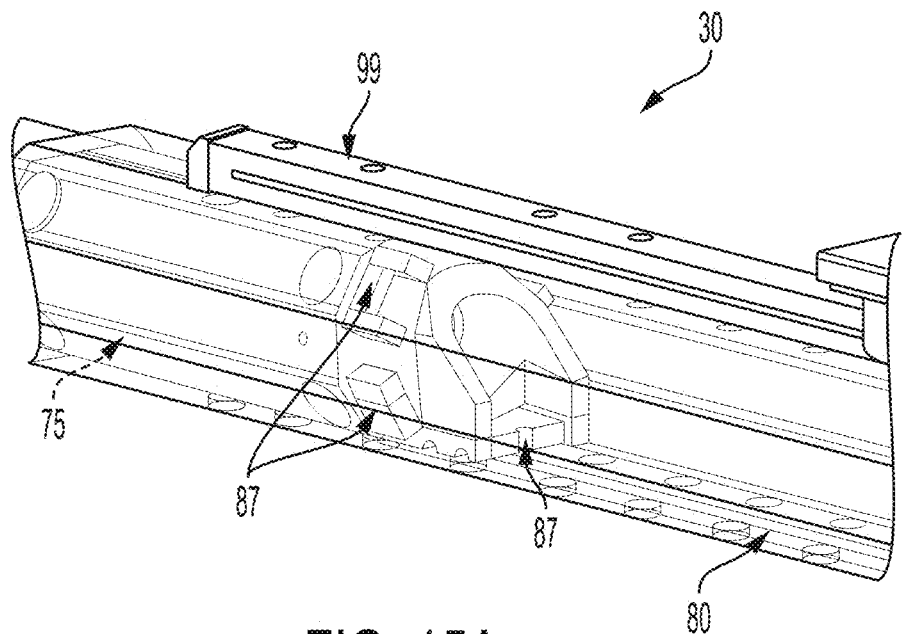
Figure 15B:
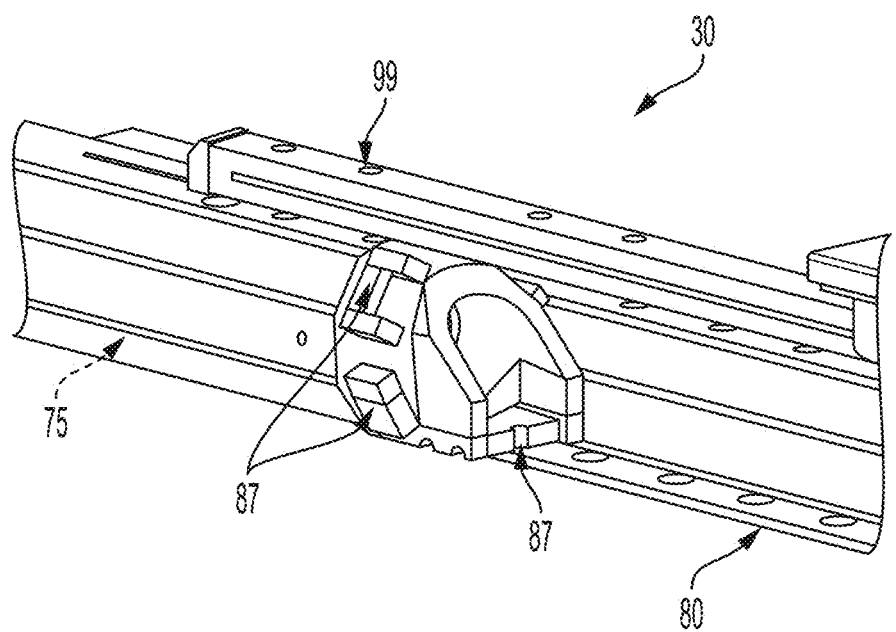
Figure 15C:
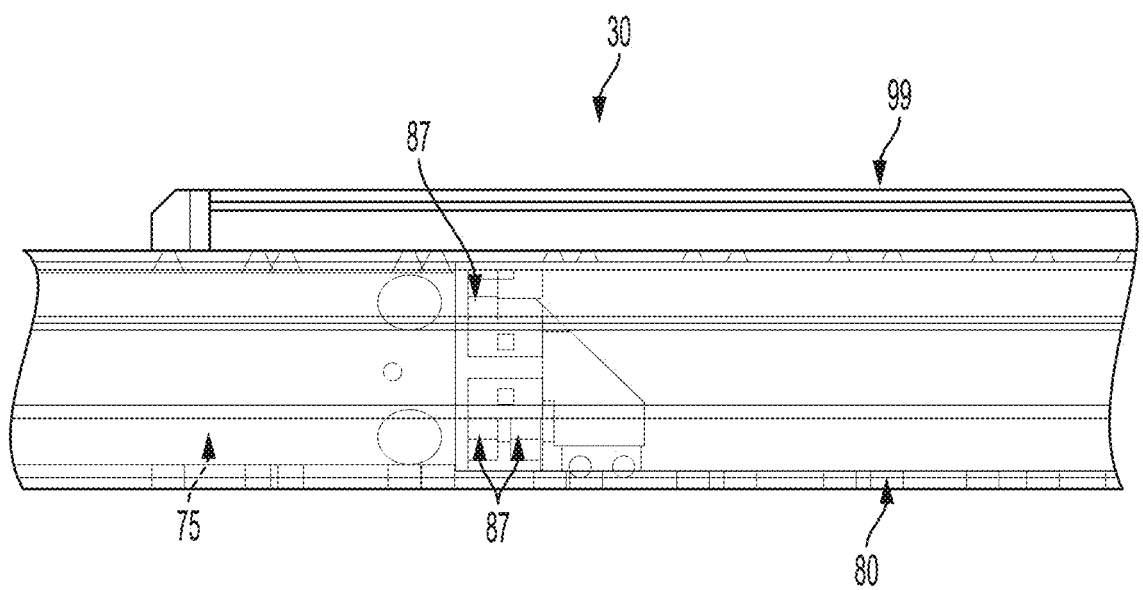
Figure 16:
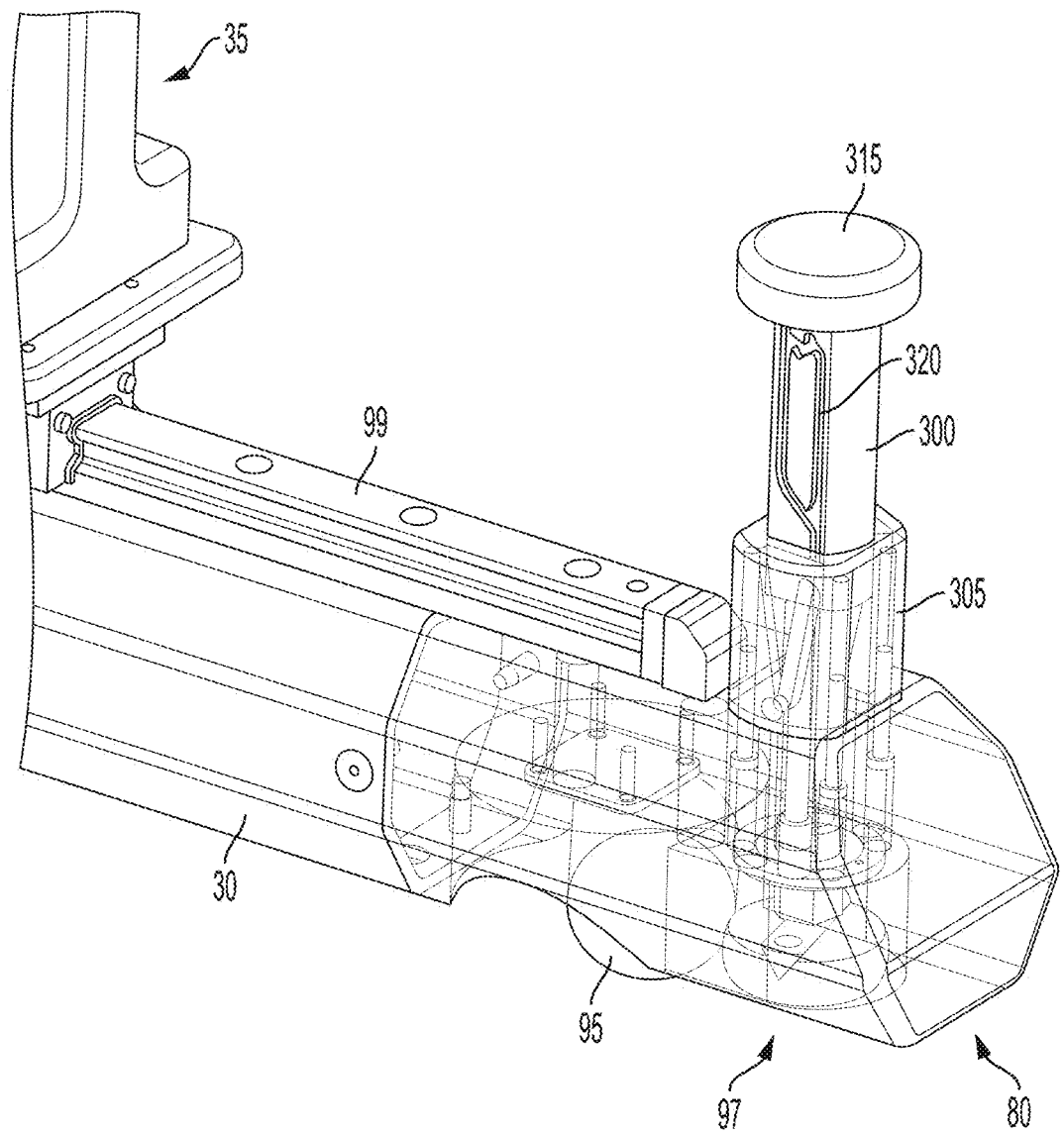
Figure 17:
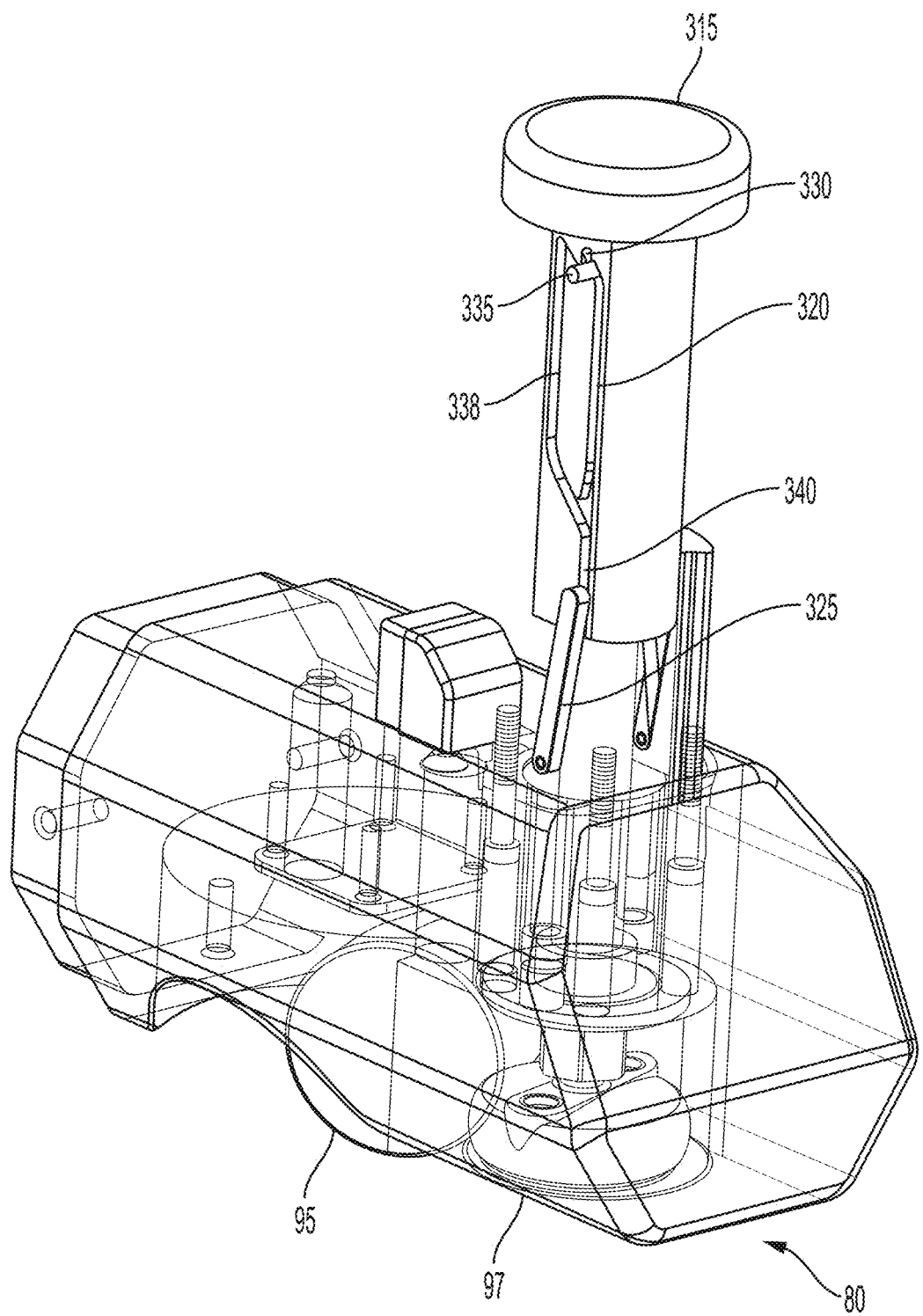
Figure 18:
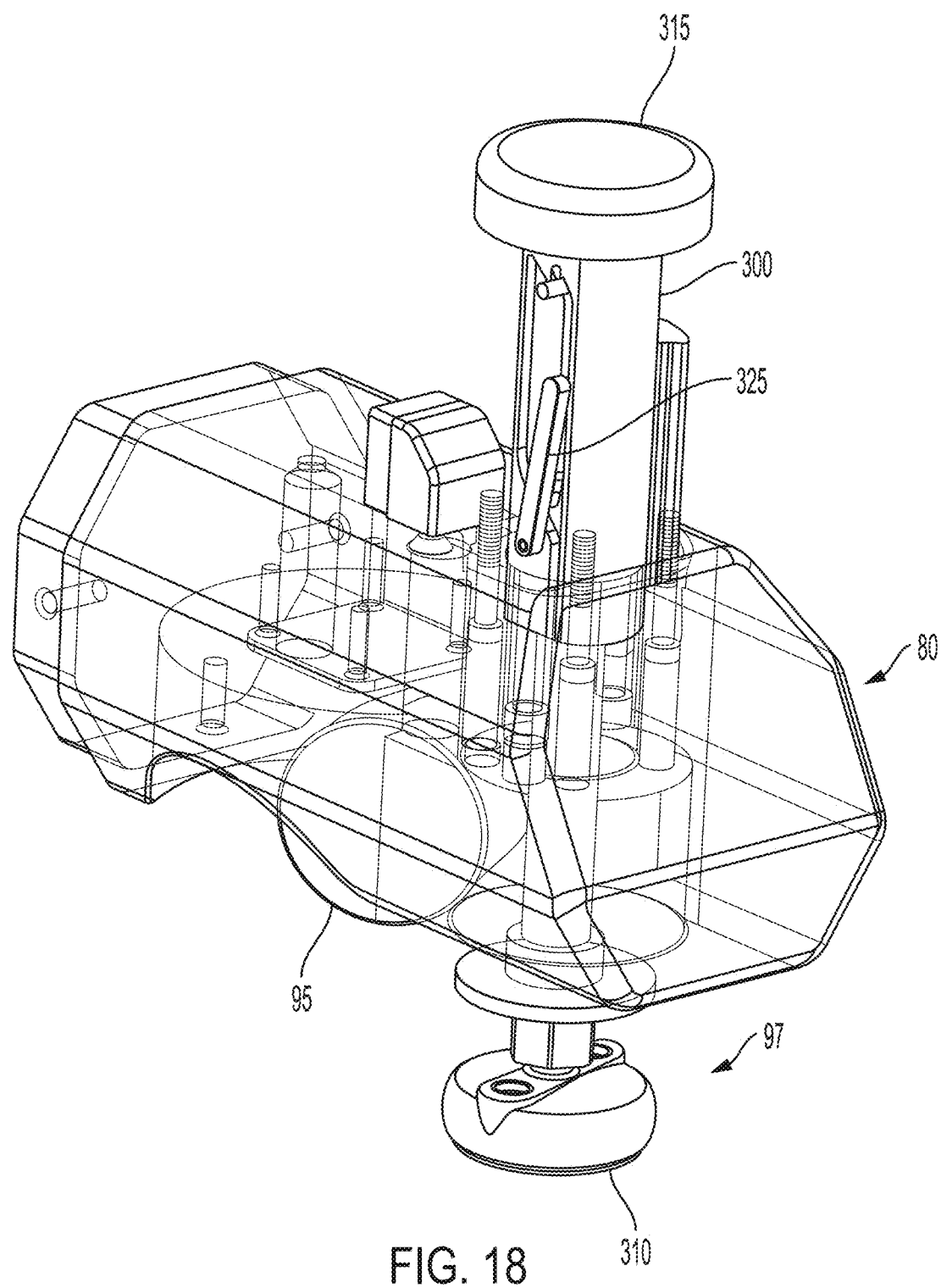
Figure 19:
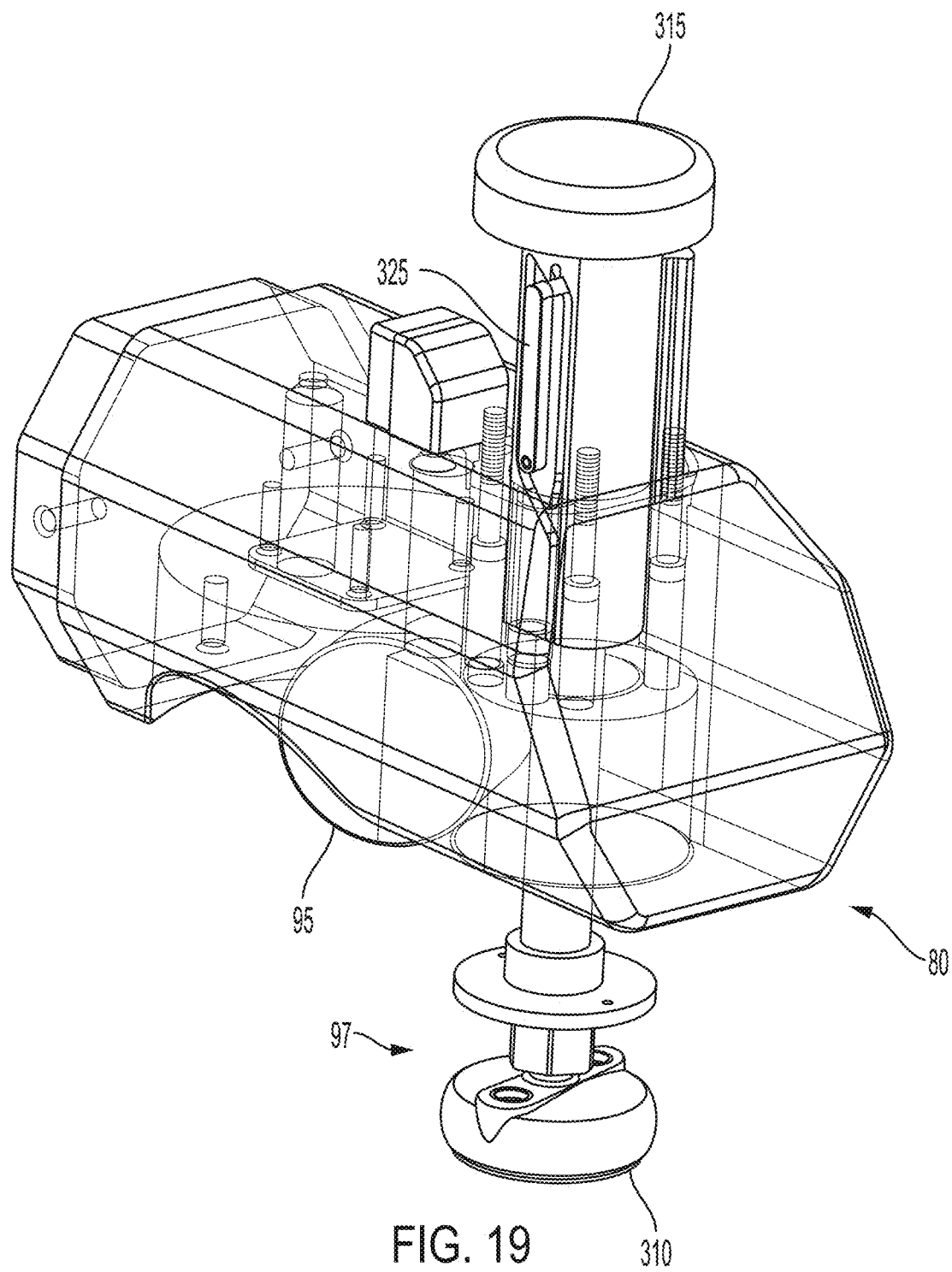
Figure 20:
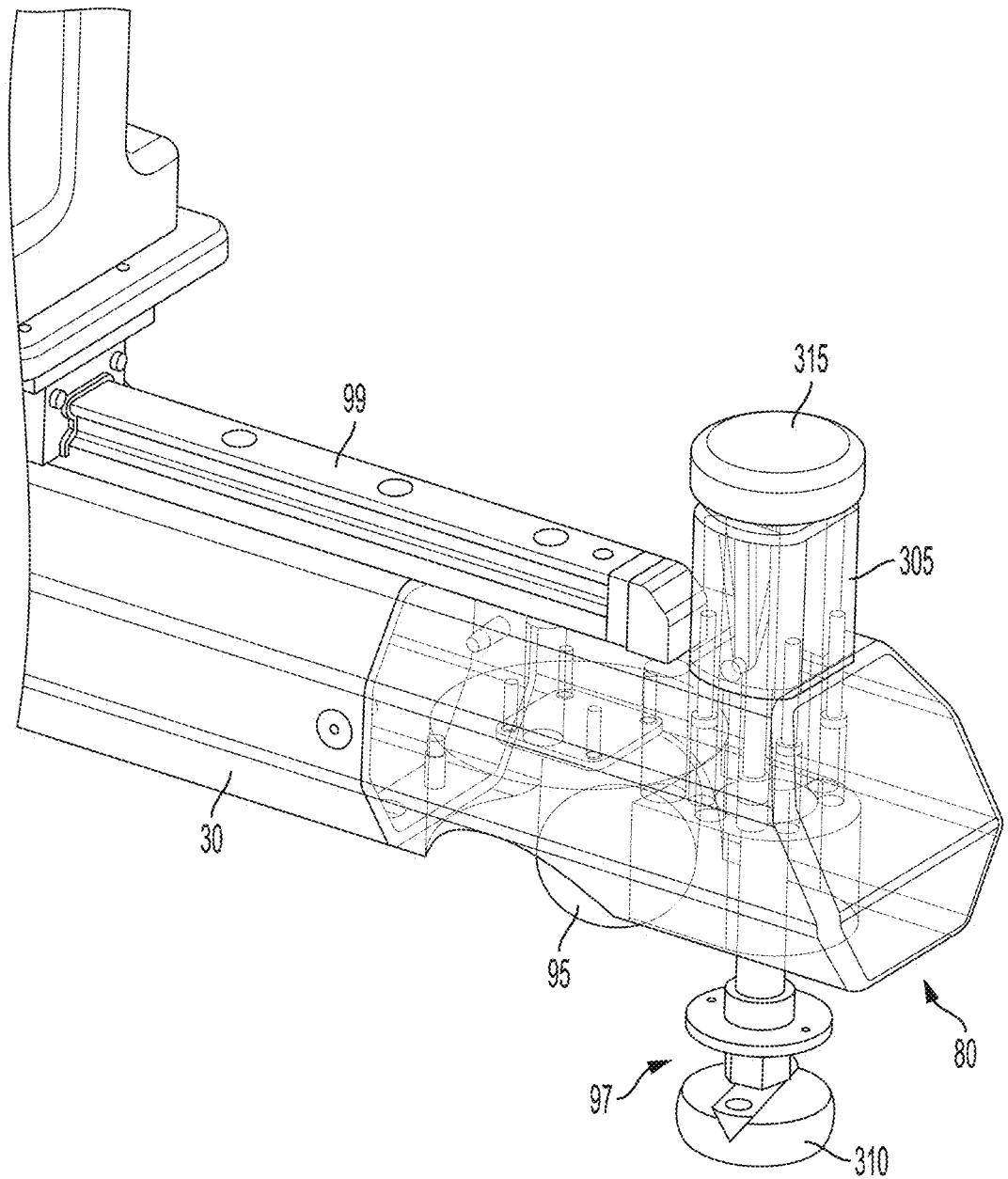
Figure 21:
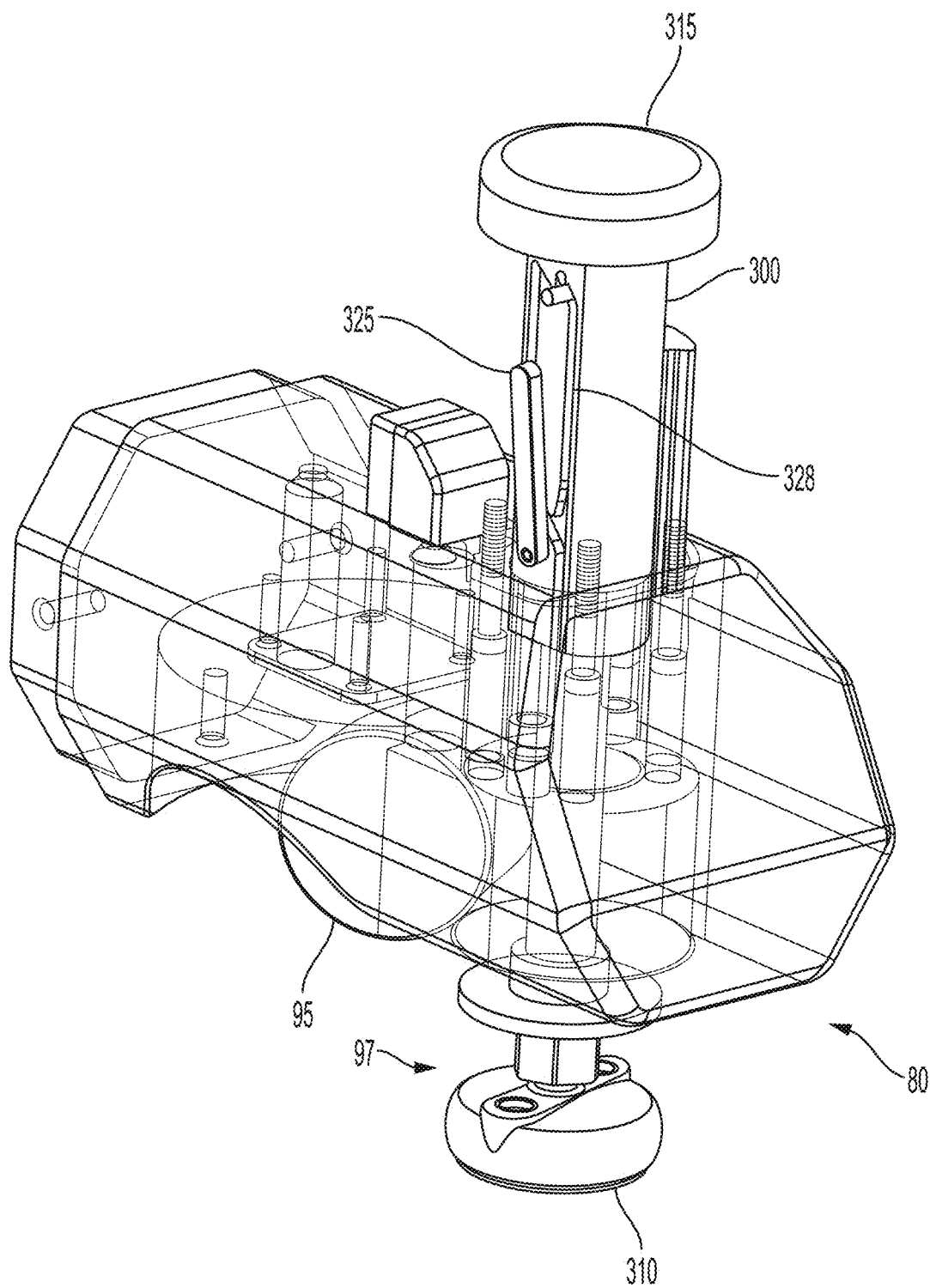
Figure 21A:
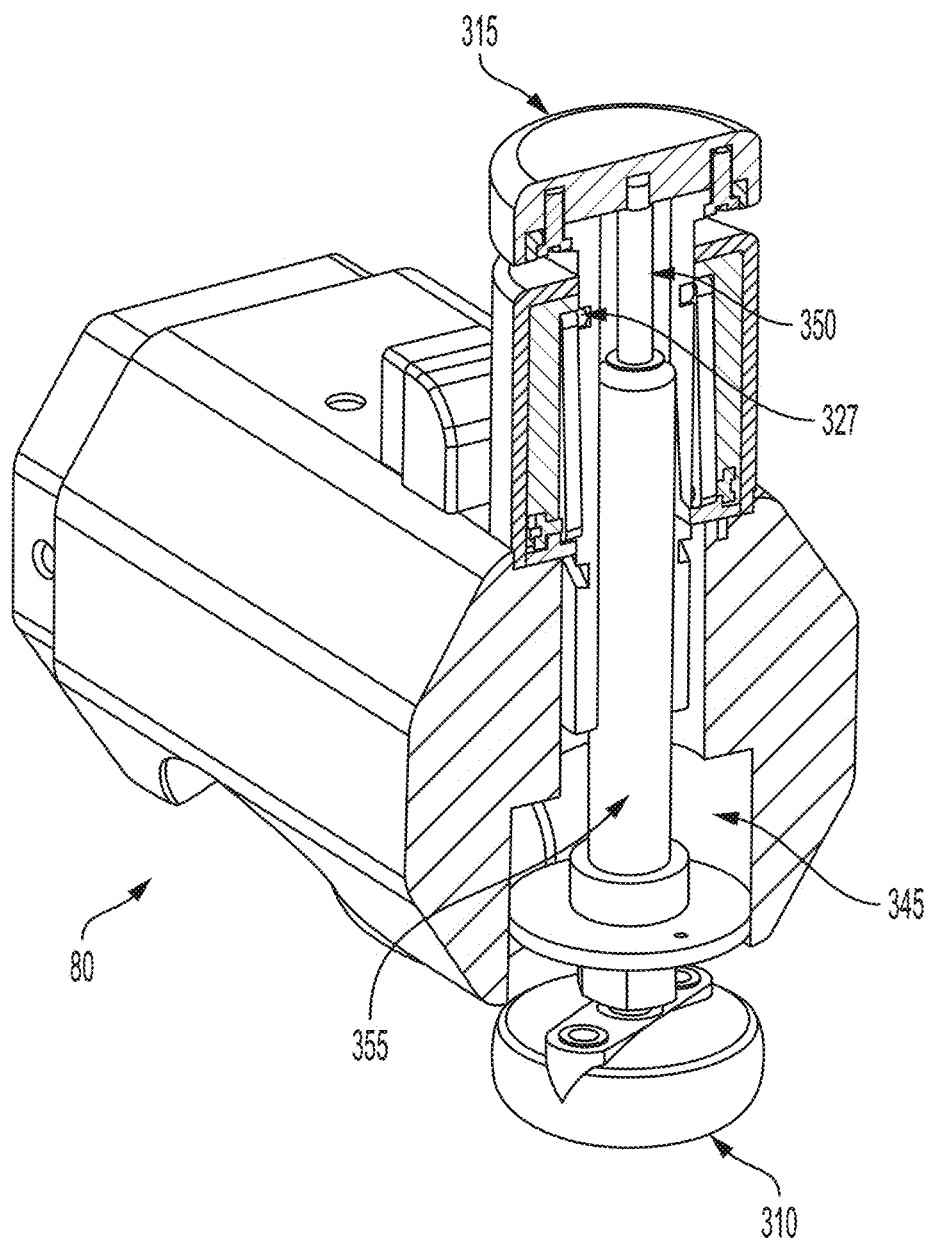
Figure 21B:
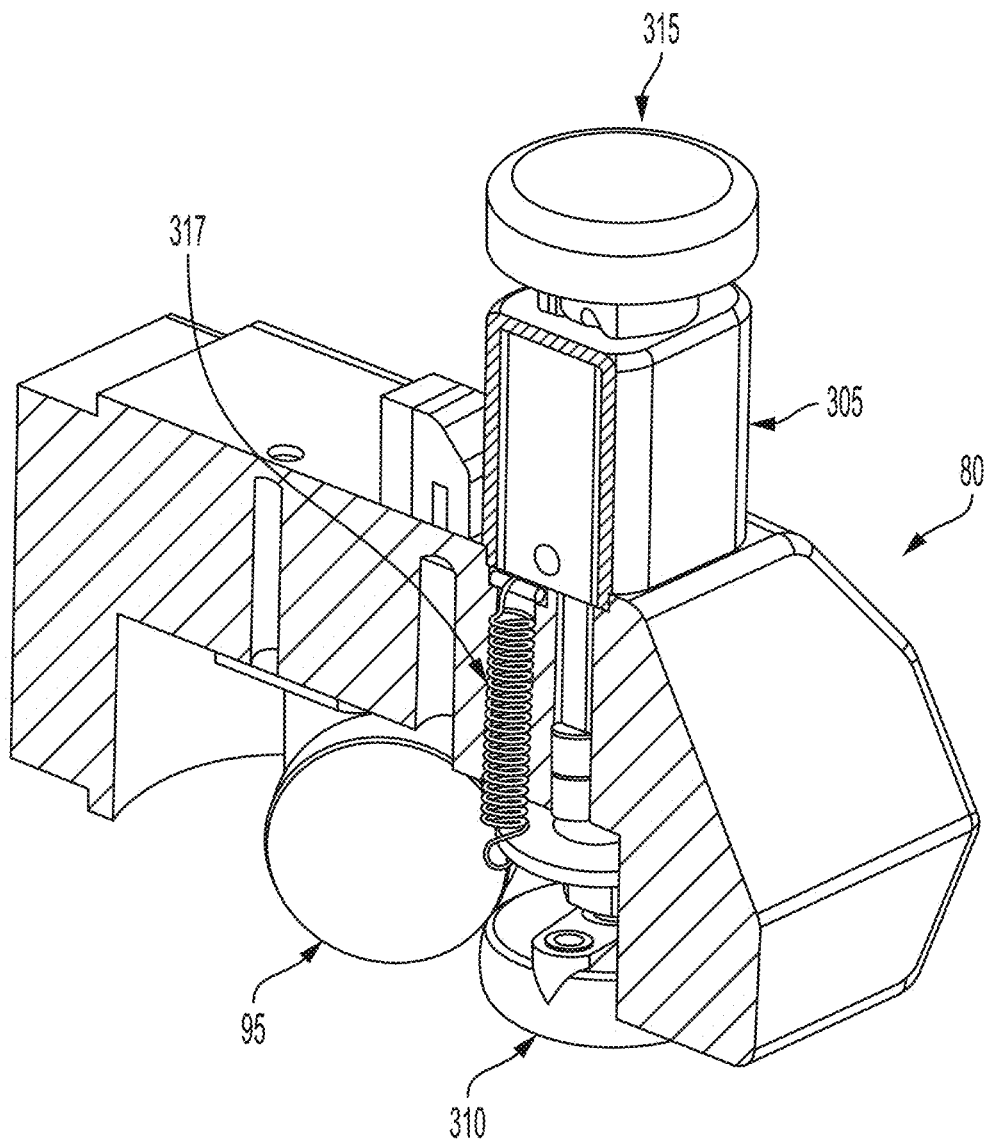
Figure 21C:
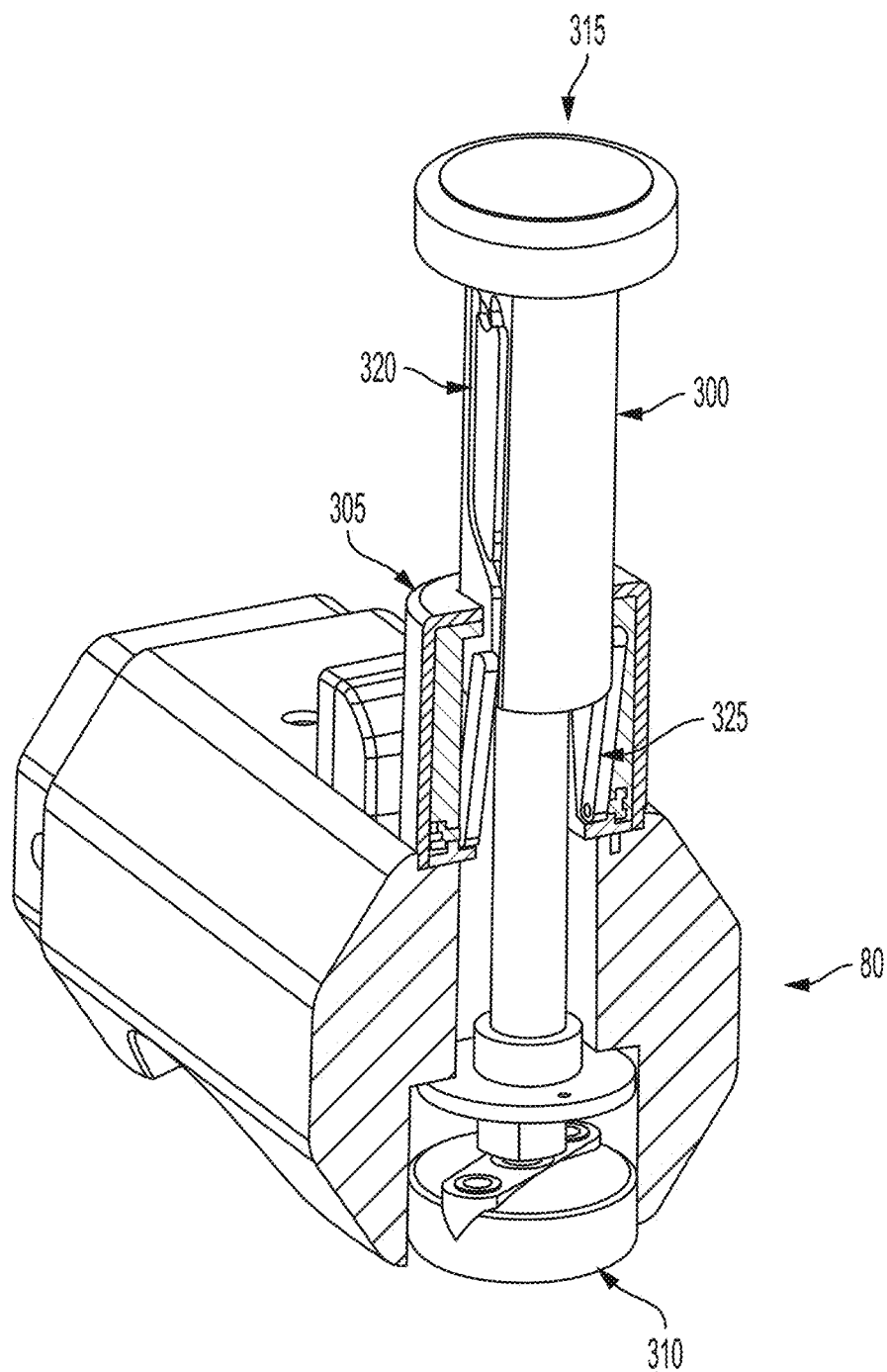
Figure 22:
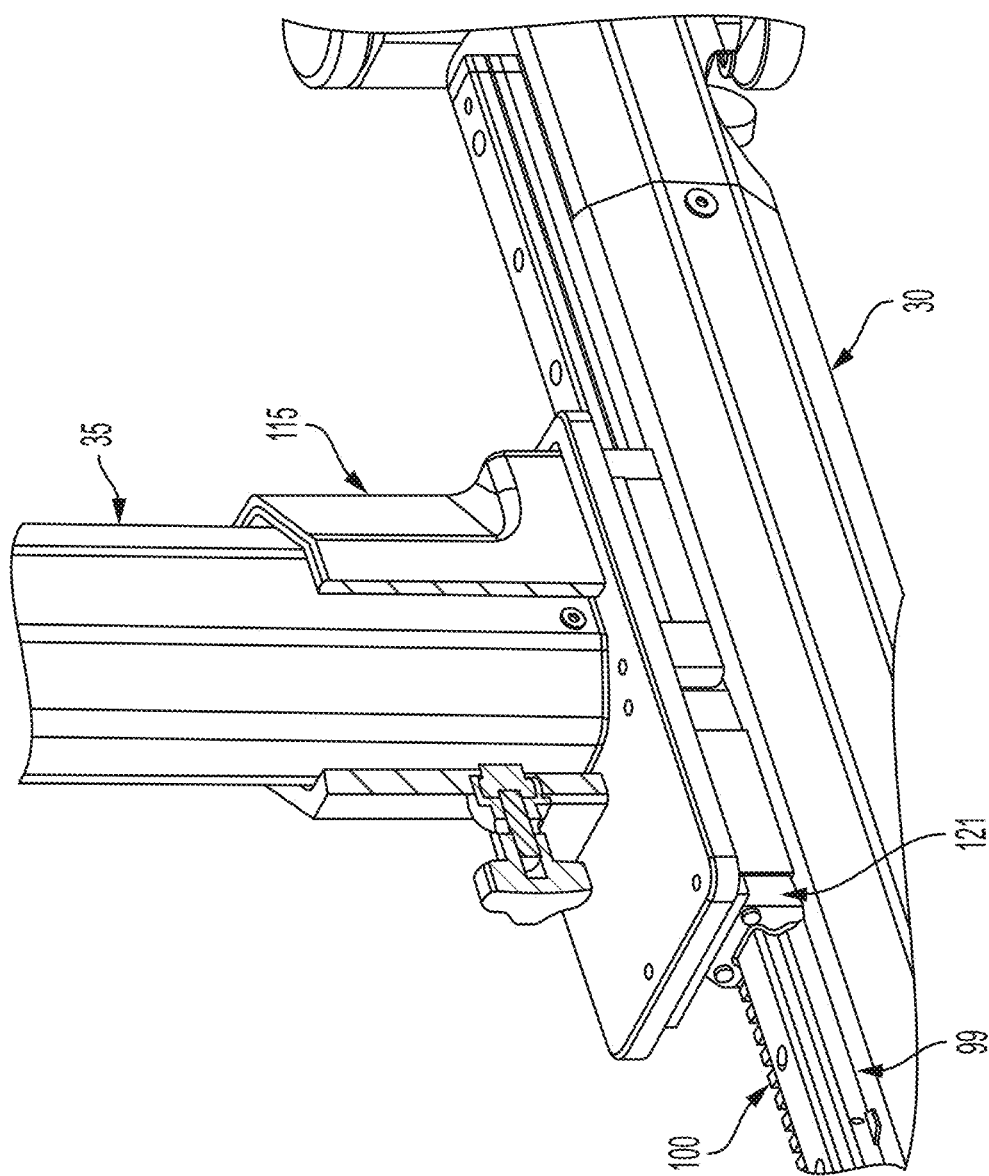
Figure 23:
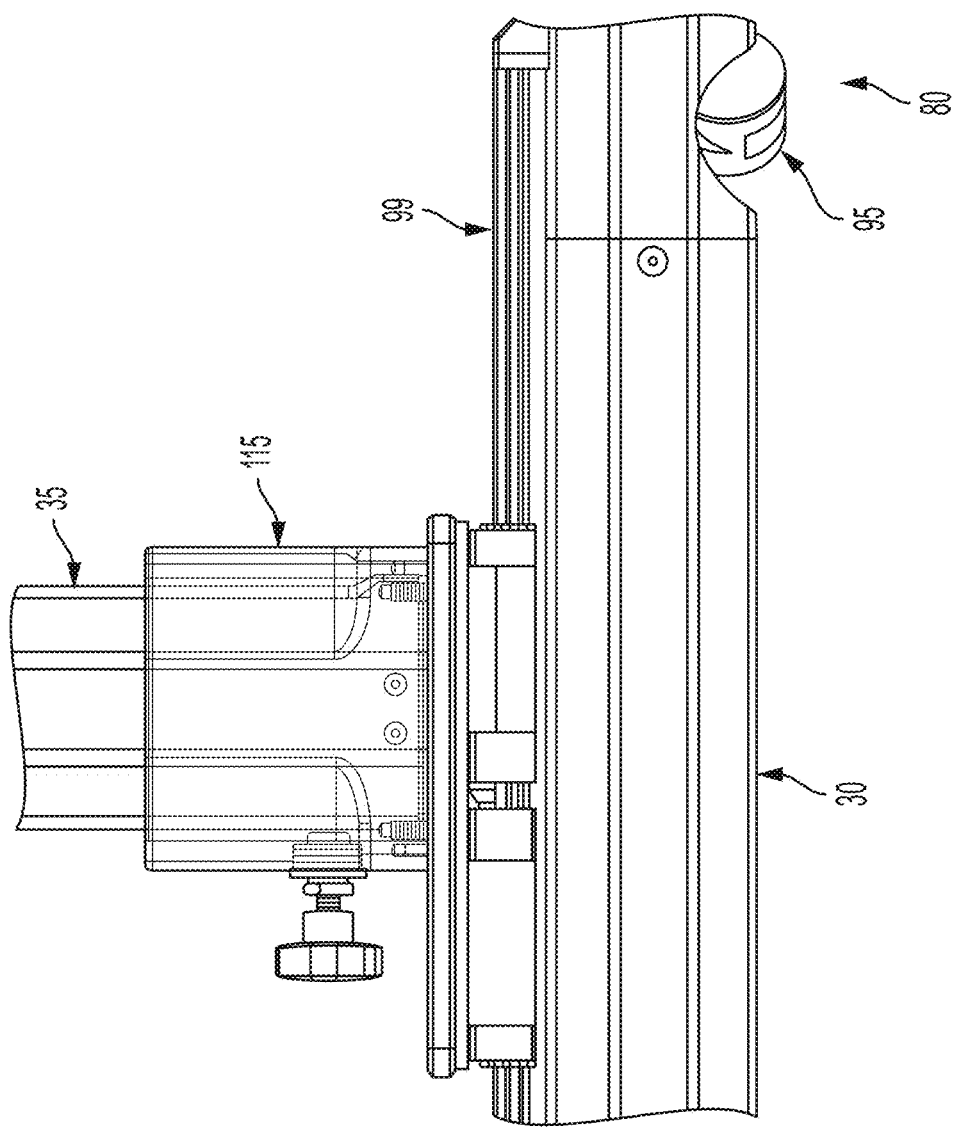
Figure 24:
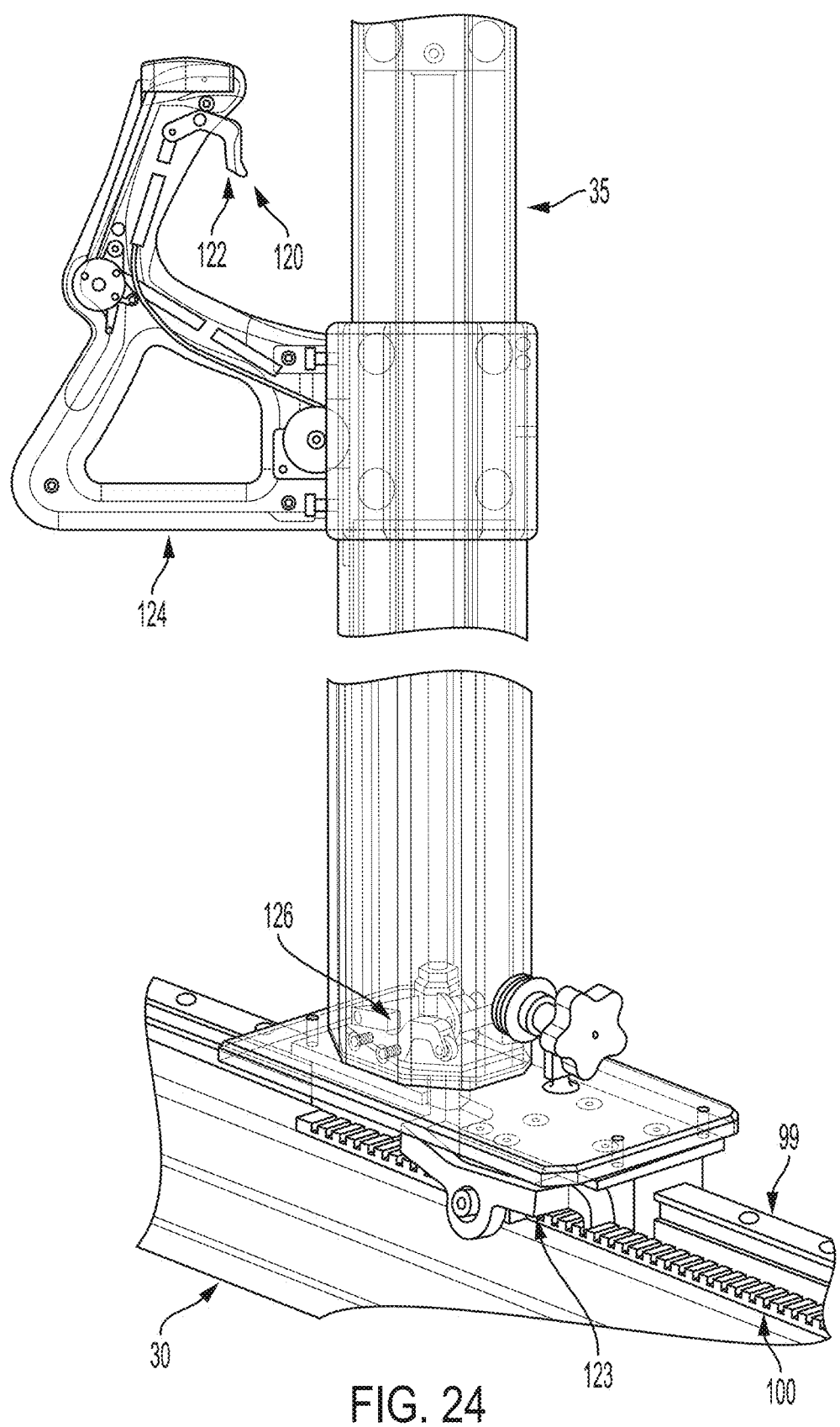
Figure 25:
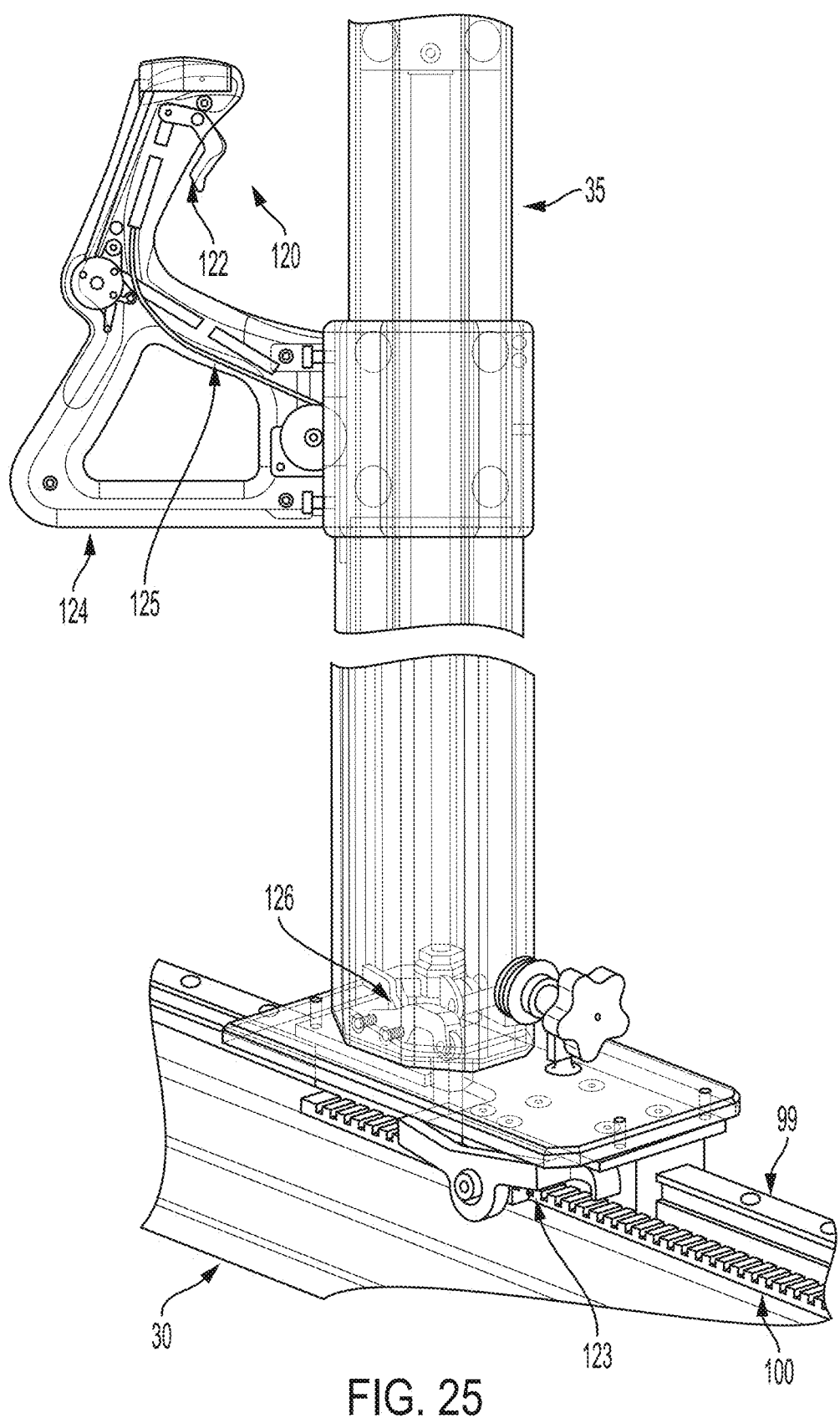
Figure 26:
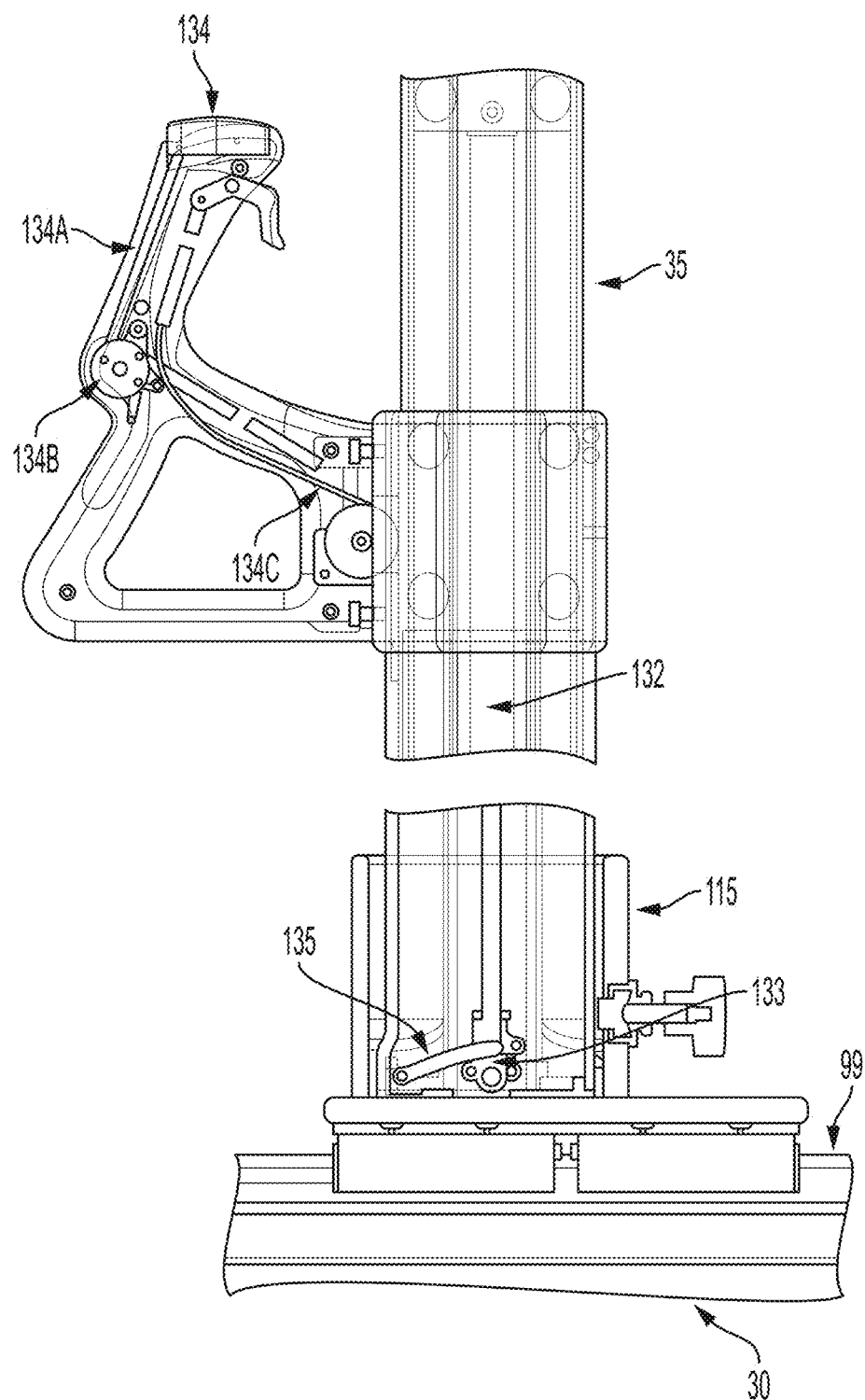
Figure 27:
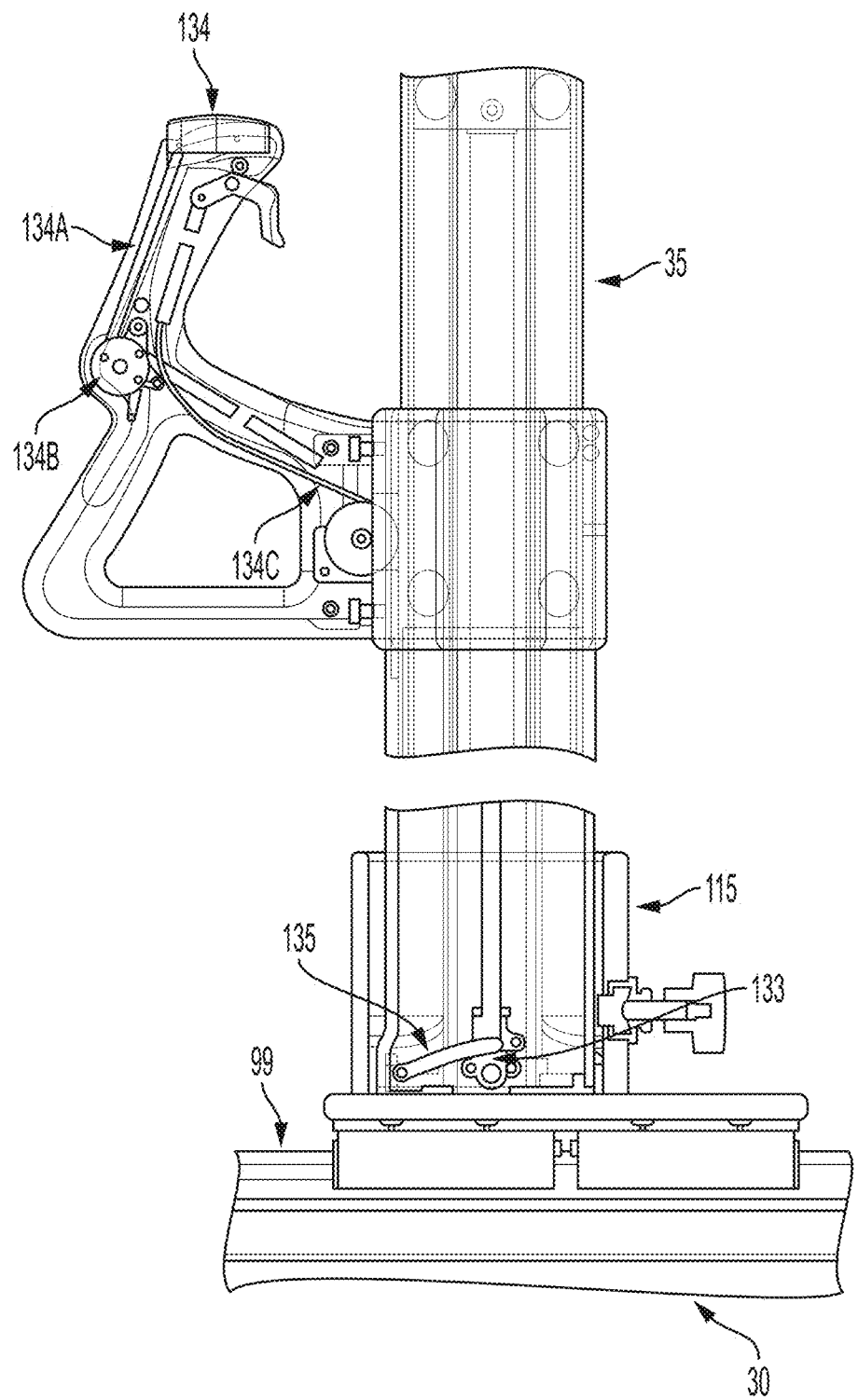
Figure 28:
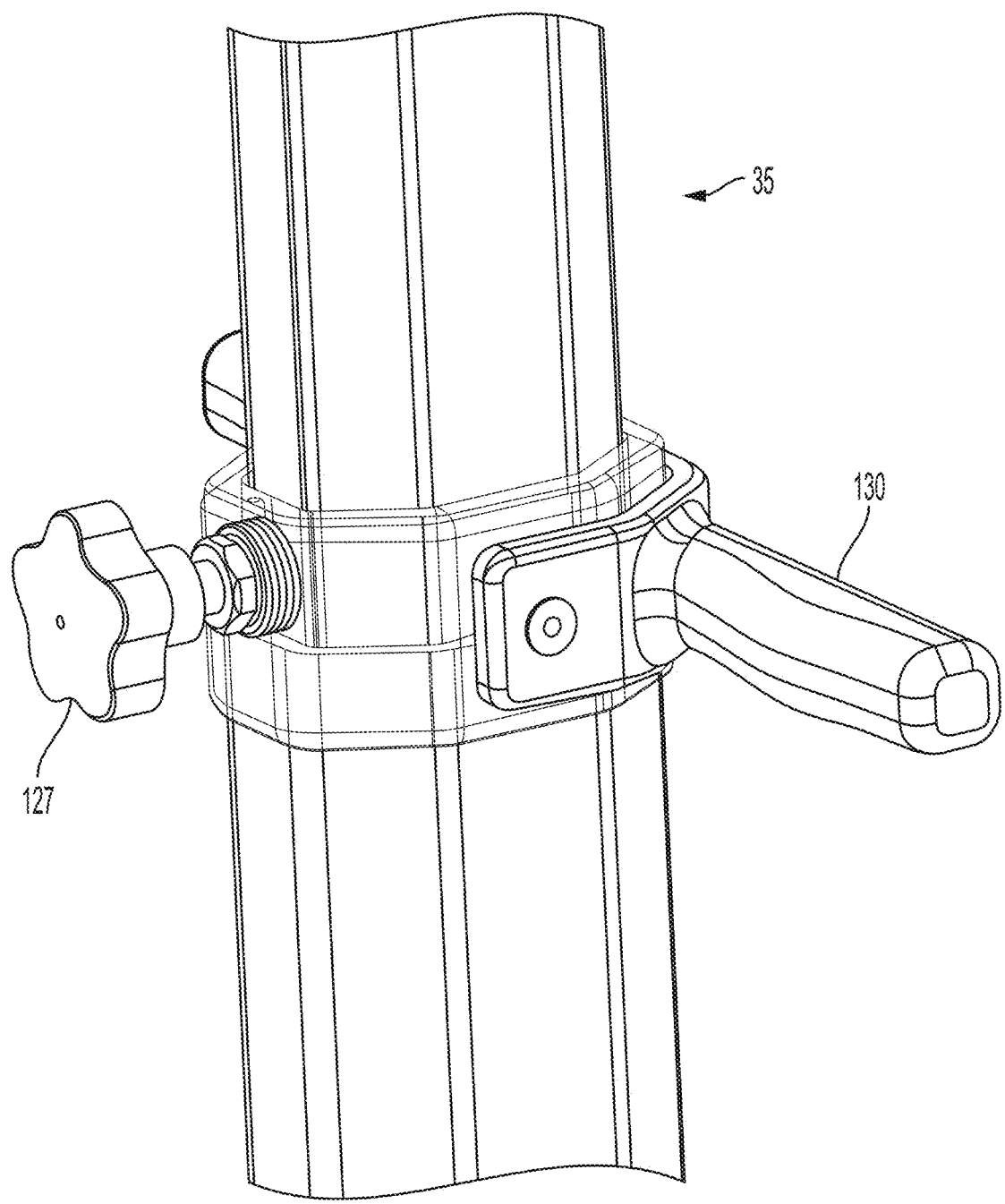
FIGS. 28, 29, 29A-29C and 30-33 are schematic views showing further details of the adjustable vertical struts (and elements attached to these struts) of the novel distraction frame shown in FIGS. 1 and 2.
Figure 29:
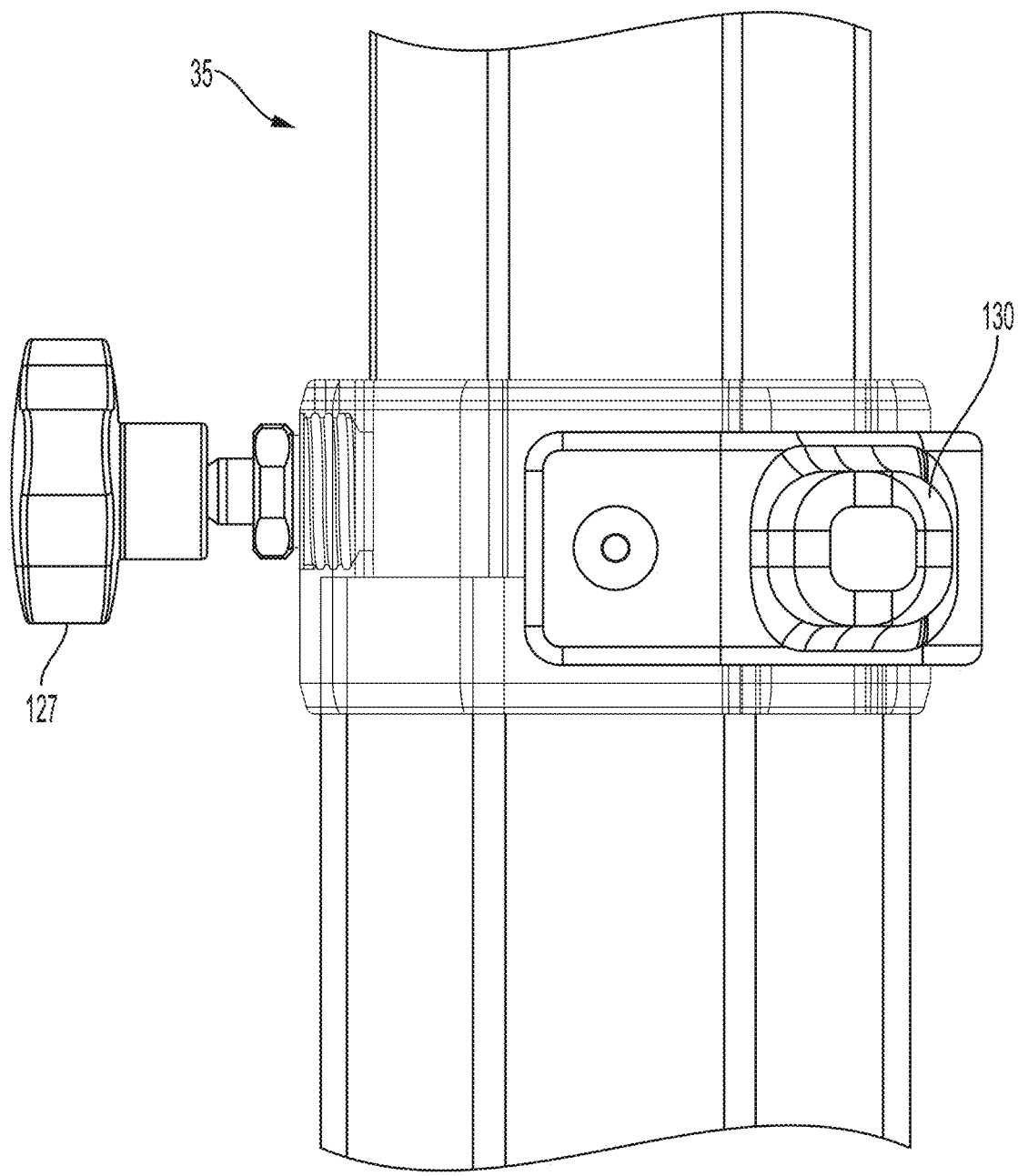
Figure 29A:
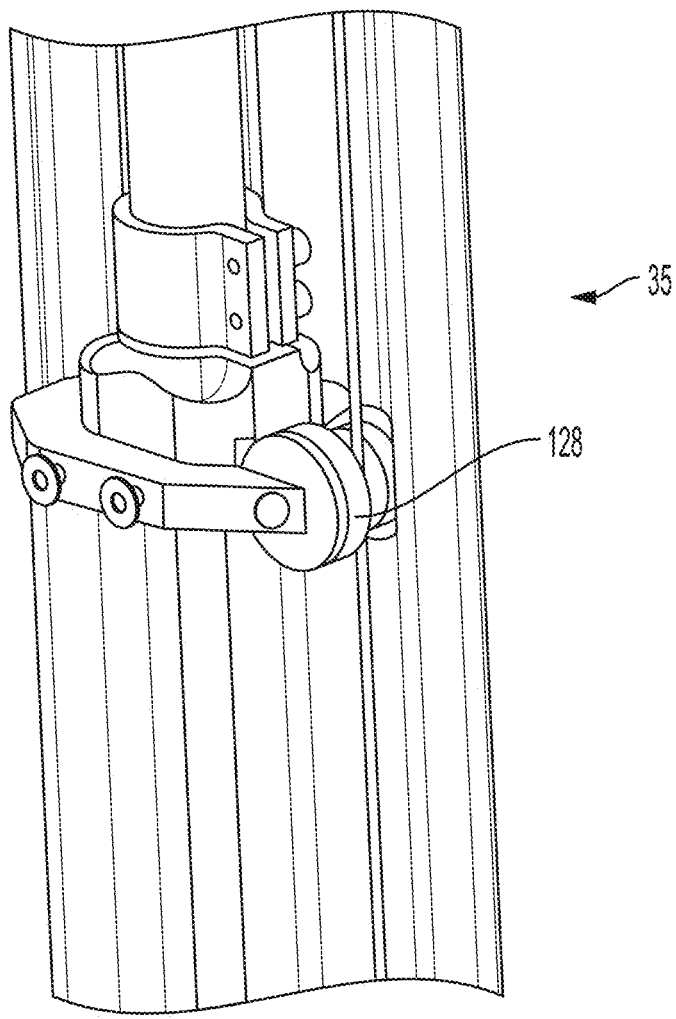
Figure 29B:
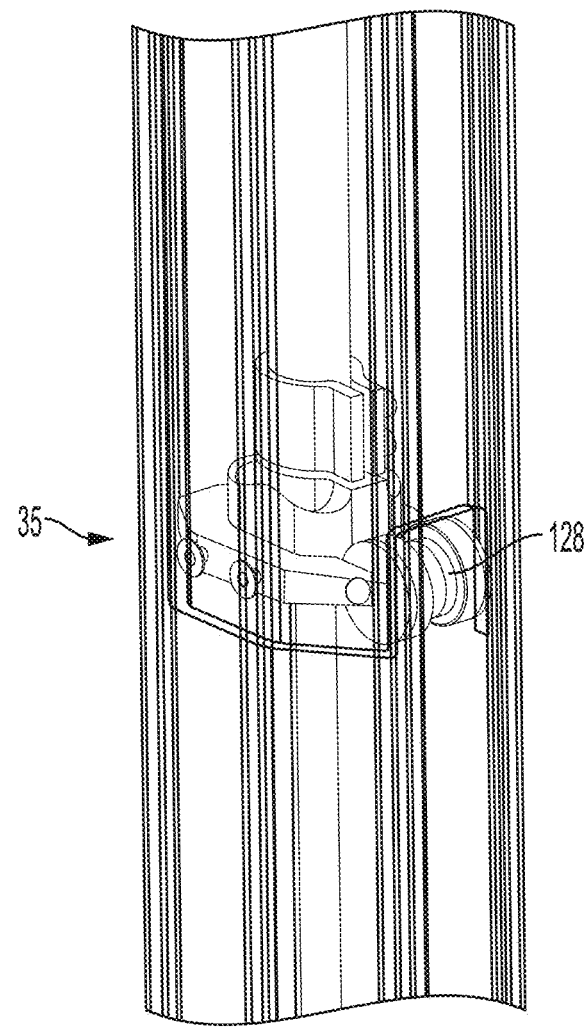
Figure 29C:
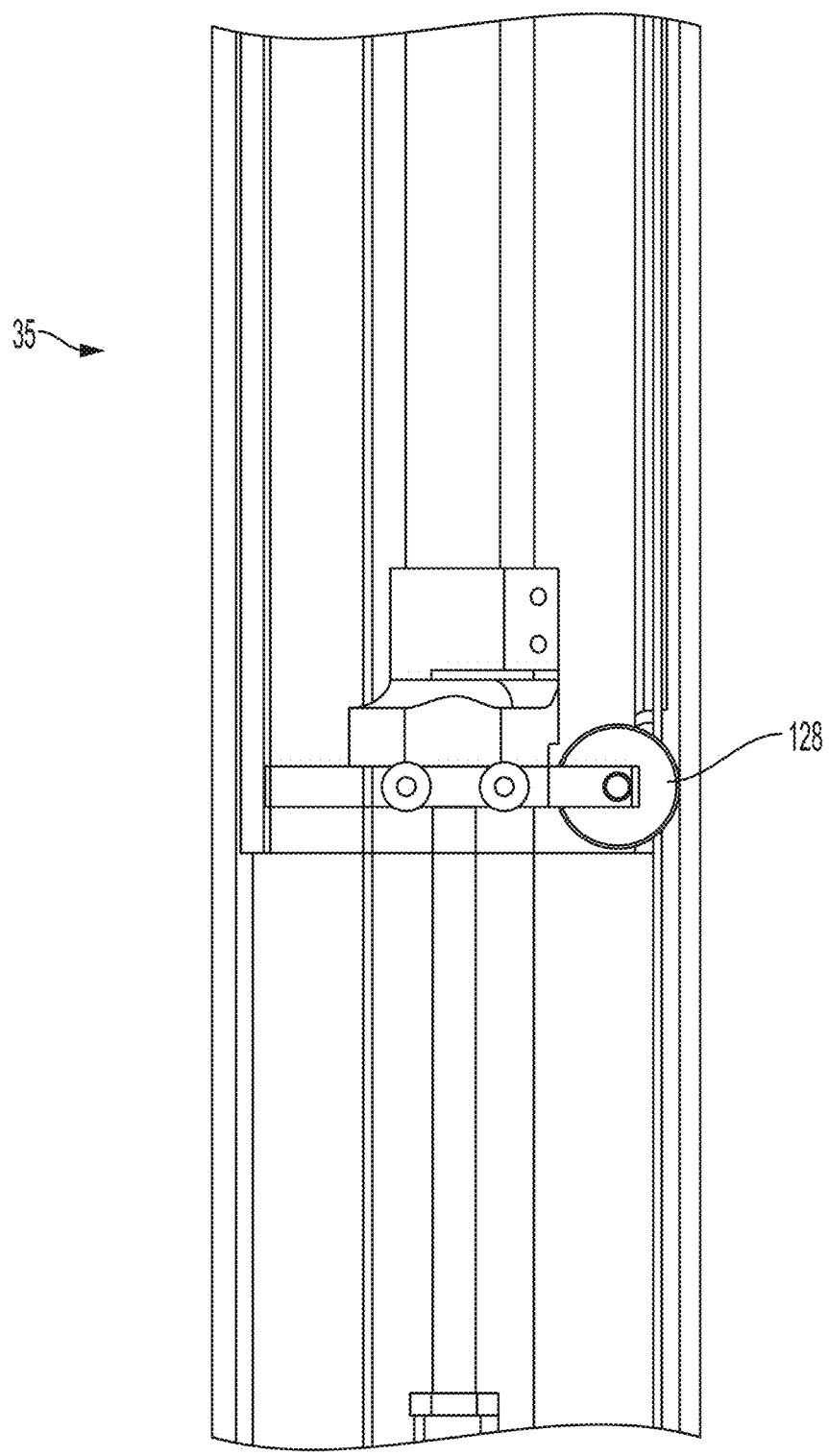
Figure 30:
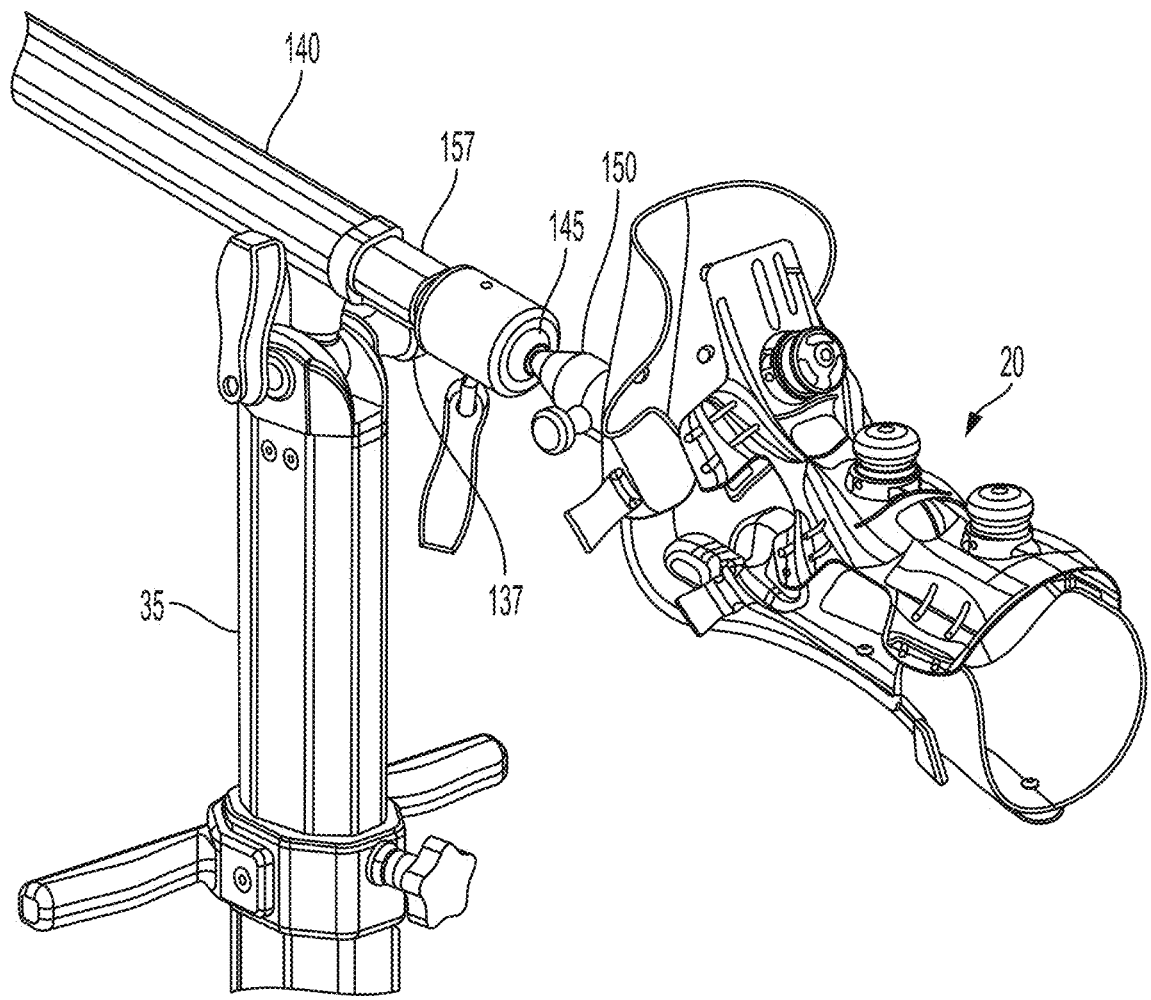
Figure 31:
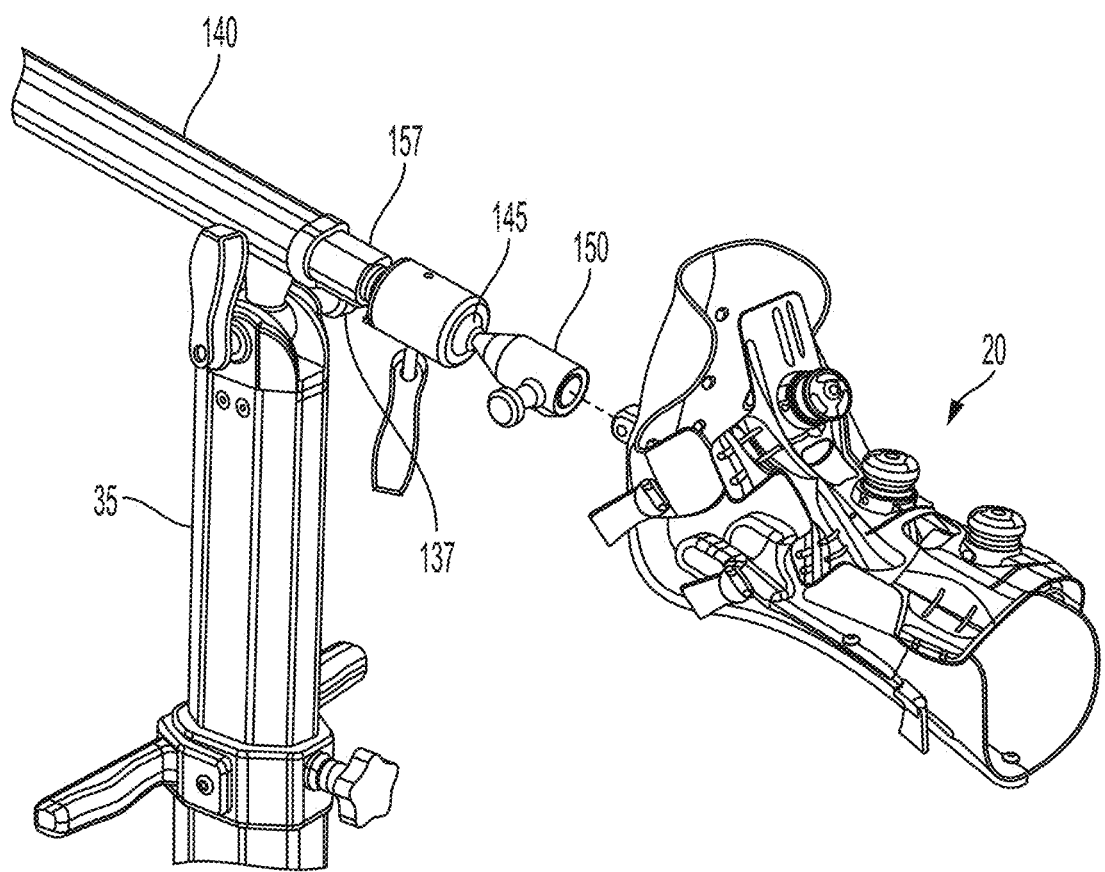
Figure 32:
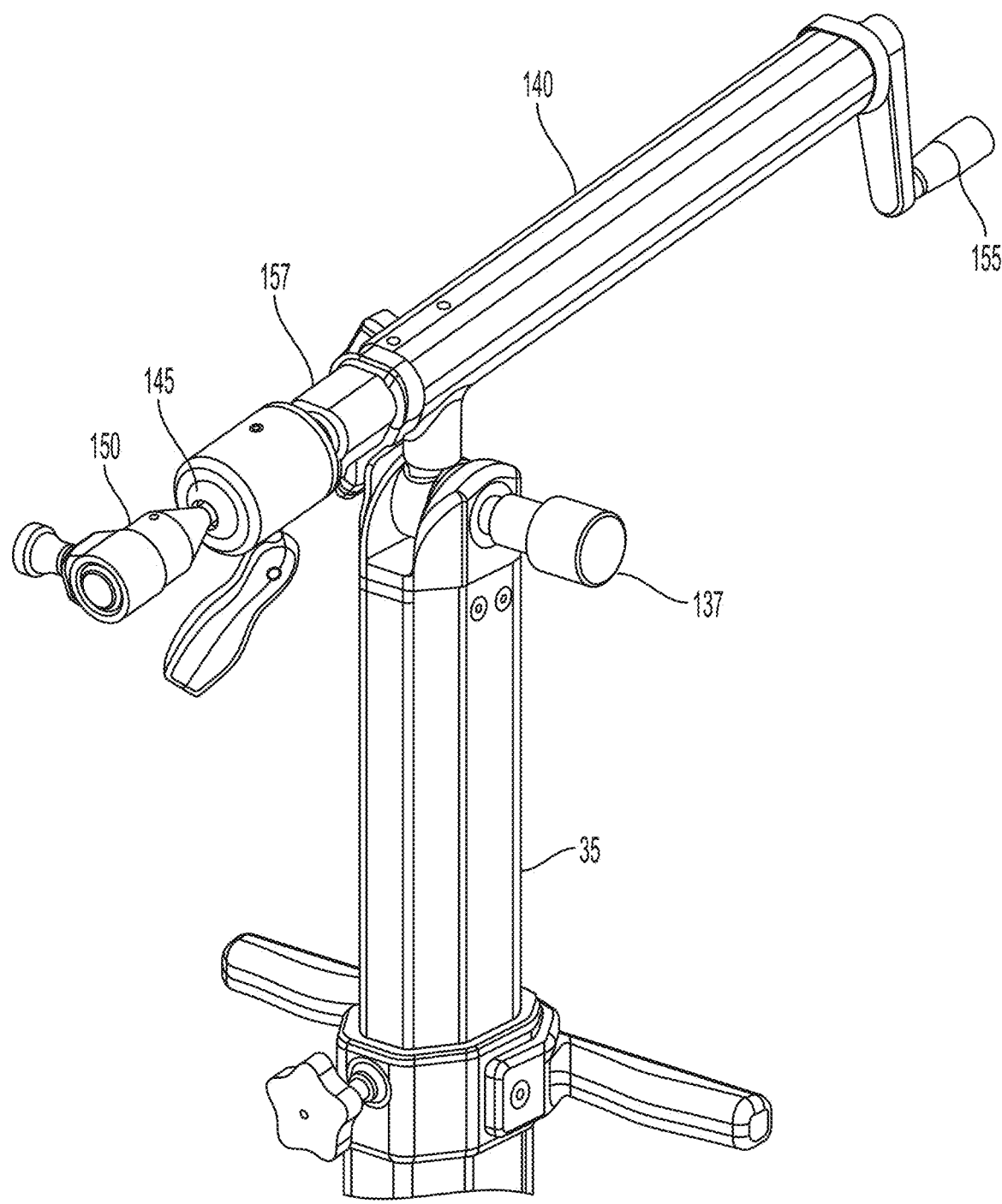
Figure 33:
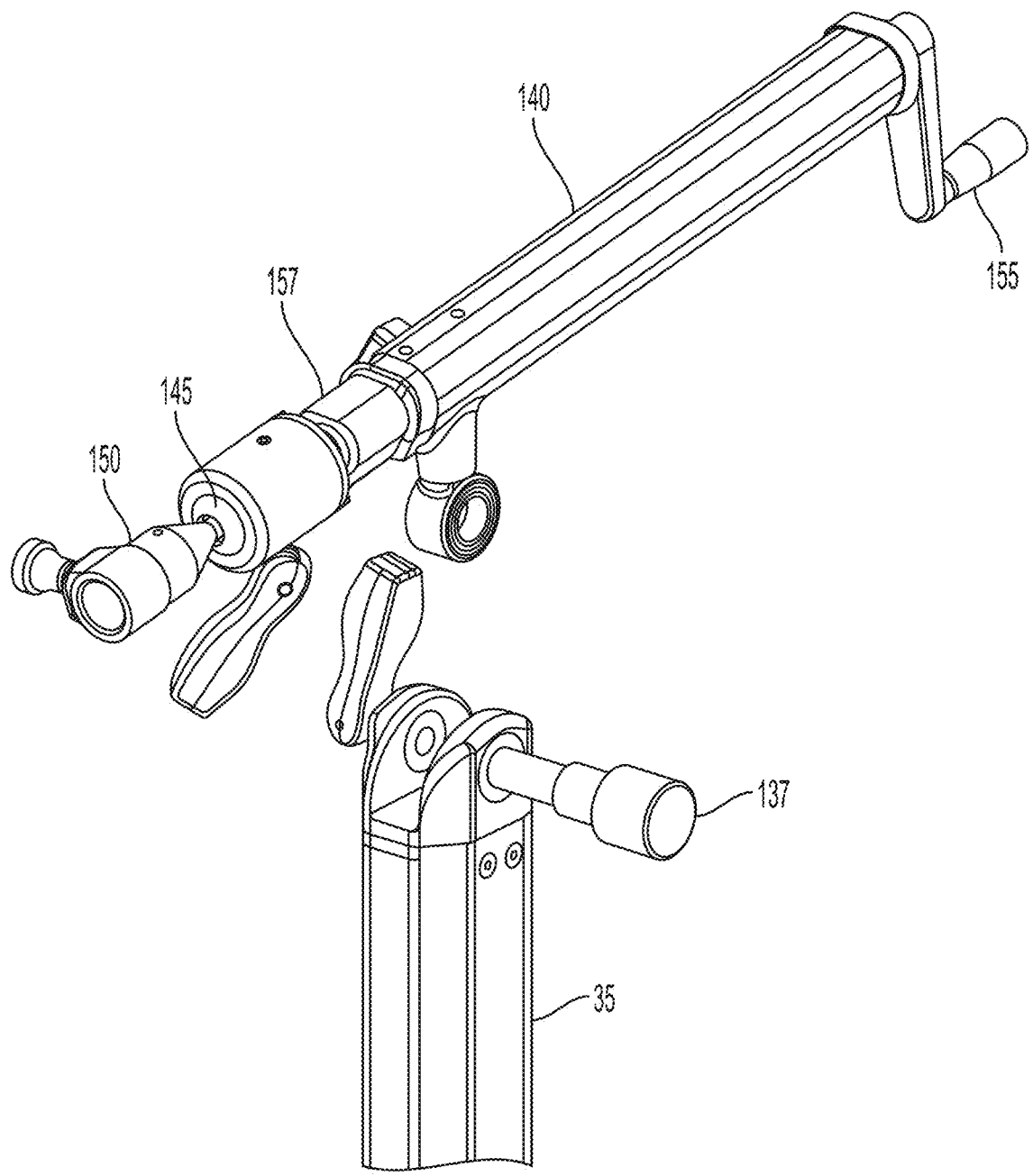

Each of the adjustable horizontal struts 30 (FIGS. 1-6, 8, 14, 15, 15A-15C, 16-21, 21A-21C and 22-27) comprises a proximal portion 75 and a distal portion 80. Proximal portions 75 and distal portions 80 telescope relative to one another. A locking screw 85 (FIG. 15) is provided to lock proximal portions 75 and distal portions 80 in position relative to one another. If desired, proximal portions 75 and distal portions 80 can be limited to discrete telescoping positions (e.g., to 3 discrete telescoping positions) or proximal portions 75 and distal portions 80 can be continuously telescopically variable relative to one another. In one preferred form of the invention, and looking now at FIGS. 15A-15C, rollers 87 are mounted to proximal portions 75 of adjustable horizontal struts 30 and roll against the inside surfaces of distal portions 80. This provides low friction movement as proximal portions 75 telescope relative to distal portions 80.

Figure 5:
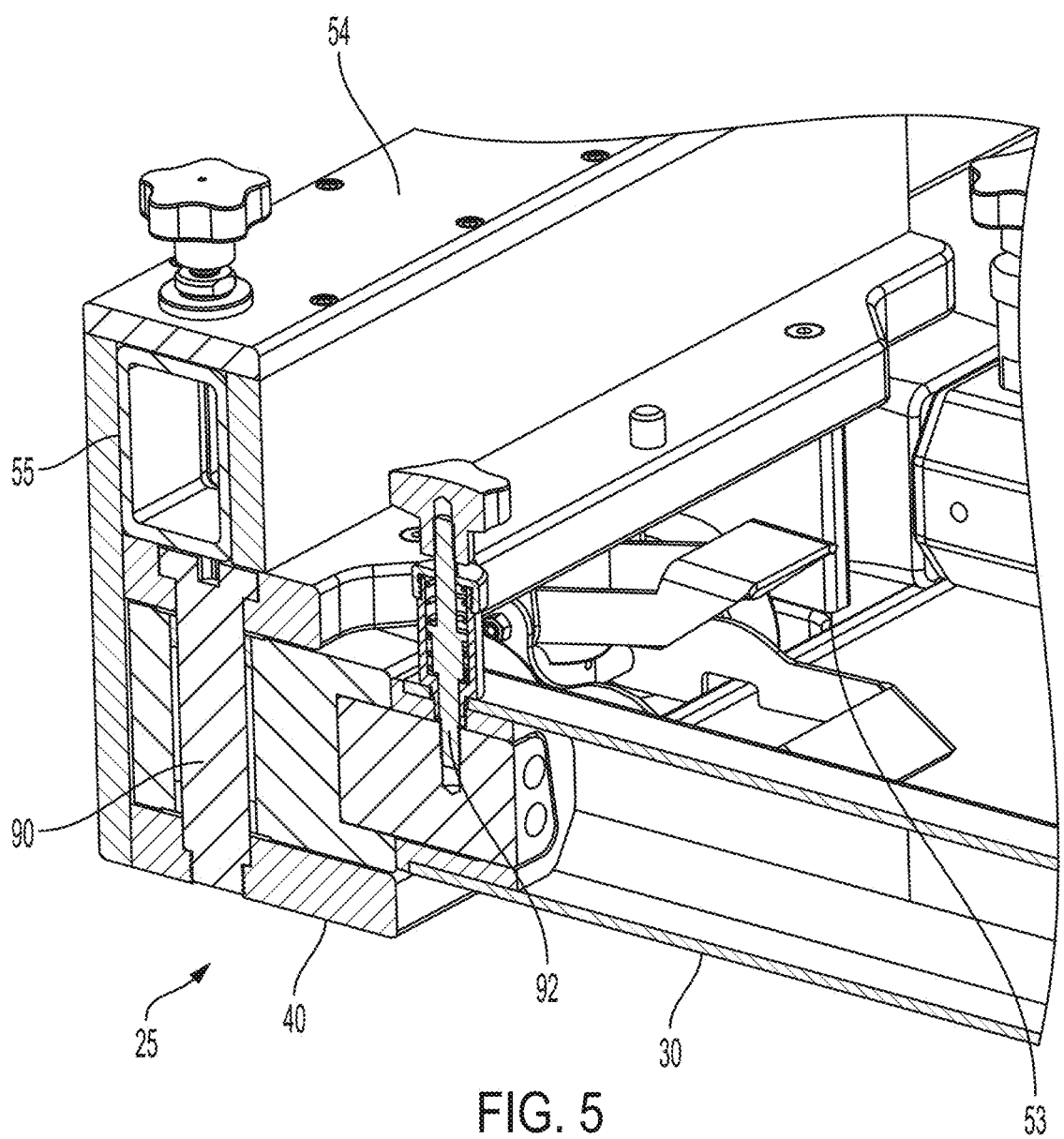
Figure 6:
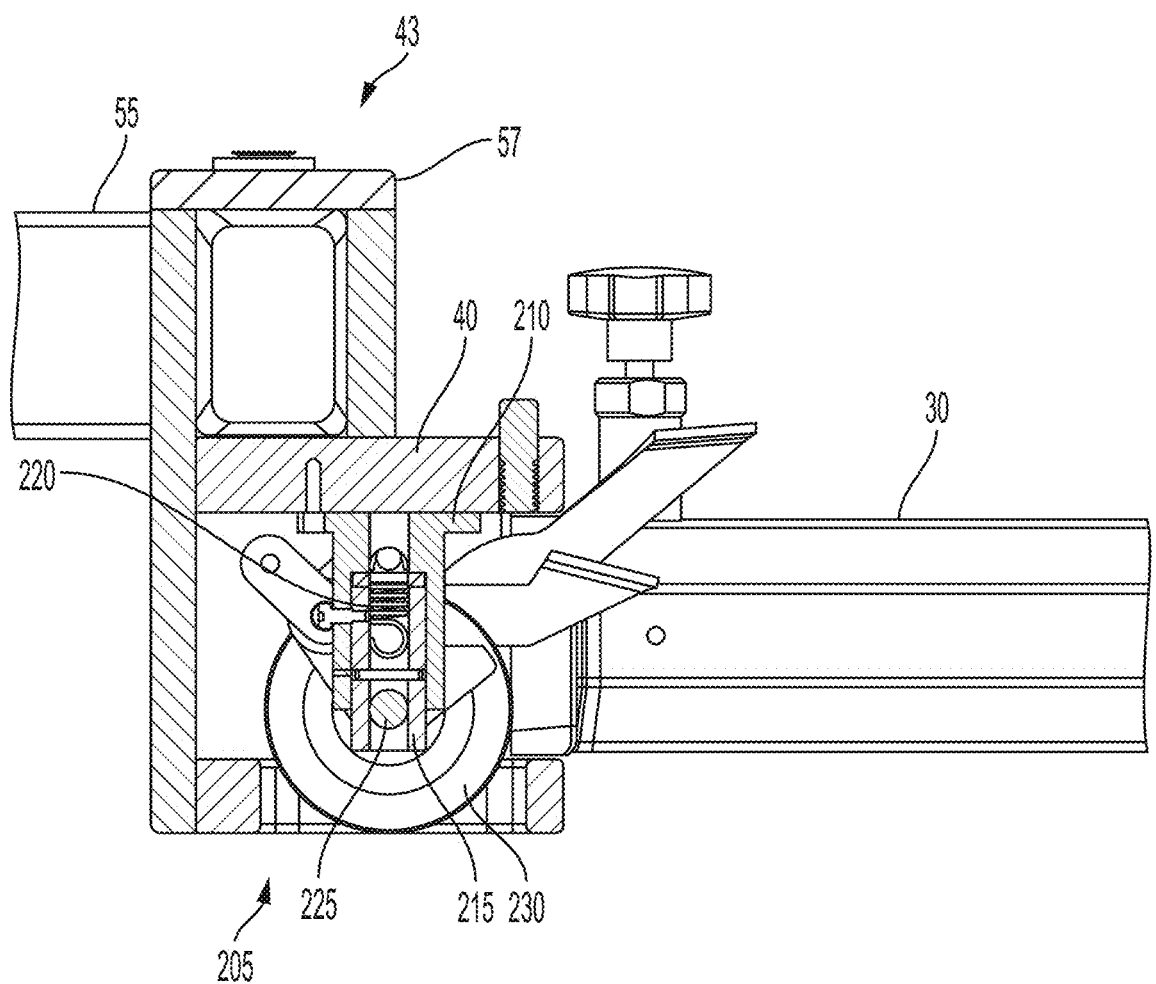

Adjustable horizontal struts 30 are pivotally mounted to body 40 of table mount 25. More particularly, proximal portions 75 of adjustable horizontal struts 30 are mounted to body 40 of table mount 25 with pivot mounts 90 (FIG. 5). Pivot mounts 90 allow proximal portions 75 of adjustable horizontal struts 30 to be adjusted to the desired angular dispositions relative to body 40 of table mount 25.

Adjustable horizontal struts 30 are detachable from body 40 of table mount 25 with locking pins 92 (FIG. 5). When locking pins 92 are raised, adjustable horizontal struts 30 can be detached from body 40 of table mount 25, providing the ability to disassemble distraction frame 5 so as to allow, for example, easier transport of distraction frame 5 to another location. In an alternative construction, adjustable horizontal struts 30 may be permanently attached to body 40 of table mount 25.

Adjustable horizontal struts 30 comprise castors 95 which are disposed at the distal ends of distal portions 80 of adjustable horizontal struts 30. Distal portions 80 of adjustable horizontal struts 30 also comprise retractable foot pegs 97. When retractable foot pegs 97 are in their retracted positions (FIGS. 16 and 17), the distal ends of distal portions 80 of adjustable horizontal struts 30 are supported on castors 95 such that the distal ends of distal portions 80 of adjustable horizontal struts 30 may roll relative to the floor. When retractable foot pegs 97 are in their extended positions (FIGS. 20 and 21), the distal ends of distal portions 80 of adjustable horizontal struts 30 are supported on retractable foot pegs 97 such that the distal ends of distal portions 80 of adjustable horizontal struts 30 may not roll relative to the floor.

In one preferred form of the invention, and looking now at FIGS. 16-21 and 21A-21C, retractable foot pegs 97 may comprise a shaft 300 which is movably mounted to a housing assembly 305 (which is, in turn, mounted to distal portion 80 of adjustable horizontal strut 30). One end of shaft 300 comprises a foot 310 for selectively engaging the floor. The other end of shaft 300 comprises a pedal 315 for selective engagement by the foot of a user. A spring 317 (FIG. 21B) biases shaft 300 upward, so that foot 310 is normally withdrawn from the floor.

Shaft 300 also comprises a track 320, and housing assembly 305 also comprises a finger 325 which rides in track 320. One end of finger 325 is pivotably mounted to housing assembly 305 while the other end of finger 325 comprises a projection 327 (FIG. 21A) which rides in track 320. Track 320 and finger 325 are configured so that when a user steps on pedal 315, driving foot 310 downward, finger 325 rides upward in a portion 328 (FIG. 21) of track 320 until finger 325 hits a peak 330 (FIG. 17) in track 320. When the user thereafter steps off of pedal 315, finger 325 settles into a recess 335 (FIG. 17) formed in track 320, whereby to lock foot 310 in its extended position (FIGS. 19 and 20), with distal portion 80 of adjustable horizontal strut 30 supported on retractable foot peg 97 (i.e., with castors 95 not in contact with the floor). When the user thereafter steps on pedal 315 again, finger 325 rides out of recess 335 and down a portion 338 (FIG. 17) of track 320 until finger 325 settles into a well 340 (FIG. 17), whereby to lock foot 310 in its retracted position (FIGS. 16 and 17), with distal portion 80 of adjustable horizontal strut 30 supported on castor 95. In this way, pedals 315 may be used to cycle retractable foot pegs 97 between their extended and retracted positions.

In one preferred form of the invention, shaft 300 comprises a gas shock assembly 345 (FIG. 21A) so that foot 310 can adjustably contact the floor. More particularly, in this form of the invention, gas shock assembly 345 comprises a rod 350 (FIG. 21A) which is secured to pedal 315, and a cylinder 355 (FIG. 21A) which is movably mounted to rod 350. Foot 310 is secured to cylinder 355. As a result of this construction, the separation between pedal 315 and foot 310 can adjust to some extent as needed, e.g., when distraction frame 5 is applying a distraction force to the leg of the patient, distal portion 80 of adjustable horizontal strut 30 can tend to lift upward relative to the floor, and gas shock assembly 345 can act to keep foot 310 firmly engaging the floor, with a certain minimum amount of force (which can be varied by adjusting the gas shock force and overall travel).

Adjustable horizontal struts 30 also comprise bearing rails 99 (FIGS. 15, 15A-15C, 16, 20 and 22-27) and gear racks 100 disposed on distal portions 80 of adjustable horizontal struts 30. Bearing rails 99 and gear racks 100 serve as a means to selectively lock adjustable vertical struts 35 at a specific location along distal portions 80 of adjustable horizontal struts 30 as will hereinafter be discussed.

Adjustable Vertical Struts 35

Each of the adjustable vertical struts 35 (FIGS. 1, 2, 16, 20, 22-29, 29A-29C and 30-33) comprises a lower portion 105 (FIG. 2), an intermediate portion 107, and an upper portion 110. Lower portions 105 comprise mounts 115 (FIG. 22) for adjustably securing adjustable vertical struts 35 to bearing rails 99 and gear racks 100 disposed on distal portions 80 of adjustable horizontal struts 30. Lock/release mechanisms 120 (FIG. 24) are provided for locking/releasing adjustable vertical struts 35 at particular dispositions along bearing rails 99 and gear racks 100 disposed on distal portions 80 of adjustable horizontal struts 30. Note that the lock/release mechanisms 120 are normally "locked" when in their "default" condition, such that mounts 115 and gear racks 100 prevent unintentional travel of adjustable vertical struts 35 along adjustable horizontal struts 30, e.g., such as when performing a hip distraction.

In one preferred form of the invention, mounts 115 comprise bearings 121 (FIG. 22) which roll along bearing rails 99, allowing adjustable vertical struts 35 to travel along the length of distal portions 80 of adjustable horizontal struts 30. This is for the purpose of allowing the user to adjust the positions of adjustable vertical struts 35 on distal portions 80 of adjustable horizontal struts 30 in order to provide different configurations for the distraction frame during a hip arthroscopy procedure (e.g., to flex or extend the leg of a patient).

Lock/release mechanisms 120 are used to lock (or release) adjustable vertical struts 35 to (or from) adjustable horizontal struts 30. More particularly, lock/release mechanisms 120 each comprise a control 122 (FIGS. 24 and 25) which is used to engage/disengage a gear lock 123 (which is housed in mount 115) to/from gear rack 100. Control 122 may be disposed within a handle 124. In one embodiment, when control 122 (e.g., a trigger) is activated, a cable 125 (FIG. 25) is pulled which disengages gear lock 123 from gear rack 100 (e.g., by pivoting a lever 126 which pivots gear lock 123 away from gear rack 100). A spring (not shown) returns gear lock 123 back to its engaged state when control 122 (e.g., a trigger) is released, i.e., when lock/release mechanism 120 is in its "default" condition.

Upper portions 110, intermediate portions 107 and lower portions 105 telescope relative to one another. Locking screws 127 (FIGS. 28 and 29) are provided to lock upper portions 110 relative to intermediate portions 107. If desired, upper portions 110 and intermediate portions 107 can be limited to discrete telescoping positions (e.g., to 5 discrete telescoping positions) or upper portions 110 and intermediate portions 107 can be continuously telescopically variable relative to one another. Handles 130 may be provided for lifting or lowering upper portions 110 and intermediate portions 107 of adjustable vertical struts 35 relative to lower portions 105 of adjustable vertical struts 35. In one preferred form of the invention, and looking now at FIGS. 29A-29C, rollers 128 are mounted to intermediate portions 107 and roll along the inner surfaces of lower portions 105. This provides low friction movement as intermediate portions 107 telescope relative to lower portions 105.

In one form of the invention, gas shocks 132 (FIG. 26) may be provided within the bodies of lower portions 105 of adjustable vertical struts 35 to help carry the loads of upper portions 110 and intermediate portions 107 of adjustable vertical struts 35 (and any loads carried thereby, e.g., the leg of a patient). In one embodiment, gas shocks 132 are housed within inner lumens of vertical struts 35, with one end of gas shocks 132 being mounted to mount 115 and the other end of gas shocks 132 being mounted to intermediate portions 107. However, it should be appreciated that gas shocks 132 may be used across all three portions of adjustable vertical struts 35 (i.e., lower portions 105, intermediate portions 107 and upper portions 110), or between a pair of portions 105/107/110, preferably between lower portions 105 and intermediate portions 107, but gas shocks 132 may also be used between upper portions 110 and intermediate portions 107.

By way of example but not limitation, where gas shocks 132 are provided to assist in adjusting the dispositions of upper portions 110 and intermediate portions 107 of adjustable vertical struts 35, gas shocks 132 are configured to apply an upward force on intermediate portions 107 of adjustable vertical struts 35 (and hence on upper portions 110, which are connected to intermediate portions 107), and gas shocks 132 include lock mechanisms 133 (FIGS. 26 and 27) for locking gas shocks 132 in a particular disposition. A button 134 (FIGS. 26 and 27) is depressed to disengage lock mechanism 133 such that gas shocks 132 are free to apply an upward force to upper portions 110 and intermediate portions 107 of adjustable vertical struts 35 (and any loads carried thereby) relative to lower portion 105 of adjustable vertical struts 35. More particularly, the depression of button 134 pushes a rod 134A (FIGS. 26 and 27), which then pivots a wheel 134B, which then pulls cable 134C, which then lifts one end of a finger 135, whereby to force the other end of finger 135 to depress lock mechanism 133. When button 134 is released, a spring (not shown) biases the foregoing elements in the opposite direction so as to release lock mechanism 133.

In lieu of a gas shock, alternative constructions may include springs or counter-weight systems to balance the loads carried by adjustable vertical struts 35.

Hinge joints 137 (FIGS. 1, 2 and 30-33) are disposed at the upper ends of upper portions 110 of adjustable vertical struts 35. Distraction mechanisms 140 are mounted at the top ends of upper portions 110 of adjustable vertical struts 35 via hinge joints 137. Universal joints 145 are disposed at the ends of distraction mechanisms 140. Mounts 150 are configured to releasably engage surgical boots 20, such that surgical boots 20 can be releasably secured to distraction mechanisms 140 (and hence to distraction frame 5). Levers 155, disposed at the opposing ends of distraction mechanisms 140, are used by the user to operate distraction mechanisms 140. More particularly, the user rotates lever 155 which, in turn, advances or retracts mount 150, and hence advances or retracts surgical boot 20. Distraction mechanisms 140 are of the sort well known in the art and generally comprise a mechanism which provides a significant mechanical advantage for the user. With this mechanical advantage, the user can apply a significant amount of distraction force to the leg of the patient. In one form of the invention, distraction mechanisms 140 comprise a force gauge 157 (FIGS. 30-33) which indicates the actual force being applied by distraction mechanisms 140 to the leg of a patient. The user can, for example, minimize potential injury to the patient if the force does not exceed a certain threshold. Force gauge 157 may be mechanical (e.g., a simple "fish scale" device with lines and numbers) or electronic (e.g., with a digital readout).

Figure 34:
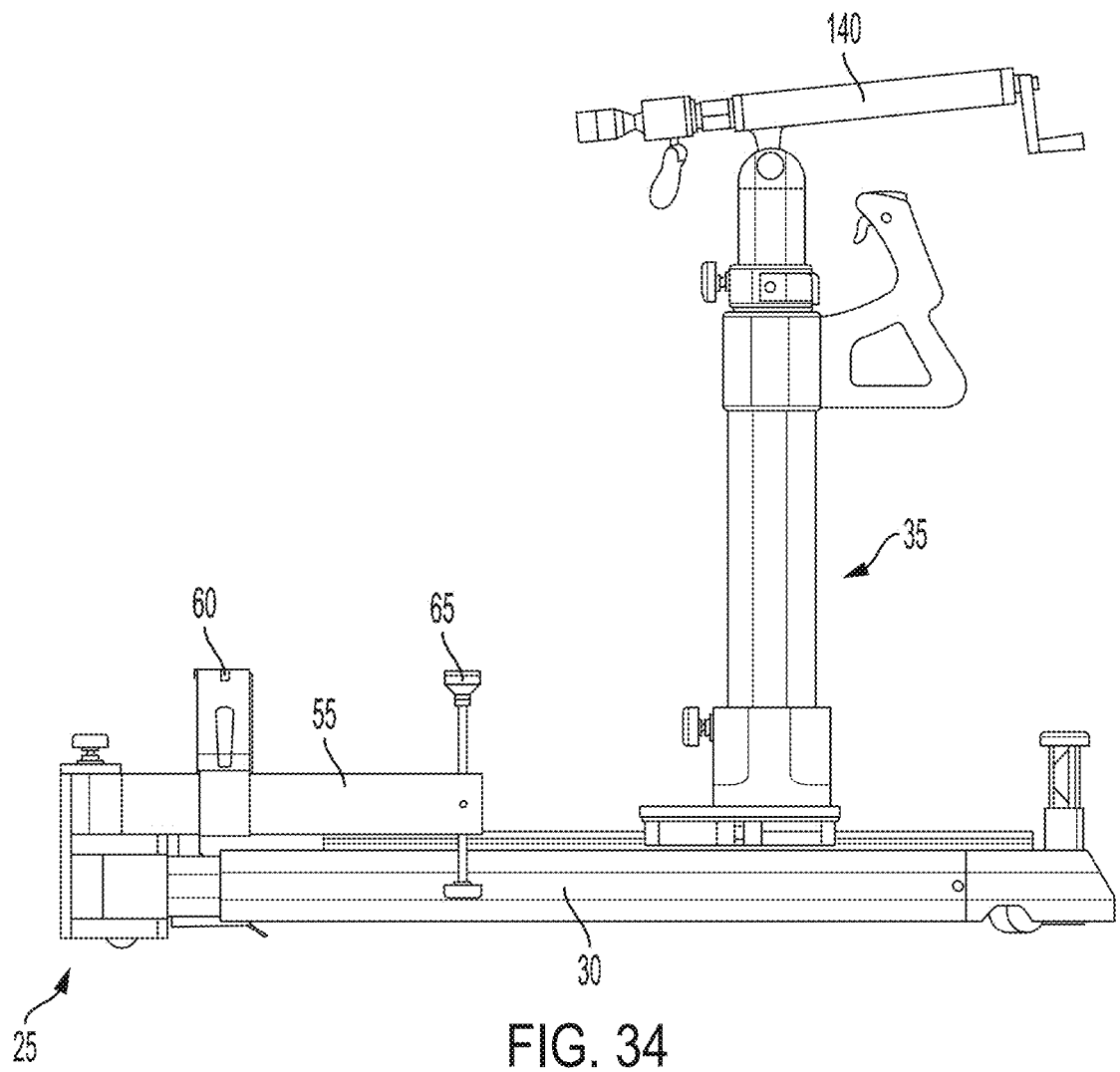
FIGS. 34 and 35 are schematic views showing how the novel distraction frame of FIGS. 1 and 2 can be positioned in transport mode for movement about a facility.
Figure 35:
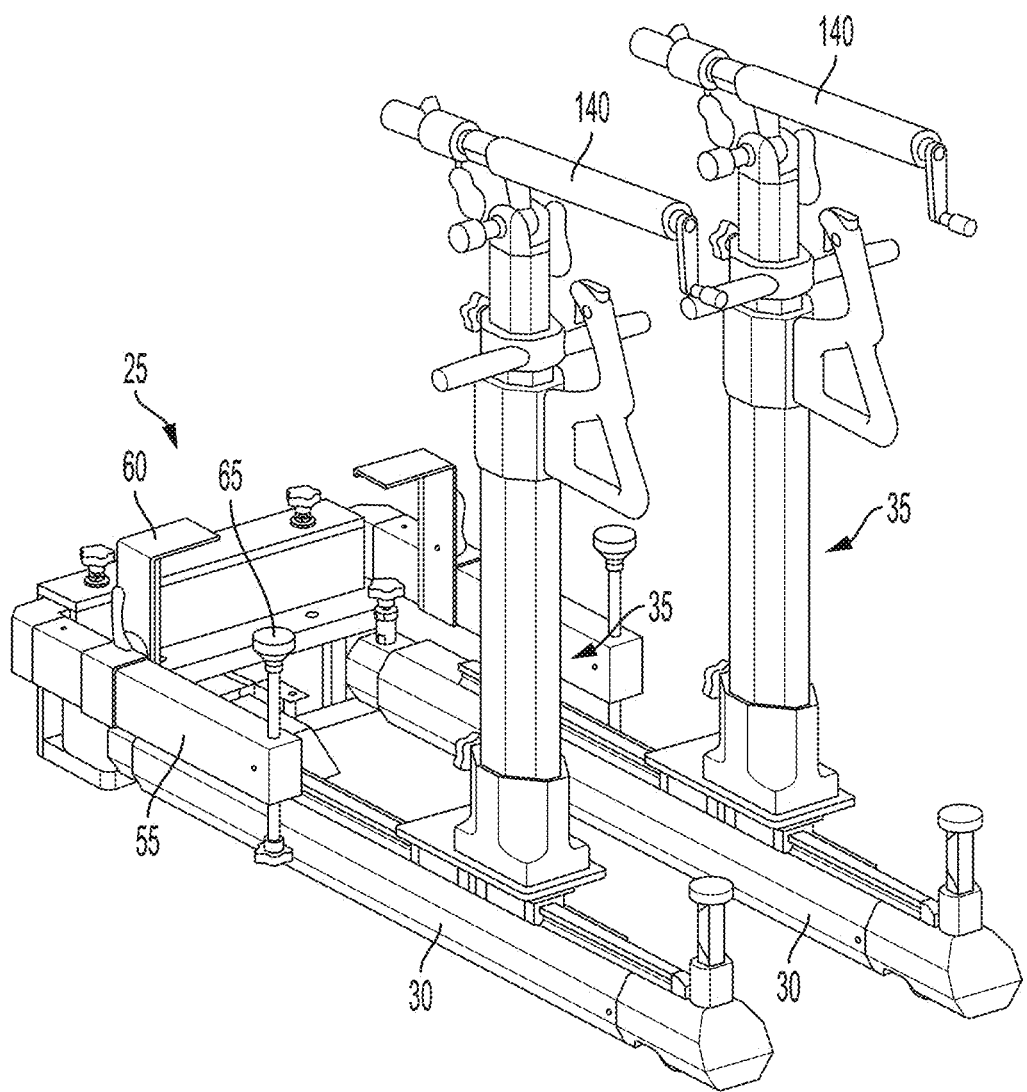

In one preferred form of the invention, the various components of distraction frame 5 are constructed so that distraction frame 5 can be "collapsed" into a compacted form, e.g., with adjustable horizontal struts 30 being telescoped into a reduced length and with adjustable vertical struts 35 being telescoped into a reduced length; and with adjustable vertical struts 35 being disposed parallel to adjustable horizontal struts 30; and with distraction mechanisms 140 being disposed parallel to adjustable vertical struts 35 and adjustable horizontal struts 30; and with L-shaped extensions 55 being inverted so that L-shaped brackets 60 and adjustable supports 65 face upward and with L-shaped extensions 55 being reversed relative to body 40 of table mount 25 so that L-shaped extensions 55 are set back over adjustable horizontal struts 30. In addition, wheels 230 of table mount 25 are in their "down" position, and retractable foot pegs 97 of adjustable horizontal struts 30 are in their "up" position so that adjustable horizontal struts 30 rest on castors 95, such that distraction frame 5 rides on wheels 230 and castors 95. See FIGS. 34 and 35. In this configuration, distraction frame 5 can be transported to another operating room or other location in the hospital (e.g., a storage location). Effectively, in this configuration, distraction frame 5 does not require a separate piece of equipment for mobility (e.g., a tote, a dolly, etc.). This provides significant convenience for the hospital staff.

Use of Distraction Frame 5

Distraction frame 5 is preferably used as follows.

First, distraction frame 5 is assembled so that adjustable horizontal struts 30 are mounted to table mount 25, adjustable vertical struts 35 are mounted to adjustable horizontal struts 30, and distraction mechanisms 140 are mounted to upper portions 110 of adjustable vertical struts 35 (if these components are not already mounted to one another). In addition, L-shaped extensions 55 are set so that L-shaped brackets 60 and adjustable supports 65 face downward, and L-shaped extensions 55 are attached to body 40 of table mount 25 so that L-shaped extensions 55 extend away from adjustable horizontal struts 30 (if these components are not already set in this position).

Then distraction frame 5 is wheeled up to surgical table 10 on wheels 230 of retractable wheel assembly 205 and castors 95 of adjustable horizontal struts 30, and distraction frame 5 is assembled to surgical table 10 by mounting table mount 25 to base 15 of surgical table 10, e.g., by setting L-shaped extensions 55 on both sides of base 15 of surgical table 10, positioning L-shaped brackets 60 beneath table feet 62 of surgical table 10, retracting wheels 230 of retractable wheel assembly 205 so that horizontal surface 50 of body 40 seats on the floor, and then lowering feet 62 of surgical table 10 onto L-shaped brackets 60. Adjustable supports 65 are also adjusted as necessary to make secure contact to the floor.

Next, distraction frame 5 is approximately configured for the size of the patient, the size of the surgeon, and the procedure to be conducted. This is done by setting the angles of adjustable horizontal struts 30 relative to table mount 25 (and hence relative to surgical table 10), setting the lengths of adjustable horizontal struts 30, setting the dispositions of adjustable vertical struts 35 on adjustable horizontal struts 30, and setting the heights of adjustable vertical struts 35.

Then the patient's feet and legs are placed into, and secured to, surgical boots 20. Surgical boots 20 are secured to distraction mechanisms 140 disposed at the top ends of upper portions 110 of adjustable vertical struts 35. Further adjustments may be made to distraction frame 5 as necessary.

Distraction may occur with the surgical table set in a horizontal position or in an inclined position (e.g., with the patient in the so-called Trendelenburg position). For purposes of example but not limitation, distraction will now be discussed in the context of the patient having their leg distracted while in the Trendelenburg position.

The patient is tilted on the surgical table to the Trendelenburg position. This is accomplished with the surgical table controls. Preferentially the amount of Trendelenburg angle is 15 degrees or less. To accommodate this change in patient position, distraction frame 5 may be adjusted again as needed. In particular, the height of adjustable vertical struts 35 might be increased to maintain the patient in a planar position (relative to the table top) or with a small amount of hip flexion; horizontal struts 30 may then be adjusted so as to minimize distraction forces applied to the hip. It is also beneficial that during the application and removal of the Trendelenburg angle, lock/release mechanism 120 of mount 115 is able to be maintained in an unlocked position. This allows for the change in angle relative to distraction frame 5 without putting undue stresses on the patient as the leg length changes relative to the horizontal plane of adjustable horizontal strut 30.

Next, distraction frame 5 is more precisely configured to begin the procedure to be conducted. This is done by more precisely setting the angles of adjustable horizontal struts 30 relative to table mount 25 (and hence relative to surgical table 10), more precisely setting the dispositions of adjustable vertical struts 35 on adjustable horizontal struts 30, and more precisely setting the heights of adjustable vertical struts 35, more precisely setting the length and angle of the distraction mechanisms 140, and more precisely setting the angle of surgical boots 20.

The patient's hip may then be distracted by the surgical team by unlocking lock/release mechanism 120 of mount 115 and pulling distally on adjustable vertical struts 35, e.g., via handle 124. From this starting position, at least 8 inches of travel along the horizontal struts 30 is provided for the surgical team to apply this pulling force to the patient. Then distraction mechanisms 140 (disposed at the top ends of upper portions 110 of adjustable vertical struts 35) are adjusted as needed so as to apply the desired distraction force to the distal end of the patient's leg. From the starting position, at least 4 inches of additional travel is provided within distraction mechanism 140 to apply force to the patient's leg. Any combination of these applications of traction is envisioned, as needed for the patient's treatment.

Once the patient's hip is appropriately distracted, a surgical procedure may then be conducted on the distracted hip.

It should be appreciated that distraction frame 5 of the present invention provides the ability to attain more C-arm positions than prior art distraction frames. This is due to the fact that distraction frame 5 mounts to base 15 of surgical table 10 and not to the end of the surgical table. Therefore, the space immediately under table extender 23 and above table mount 25 and adjustable horizontal struts 30 is open and allows the C-arm X-ray machine to be manipulated with a high degree of freedom.

It should also be appreciated that distraction frame 5 of the present invention has 8 degrees of freedom: (1) gross traction extension/retraction (moving adjustable vertical struts 35 away from/toward the patient); (2) adduction/abduction of adjustable horizontal struts 30 pivoting about body 40; (3) adjustable vertical struts 35 raising and lowering; (4) distraction mechanisms 140 (fine traction) pivoting on adjustable vertical struts 35; (5) distraction mechanisms 140 (fine traction) retracting/advancing; and (6), (7) and (8) surgical boots 20 rotating and pivoting about universal joints 145. The 8 degrees of freedom provided by distraction frame 5 are superior to the 3-5 degrees of freedom typically provided by the prior art, thereby providing the surgeon with the ability to position the patient's leg in a greater number of positions and orientations. This allows the surgeon to access anatomy that they could not previously be accessed with the distraction systems of the prior art.

The distraction frame of the present invention also allows for more deep flexion of the patient's hip due to the increased degrees of freedom provided by the distraction frame and due to the disassociation of the height of the distraction frame (where the patient's foot connects to the distraction frame) relative to the top of the surgical table. Because the patient's foot can be raised (by adjustment of the vertical struts) independently of the patient's horizontal position, additional flexion can be achieved by the distraction frame of the present invention.

In addition to the foregoing, it should also be appreciated that distraction frame 5 is able to accommodate a wide range of patient heights, i.e., from approximately 4'10" to approximately 6'10". This ability to accommodate a wide range of patient heights is due to the more numerous degrees of freedom combined with the adjustable nature of various components of distraction frame 5, e.g., the adjustability of adjustable horizontal struts 30.

Significantly, adjustable vertical struts 35 can be positioned away from surgical table 10; this provides more space for the surgical staff to maneuver at the end of the table during surgical preparation, including while a patient is being transferred onto the surgical table.

Figure 36:
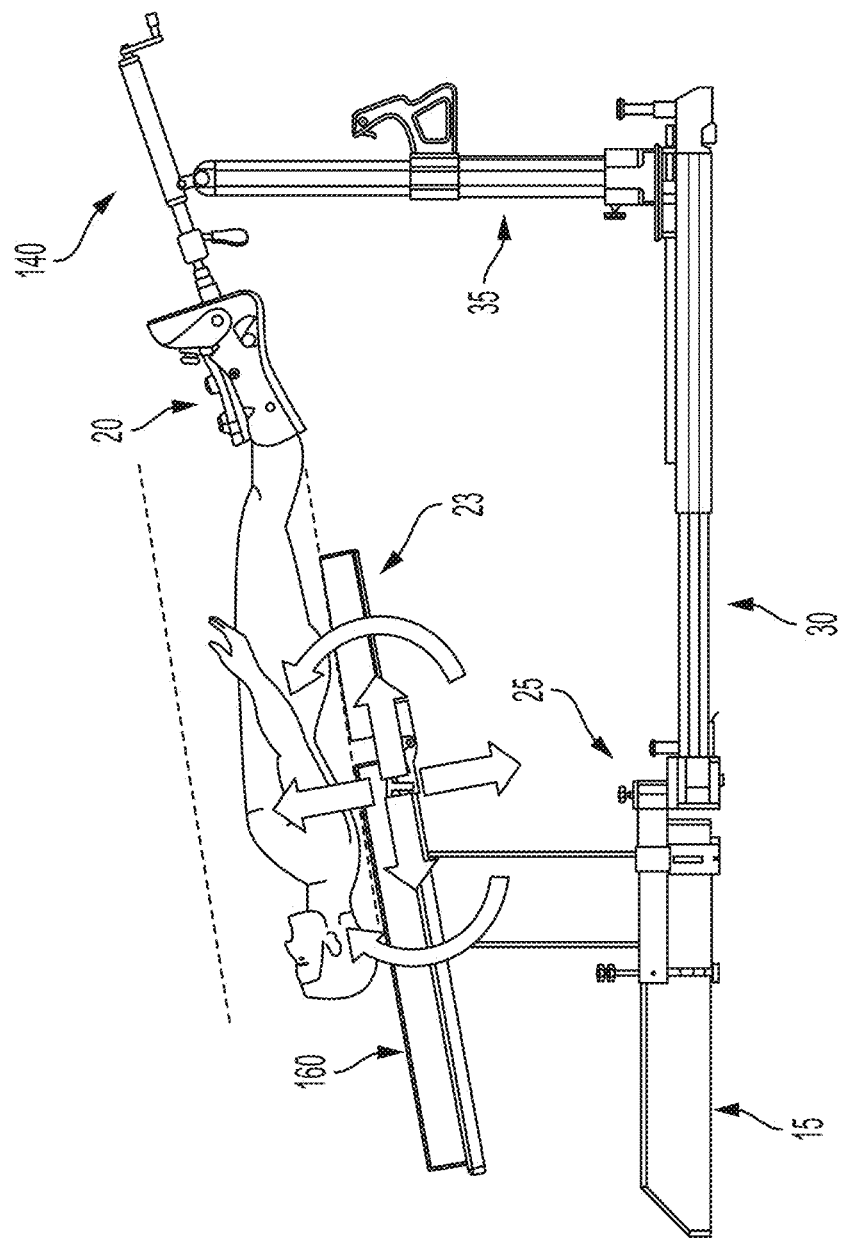
FIG. 36 is a schematic view showing how table tilt can be used to influence distraction after a patient's leg has been secured to a distraction frame.

It should also be appreciated that, in addition to manipulating distraction frame 5 to effect hip distraction, the surgical table may also be manipulated to effect hip distraction. More particularly, and looking now at FIG. 36, the bed 160 of surgical table 10 can typically be moved up/down, moved cephalad/caudal, tilted head-to-toe, and tilted side-to-side. If a patient is positioned on bed 160 of surgical table 10 and the patient's feet are attached to distraction frame 5, then movement of bed 160 of surgical table 10 in a cephalad direction will have the same effect as applying tension to the leg by means of turning levers 155 of distraction mechanisms 140 so as to move the foot in a caudal direction.

It should be appreciated that a patient can be in either a lateral decubitus position or a supine position on surgical table 10. In a lateral decubitus position, the patient lays on their side on the surgical table with the non-operative leg supported by the table and the operative leg supported by distraction frame 5. In the supine position, the operative leg is supported by distraction frame 5 and the non-operative leg would rest on surgical table 10 and table extender 23. However, table extender 23 typically stops above the knee of the patient, so the non-operative leg has limited support.

Figure 37:
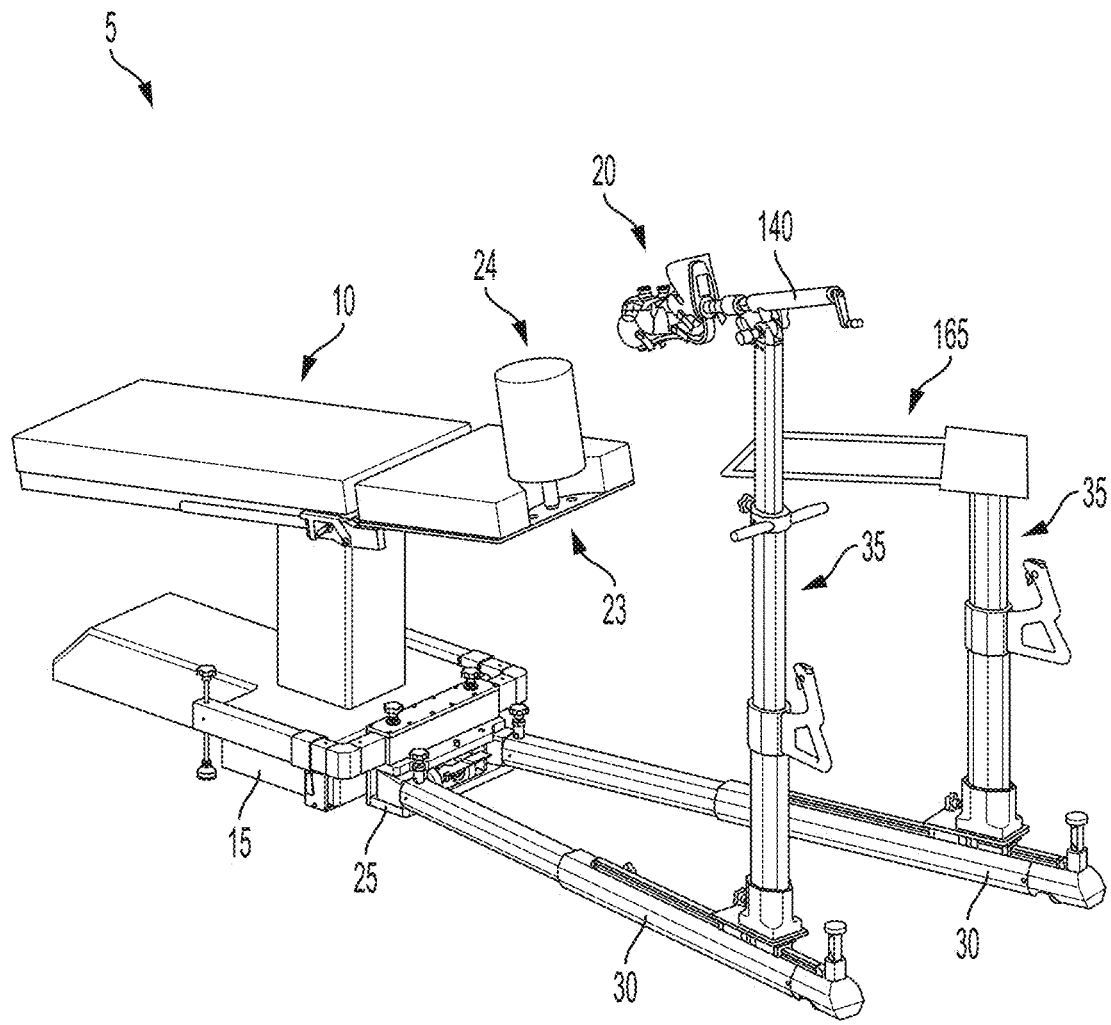
FIG. 37 is a schematic view showing another novel distraction frame formed in accordance with the present invention, wherein the distraction frame comprises a leg rest for supporting the non-operative leg of a patient.

To this end, in an alternative construction, one of adjustable vertical struts 35 may replace its hinge joint 137, distraction mechanism 140, universal joint 145, mount 150, force gauge 157 and lever 155 with a leg board 165 (FIG. 37) which is mounted to one of the adjustable vertical struts. Since the non-operative leg sees no force during distraction and is typically not manipulated, the non-operative leg does not need to be secured to distraction frame 5 but can simply be supported by leg board 165.

It should also be appreciated that distraction frame 5 may be used for orthopedic procedures other than hip arthroscopy, e.g., distraction frame 5 may be used for hip trauma, total hip replacement, etc.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

The invention claimed is:

1. A method comprising:
  rolling a distraction frame across a floor to a surgical table on at least one wheel of a table mount of the distraction frame and at least one caster of a vertical strut of the distraction frame, the at least one caster being connected to the table mount via at least one horizontal strut; and
  positioning the table mount for removably mounting to the surgical table; and
  selectively disengaging the at least one wheel and the at least one caster from the floor, wherein selectively disengaging the at least one wheel from the floor comprises retracting the at least one wheel so that a surface of the table mount seats on the floor.

2. The method of claim 1, comprising, after selectively disengaging the at least one wheel from the floor, lowering at least one foot of the surgical table onto the table mount.

3. The method of claim 2, wherein positioning the table mount for removably mounting to the surgical table comprises positioning at least one bracket of the table mount beneath at least one foot of the surgical table.

4. The method of claim 1, wherein selectively disengaging the at least one caster from the floor comprises extending at least one support of the at least one horizontal strut so that the at least one caster is not in contact with the floor.

5. The method of claim 4, comprising adjusting a length of the at least one support of the at least one horizontal strut.

6. The method of claim 4, comprising retracting the at least support of the at least one horizontal strut into a portion of the at least one horizontal strut to engage the at least one caster with the floor.

7. The method of claim 4, wherein the at least one horizontal strut comprises a pedal configured to translate the at least one support of the at least one horizontal strut between an extended position and a retracted position.

8. The method of claim 1, comprising: positioning the patient on the surgical table, connecting the limb of the patient to at least one distractor of the distraction frame, and applying a distraction force to the limb of the patient using the at least one distractor.

9. The method of claim 1, wherein selectively disengaging the at least one wheel from the floor comprises retracting the at least one wheel into a portion of the table mount.

10. The method of claim 1, wherein the at least one wheel is disengaged from the floor using one or more levers.

11. The method of claim 1, comprising pivoting the at least one horizontal strut relative to the table mount.

12. The method of claim 1, comprising telescopically adjusting a length of the at least one horizontal strut.

13. The method of claim 1, wherein the at least one horizontal strut comprises a gas cylinder to counterbalance at least a portion of the weight of the at least one horizontal strut and/or at least a portion of the weight carried by the at least one horizontal strut.

14. The method of claim 1, comprising moving the at least one vertical strut along the at least one horizontal strut.

15. The method of claim 1, comprising telescopically adjusting a length of the at least one vertical strut.

16. The method of claim 1, wherein the at least one vertical strut comprises a gas cylinder to counterbalance at least a portion of the weight of the at least one vertical strut and/or at least a portion of the weight carried by the at least one vertical strut.

* * * * *